United States Patent
Librach et al.

(10) Patent No.: US 12,129,481 B2
(45) Date of Patent: *Oct. 29, 2024

(54) USE OF CELLS DERIVED FROM FIRST TRIMESTER UMBILICAL CORD TISSUE

(71) Applicants: REPROBIOGEN INC., Toronto (CA); Shangmian Yie, Toronto (CA); Rong Xiao, Toronto (CA)

(72) Inventors: Clifford L. Librach, Toronto (CA); Shangmian Yie, Toronto (CA); Rong Xiao, Toronto (CA)

(73) Assignee: REPROBIOGEN INC., Toronto (CA)

( * ) Notice: Subject to any disclaimer, the term of this patent is extended or adjusted under 35 U.S.C. 154(b) by 463 days.

This patent is subject to a terminal disclaimer.

(21) Appl. No.: 17/181,482

(22) Filed: Feb. 22, 2021

(65) Prior Publication Data

US 2021/0246420 A1 Aug. 12, 2021

Related U.S. Application Data

(63) Continuation-in-part of application No. 15/239,261, filed on Aug. 17, 2016, now Pat. No. 10,925,903, which is a continuation-in-part of application No. 12/114,182, filed on May 2, 2008, now abandoned.

(60) Provisional application No. 60/972,022, filed on Sep. 13, 2007.

(51) Int. Cl.
*C12N 5/073* (2010.01)
*A01N 1/02* (2006.01)

(52) U.S. Cl.
CPC ........... *C12N 5/0605* (2013.01); *A01N 1/021* (2013.01); *A01N 1/0284* (2013.01); *C12N 2509/00* (2013.01)

(58) Field of Classification Search
CPC .............. C12N 5/0605; C12N 2509/00; C12N 2503/02; C12N 5/069; A01N 1/021; A01N 1/0284; A61K 35/44; A61K 35/34
See application file for complete search history.

(56) References Cited

U.S. PATENT DOCUMENTS

| | | | |
|---|---|---|---|
| 2005/0148074 A1 | 7/2005 | Davies et al. | |
| 2006/0223177 A1 | 10/2006 | Harris et al. | |
| 2007/0275362 A1 | 11/2007 | Edinger et al. | |
| 2008/0152630 A1 | 6/2008 | Ginis et al. | |

FOREIGN PATENT DOCUMENTS

| | | |
|---|---|---|
| CA | 2515469 C | 12/2013 |
| WO | 9622362 A1 | 7/1996 |
| WO | 2007071048 A1 | 6/2007 |

OTHER PUBLICATIONS

Liu et al., Effect of Human Umbilical Cord Perivascular Cell-Conditioned Media in an Adult Zebrafish Model of Traumatic Brain Injury, Zebrafish, vol. 17, p. 177-186. (Year: 2020).*
Abbar et al., Induced Pluripotent Stem Cells: Reprogramming Platforms and Applications in Cell Replacement Therapy, BioResearch Open Access, vol. 9, p. 121-136. (Year: 2020).*
Hong et al., Ontogeny of Human Umbilical Cord Perivascular Cells:Molecular and Fate Potential Changes During Gestation, Stem Cells and Development, vol. 22, p. 2425-2439. (Year: 2013).*
Schmidt et al., The roles of the reprogramming factors Oct4, Sox2 and Klf4 in resetting the somatic cell epigenome during induced pluripotent stem cell generation, Genome Biology, vol. 13, p. 1-11. (Year: 2012).*
Kim et al., Conditioned medium from the three-dimensional culture of human umbilical cord perivascular cells accelerate the migration and proliferation of human keratinocyte and fibroblast, Journal of Biomaterials and Polymer Edition ,abstract (Year: 2017).*
Mordwinkin et al., A Review of Human Pluripotent Stem Cell-Derived Cardiomyocytes for High-Throughput Drug Discovery, Cardiotoxicity Screening, and Publication Standards, Journal of Cardiovascular Translational Research, p. 22-30. (Year: 2013).*
Campagnoli et al., "Identification of Mesenchymal Stem/Progenitor Cells in Human First-trimester Fetal Blood, Liver and Bonemarrow," Blood, Oct. 2001, vol. 98 (8), pp. 2396-2402.
Canadian Patent Application No. 2,630,708, Office Action dated May 14, 2014.
Canadian Patent Application No. 26307080, Office Action dated Jun. 15, 2016.
Carlin et al., "Expression of Early Transcription Factors Oct-4, Sox-2 and Nanog by Porcine Umbilical Cord (PUC) Matrix Cells," Reproductive Biology and Endocrinology, Feb. 2006, vol. 4 (8), pp. 1-13.
Guillot et al., "Human First-Trimester Fetal MSC Express Pluripotency Markers and Grow Faster and Have Longer Telomeres Than Adult MSC," Stem Cells, Mar. 2007, vol. 25 (3), pp. 646-654.
Kehat et al., "Human Embryonic Stem Cells Can Differentiate Into Myocytes With Structural and Functional Properties of Cardiomyocytes," Journal of Clinical Investigation, Aug. 2001, vol. 108 (3), pp. 407-414.

(Continued)

*Primary Examiner* — Adam Weidner
*Assistant Examiner* — Tiffany M Gough
(74) *Attorney, Agent, or Firm* — Leber IP LAW; Shelly M. Fujikawa

(57) ABSTRACT

A method of isolating a pluripotent cell from human umbilical cord is described herein. Cells so isolated may be reprogrammed as pluripotent cells and differentiated for use in cardiovascular treatment, may be used in screening cardiovascular drug candidates, or may be used in cell-based and cell-free therapy for inflammatory conditions. The method involves collecting a sample of umbilical cord from fetal tissue obtained at less than 13 weeks of gestation, for example a first trimester umbilical cord. The sample is treated to obtain isolated umbilical cord cells, after which the isolated umbilical cord cells are incubated. Cells obtained in this way can be differentiated for use in treating conditions of cell damage, by supplanting the function of a damaged cell in a condition such as spinal cord injury, cardiovascular injury or heart disease.

20 Claims, 29 Drawing Sheets

(56) References Cited

OTHER PUBLICATIONS

Kim et al., "Mesenchymal Progenitor Cells in the Human Umbilical Cord," Annals of Hematology, Dec. 2004, vol. 83 (12), pp. 733-738.
Lu et al., "Isolation and Characterization of Human Umbilical Cord Mesenchymal Stem Cells With Hematopoiesis-supportive Function and Other Potentials," The Hematology Journal, Aug. 2006, vol. 91 (8), pp. 1017-1026.
Portman-Lanz et al., "Placental Mesenchymal Stem Cells as Potential Autologous Graft for Pre- and Perimatal Neuroregeneration," American Journal of Obstetrics and Gynecology, Mar. 2006, vol. 194 (3), pp. 664-673.
U.S. Appl. No. 15/239,261, Non-Final Office Action dated Dec. 9, 2019.
U.S. Appl. No. 12/114,182, Office Action dated Oct. 20, 2016.
U.S. Appl. No. 15/239,261, Advisory Action dated Aug. 30, 2019.
U.S. Appl. No. 15/239,261, Final Office Action dated May 15, 2019.
U.S. Appl. No. 15/239,261, Notice of Allowance dated Sep. 15, 2020.
U.S. Appl. No. 15/239,261, Notice of Allowance dated Sep. 23, 2020.
U.S. Appl. No. 15/239,261, Restriction Requirement dated Mar. 28, 2018.
U.S. Appl. No. 15/239,261, Non-Final Office Action dated Sep. 6, 2018.

\* cited by examiner

Treatments:
Bar 1: CM +Lysis;
Bar 2: CM –Lysis;
Bar 3: EV +Lysis; and
Bar 4: EV –Lysis

USE OF CELLS DERIVED FROM FIRST TRIMESTER UMBILICAL CORD TISSUE

CROSS REFERENCE TO RELATED APPLICATIONS

This application is a continuation-in-part of and claims the benefit of priority of U.S. patent application Ser. No. 15/239,261 filed Aug. 17, 2016; which is a continuation-in-part of U.S. patent application Ser. No. 12/114,182 filed May 2, 2008 to which the benefit of priority is claimed; and which claims the benefit of priority of U.S. Provisional Patent Application Ser. No. 60/972,022, filed Sep. 13, 2007, all of which are hereby incorporated by reference.

FIELD

The present disclosure relates generally to human stem cells. More particularly, the present disclosure relates to a method of isolating and expanding stem cells from first trimester umbilical cords, and uses therefor.

BACKGROUND

Stem cells are unspecialized human or animal cells that can produce mature specialized body cells and at the same time replicate themselves. This ability to differentiate into specialized cells has led to much research into their use for treating such fatal diseases and disorders as Parkinson's and Alzheimer's diseases, spinal cord injury, stroke, burns, heart disease, diabetes, osteoarthritis and rheumatoid arthritis. Stem cells are derived from either embryos or adult tissues. Embryonic stem cells are derived from a blastocyst typically containing 200 to 250 cells. Their use has been hampered by the ethical considerations associated with their isolation.

It has also been reported that mesenchymal-like stem cells can be isolated from the perivascular layer of umbilical cords at birth (HUCPVC), or from blood, bone marrow, skin, and other tissues. These postnatal cells have the ability to self-renew and differentiate to all cell types of mesenchymal lineage. Their use, however, has been hampered by the minimal quantities obtained. Furthermore, adult stem cells have significantly restricted differentiation potential, more DNA damage and shorter life spans as compared with pluripotent stem cells derived from fetal tissue.

U.S. Patent Publication 2005/0148074 A1 (Davies et al.) describes a method of isolating progenitor cells from the Wharton's jelly present in human umbilical cord tissue. However, this method requires tissue to be derived from full-term babies.

It is desirable to provide a method for isolating and expanding stem cells from umbilical cord tissue at a stage earlier than full-term.

SUMMARY

It is an object of the present disclosure to obviate or mitigate at least one disadvantage of previous methods for obtaining or using stem cells.

There is described herein a method of isolating pluripotent human umbilical cord perivascular cells for treating cardiovascular injury or heart disease. The isolated perivascular cells are reprogrammed as pluripotent cells for differentiation into cardiomyocytes expressing cTnI, and the pluripotent human umbilical cord perivascular cells are obtained by: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated perivascular cells, by: washing the umbilical cord with PBS, cutting the umbilical cord, comprising an artery and two vessels, into smaller cut pieces, treating the cut pieces with collagenase to obtain isolated perivascular cells, and washing the isolated perivascular cells with PBS; and incubating the isolated perivascular cells, by suspending the isolated perivascular cells in a maintenance medium comprising α-MEM, penicillin-streptomycin, and amphotericin; and maintaining the isolated perivascular cells by: washing the isolated perivascular cells with PBS; adding trypsin-EDTA; adding at least one gene reprogramming factor selected from the group consisting of OCT-4, KLF-4, SOX-2, GLIS1, and c-MYC; harvesting the isolated perivascular cells into a tube containing maintenance medium; separating the isolated perivascular cells from the maintenance medium; mixing the isolated perivascular cells with new maintenance medium; diluting the new maintenance medium containing the isolated perivascular cells with additional maintenance medium to obtain a diluted maintenance medium containing the isolated perivascular cells; maintaining the diluted maintenance medium containing the isolated perivascular cells under appropriate growth conditions of 37° C., 5% $CO_2$ in a maintenance medium, and changing the maintenance medium every 3-7 days; and suspending the maintained cells. In this method, prior to cutting the umbilical cord into smaller cut pieces, the umbilical cord is from 0.5-2.0 cm in length and comprises an artery; and the isolated perivascular cells express one or more transcription factor associated with undifferentiated stem cells; and the transcription factor is OCT-4, SOX-2, or Nanog.

According to another aspect described herein, a method is provided in which pluripotent human umbilical cord perivascular cells are isolated for use in screening of a drug candidate to treat cardiovascular injury or heart disease, wherein the isolated perivascular cells differentiate into cardiomyocytes expressing cTnl, and wherein the pluripotent human umbilical cord perivascular cells are obtained by the following steps: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated perivascular cells, by: washing the umbilical cord with PBS, cutting the umbilical cord, comprising an artery and two vessels, into smaller cut pieces, treating the cut pieces with collagenase to obtain isolated perivascular cells, and washing the isolated perivascular cells with PBS; and incubating the isolated perivascular cells, by suspending the isolated perivascular cells in a maintenance medium comprising α-MEM, penicillin-streptomycin, and amphotericin; and maintaining the isolated perivascular cells by: washing the isolated perivascular cells with PBS; adding trypsin-EDTA; harvesting the isolated perivascular cells into a tube containing maintenance medium; separating the isolated perivascular cells from the maintenance medium; mixing the isolated perivascular cells with new maintenance medium; diluting the new maintenance medium containing the isolated perivascular cells with additional maintenance medium to obtain a diluted maintenance medium containing the isolated perivascular cells; maintaining the diluted maintenance medium containing the isolated perivascular cells under appropriate growth conditions of 37° C., 5% $CO_2$ in a maintenance medium, and changing the maintenance medium every 3-7 days; and suspending the maintained cells. In this method, prior to cutting the umbilical cord into smaller cut pieces, the umbilical cord is from 0.5-2.0 cm in length and comprises an artery; the isolated perivascular cells express one or more transcription factor associated with undifferentiated stem cells; and the transcription factor is OCT-4, SOX-2, or Nanog; and wherein efficacy of the drug candidate is evaluated upon exposure of the isolated perivascular cells thereto.

Further, there is described herein a method of isolating pluripotent human umbilical cord perivascular cells for preparing a cell-free composition for treating an inflammatory condition, wherein the isolated perivascular cells are differentiated into, or reprogrammed as pluripotent cells for differentiation into, a homogeneous perivascular cell population with generational stability, wherein the pluripotent human umbilical cord perivascular cells are obtained by: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated perivascular cells, by: washing the umbilical cord with PBS, cutting the umbilical cord, comprising an artery and two vessels, into smaller cut pieces, treating the cut pieces with collagenase to obtain isolated perivascular cells, and washing the isolated perivascular cells with PBS; and incubating the isolated perivascular cells, by suspending the isolated perivascular cells in a maintenance medium comprising α-MEM, penicillin-streptomycin, and amphotericin; and maintaining the isolated perivascular cells by: washing the isolated perivascular cells with PBS; adding trypsin-EDTA; optionally adding at least one gene reprogramming factor selected from the group consisting of OCT-4, KLF-4, SOX-2, GLIS1, and c-MYC; harvesting the isolated perivascular cells into a tube containing maintenance medium; separating the isolated perivascular cells from the maintenance medium; mixing the isolated perivascular cells with new maintenance medium; diluting the new maintenance medium containing the isolated perivascular cells with additional maintenance medium to obtain a diluted maintenance medium containing the isolated perivascular cells; maintaining the diluted maintenance medium containing the isolated perivascular cells under appropriate growth conditions of 37° C., 5% $CO_2$ in a maintenance medium, and changing the maintenance medium every 3-7 days; and suspending the maintained cells; and preparing the cell-free composition from the maintenance medium comprising secretions of the isolated perivascular cells. In this method, prior to cutting the umbilical cord into smaller cut pieces, the umbilical cord is from 0.5-2.0 cm in length and comprises an artery; and the isolated perivascular cells express one or more transcription factor associated with undifferentiated stem cells; and the transcription factor is OCT-4, SOX-2, or Nanog.

Other aspects and features will become apparent to those ordinarily skilled in the art upon review of the following description of specific embodiments in conjunction with the accompanying figures.

BRIEF DESCRIPTION OF THE DRAWINGS

Embodiments will now be described, by way of example only, with reference to the attached Figures.

DETAILED DESCRIPTION

Figure 1:
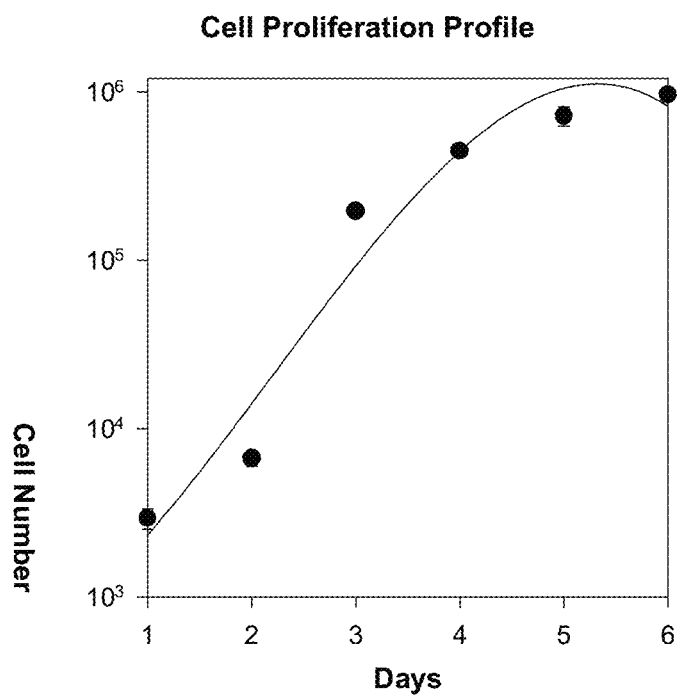
FIG. 1 shows a proliferation profile.

Methods described herein include methods for isolating cells for use in treatment of cardiovascular injury; for use in screening cardiovascular drug candidates; and for use in cell-free or cell-based therapies for inflammatory conditions Use in Treatment of Cardiovascular Injury or Heart Disease.

A method is described for isolating pluripotent human umbilical cord perivascular cells for treating cardiovascular injury or heart disease, wherein the isolated perivascular cells are reprogrammed as pluripotent cells for differentiation into cardiomyocytes expressing cTnl. The pluripotent human umbilical cord perivascular cells are obtained by: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated perivascular cells, by: washing the umbilical cord with PBS, cutting the umbilical cord, comprising an artery and two vessels, into smaller cut pieces, treating the cut pieces with collagenase to obtain isolated perivascular cells, and washing the isolated perivascular cells with PBS.

Subsequently, the isolated perivascular cells are incubated by suspending the isolated perivascular cells in a maintenance medium comprising α-MEM, penicillin-streptomycin, and amphotericin; and the cells are maintained by: washing the isolated perivascular cells with PBS; adding trypsin-EDTA; adding at least one gene reprogramming factor selected from the group consisting of OCT-4, KLF-4, SOX-2, GLIS1, and c-MYC; harvesting the isolated perivascular cells into a tube containing maintenance medium; separating the isolated perivascular cells from the maintenance medium; mixing the isolated perivascular cells with new maintenance medium; diluting the new maintenance medium containing the isolated perivascular cells with additional maintenance medium to obtain a diluted maintenance medium containing the isolated perivascular cells; maintaining the diluted maintenance medium containing the isolated perivascular cells under appropriate growth conditions of 37° C., 5% $CO_2$ in a maintenance medium, and changing the maintenance medium every 3-7 days; and suspending the maintained cells.

Prior to cutting the umbilical cord into smaller cut pieces, the umbilical cord is from 0.5-2.0 cm in length and comprises an artery. The isolated perivascular cells express one or more transcription factor associated with undifferentiated stem cells; and the transcription factor is OCT-4, SOX-2, or Nanog.

The maintaining the isolated perivascular cells may additionally comprise: freezing the isolated perivascular cells; and thawing and restoring the isolated perivascular cells to viability.

The collagenase used may be Type I collagenase, for example at 1 mg/mL.

The freezing of the isolated perivascular cells may comprise: washing the isolated perivascular cells with PBS; adding trypsin-EDTA; harvesting the isolated perivascular cells into a tube containing maintenance medium; separating the isolated perivascular cells from the maintenance medium; cooling the isolated perivascular cells to 4° C.; mixing the isolated perivascular cells with a freezing medium at 4° C., said freezing medium comprising DMSO; transferring the freezing medium containing the isolated perivascular cells to vials pre-chilled to −70° C.; storing the vials at −70° C. for 24 h; and storing the vials in liquid nitrogen.

The thawing and restoring the isolated perivascular cells may comprise warming the vials to 37° C.; separating the isolated perivascular cells from the freezing medium; mixing the isolated perivascular cells with maintenance medium; maintaining the maintenance medium containing the isolated perivascular cells under appropriate growth conditions of 37° C., 5% $CO_2$, for 24 hours; replacing the maintenance medium with new maintenance medium; and maintaining the new maintenance medium containing the material under appropriate growth conditions, said conditions being 37° C., 5% $CO_2$ and changing the new maintenance medium every 3-7 days.

The maintaining the isolated perivascular cells may further comprise: (i) aspirating the medium from the cells when the density of cells exceeds about 70% of the surface of a culture dish or flask in which the cells are maintained; (ii) washing the cells with PBS; (iii) adding trypsin-EDTA to cover the cells until the cells lift off of the dish or flask; and (iv) resuspending the cells in maintenance medium.

Use in Screening Cardiovascular Drug Candidates.

A method is described for isolating pluripotent human umbilical cord perivascular cells for screening of a drug candidate to treat cardiovascular injury or heart disease, wherein the isolated perivascular cells differentiate into cardiomyocytes expressing cTnl. The pluripotent human umbilical cord perivascular cells are obtained by: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated perivascular cells, by: washing the umbilical cord with PBS, cutting the umbilical cord, comprising an artery and two vessels, into smaller cut pieces, treating the cut pieces with collagenase to obtain isolated perivascular cells, and washing the isolated perivascular cells with PBS.

The cells so obtained are incubated by suspending the isolated perivascular cells in a maintenance medium comprising α-MEM, penicillin-streptomycin, and amphotericin; and maintaining the isolated perivascular cells by: washing the isolated perivascular cells with PBS; adding trypsin-EDTA; harvesting the isolated perivascular cells into a tube containing maintenance medium; separating the isolated perivascular cells from the maintenance medium; mixing the isolated perivascular cells with new maintenance medium; diluting the new maintenance medium containing the isolated perivascular cells with additional maintenance medium to obtain a diluted maintenance medium containing the isolated perivascular cells; maintaining the diluted maintenance medium containing the isolated perivascular cells under appropriate growth conditions of 37° C., 5% $CO_2$ in a maintenance medium, and changing the maintenance medium every 3-7 days; and suspending the maintained cells.

According to the method, prior to cutting the umbilical cord into smaller cut pieces, the umbilical cord is from 0.5-2.0 cm in length and comprises an artery. The isolated perivascular cells express one or more transcription factor associated with undifferentiated stem cells; and the transcription factor is OCT-4, SOX-2, or Nanog. The efficacy of the drug candidate is evaluated upon exposure of the isolated perivascular cells thereto.

Maintaining the isolated perivascular cells may comprise the step of adding at least one gene reprogramming factor selected from the group consisting of OCT-4, KLF-4, SOX-2, GLIS1, and c-MYC.

The isolated perivascular cells may be maintained by freezing the isolated perivascular cells; and thawing and restoring the isolated perivascular cells to viability.

The collagenase may be Type I, used at 1 mg/mL, for example.

The freezing of the isolated perivascular cells may comprise washing the isolated perivascular cells with PBS; adding trypsin-EDTA; harvesting the isolated perivascular cells into a tube containing maintenance medium; separating the isolated perivascular cells from the maintenance medium; cooling the isolated perivascular cells to 4° C.; mixing the isolated perivascular cells with a freezing medium at 4° C., said freezing medium comprising DMSO; transferring the freezing medium containing the isolated perivascular cells to vials pre-chilled to −70° C.; storing the vials at −70° C. for 24 h; and storing the vials in liquid nitrogen.

The thawing and restoring of the isolated perivascular cells may comprise warming the vials to 37° C.; separating the isolated perivascular cells from the freezing medium; mixing the isolated perivascular cells with maintenance medium; maintaining the maintenance medium containing the isolated perivascular cells under appropriate growth conditions of 37° C., 5% $CO_2$, for 24 hours; replacing the maintenance medium with new maintenance medium; and maintaining the new maintenance medium containing the material under appropriate growth conditions, said conditions being 37° C., 5% $CO_2$ and changing the new maintenance medium every 3-7 days.

Maintaining the isolated perivascular cells may further comprise: (i) aspirating the medium from the cells when the density of cells exceeds about 70% of the surface of a culture dish or flask in which the cells are maintained; (ii) washing the cells with PBS; (iii) adding trypsin-EDTA to cover the cells until the cells lift off of the dish or flask; and (iv) resuspending the cells in maintenance medium.

Use in Cell-Free Therapy for Inflammatory Conditions.

A method is described for isolating pluripotent human umbilical cord perivascular cells for preparing a cell-free composition for treating an inflammatory condition, wherein the isolated perivascular cells are differentiated into, or reprogrammed as pluripotent cells for differentiation into, a homogeneous perivascular cell population with generational stability.

In this method, pluripotent human umbilical cord perivascular cells are obtained by: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated perivascular cells, by: washing the umbilical cord with PBS, cutting the umbilical cord, comprising an artery and two vessels, into smaller cut pieces, treating the cut pieces with collagenase to obtain isolated perivascular cells, and washing the isolated perivascular cells with PBS; and incubating the isolated perivascular cells, by suspending the isolated perivascular cells in a maintenance medium comprising α-MEM, penicillin-streptomycin, and amphotericin; and maintaining the isolated perivascular cells by: washing the isolated perivascular cells with PBS; adding trypsin-EDTA; optionally adding at least one gene reprogramming factor selected from the group consisting of OCT-4, KLF-4, SOX-2, GLIS1, and c-MYC; harvesting the isolated perivascular cells into a tube containing maintenance medium; separating the isolated perivascular cells from the maintenance medium; mixing the isolated perivascular cells with new maintenance medium; diluting the new maintenance medium containing the isolated perivascular cells with additional maintenance medium to obtain a diluted maintenance medium containing the isolated perivascular cells; maintaining the diluted maintenance medium containing the isolated perivascular cells under appropriate growth conditions of 37° C., 5% $CO_2$ in a maintenance medium, and changing the maintenance medium every 3-7 days; and suspending the maintained cells.

The cell-free composition is prepared from the maintenance medium comprising secretions of the isolated perivascular cells.

According to the method, prior to cutting the umbilical cord into smaller cut pieces, the umbilical cord is from 0.5-2.0 cm in length and comprises an artery. The isolated perivascular cells express one or more transcription factor associated with undifferentiated stem cells; and the transcription factor is OCT-4, SOX-2, or Nanog.

Maintaining the isolated perivascular cells may additionally comprise: freezing the isolated perivascular cells; and thawing and restoring the isolated perivascular cells to viability.

The collagenase may be Type I, used at 1 mg/mL, for example.

The freezing of the isolated perivascular cells may comprise: washing the isolated perivascular cells with PBS; adding trypsin-EDTA; harvesting the isolated perivascular cells into a tube containing maintenance medium; separating the isolated perivascular cells from the maintenance medium; cooling the isolated perivascular cells to 4° C.; mixing the isolated perivascular cells with a freezing medium at 4° C., said freezing medium comprising DMSO; transferring the freezing medium containing the isolated perivascular cells to vials pre-chilled to −70° C.; storing the vials at −70° C. for 24 h; and storing the vials in liquid nitrogen.

The step of thawing and restoring the isolated perivascular cells may comprise: warming the vials to 37° C.; separating the isolated perivascular cells from the freezing medium; mixing the isolated perivascular cells with maintenance medium; maintaining the maintenance medium containing the isolated perivascular cells under appropriate growth conditions of 37° C., 5% $CO_2$, for 24 hours; replacing the maintenance medium with new maintenance medium; and maintaining the new maintenance medium containing the material under appropriate growth conditions, said conditions being 37° C., 5% $CO_2$ and changing the new maintenance medium every 3-7 days.

Maintaining the isolated perivascular cells may further comprise: (i) aspirating the medium from the cells when the density of cells exceeds about 70% of the surface of a culture dish or flask in which the cells are maintained; (ii) washing the cells with PBS; (iii) adding trypsin-EDTA to cover the cells until the cells lift off of the dish or flask; and (iv) resuspending the cells in maintenance medium.

In certain embodiments the optional step of adding at least one gene reprogramming factor is conducted. In other embodiments, this optional step is not conducted.

A method is described for isolating and expanding stem cells, and more particularly a method wherein the stem cells are derived from first trimester umbilical cords. In accordance with one aspect described herein, there is provided a method of isolating a pluripotent cell from human umbilical cord, said method comprising: collecting a sample of umbilical cord from fetal tissue obtained at less than 20 weeks of gestation; treating the sample to obtain isolated umbilical cord cells; and incubating the isolated umbilical cord cells. Additional optional steps may also include: maintaining the isolated umbilical cord cells, freezing the isolated umbilical cord cells, and thawing and restoring the isolated umbilical cord cells to viability. In one embodiment, umbilical cord samples can be obtained at less than 13 weeks of gestation.

There is described herein a method of treating a condition of cellular damage. The method comprises supplanting the function of a damaged cell with a pluripotent cell from a human umbilical cord. The pluripotent cell is obtained by: collecting an umbilical cord from fetal tissue obtained at less than 13 weeks of gestation, by collecting fetal placenta tissue by surgical aspiration; and separating the umbilical cord from the fetal placenta tissue; treating the umbilical cord to obtain isolated umbilical cord cells, by: washing the umbilical cord with PBS, cutting the umbilical cord, comprising an artery and two vessels, into smaller cut pieces, treating the cut pieces with collagenase to obtain isolated umbilical cord cells, and washing the isolated umbilical cord cells with PBS; and incubating the isolated umbilical cord cells, by suspending the isolated umbilical cord cells in a maintenance medium comprising α-MEM, penicillin-streptomycin, and amphotericin; and maintaining the isolated umbilical cord cells under appropriate growth conditions of 37° C., 5% $CO_2$; wherein prior to cutting the umbilical cord into smaller cut pieces, the umbilical cord is from 0.5-2.0 cm in length and comprises an artery; wherein the isolated umbilical cord cells express one or more transcription factor associated with undifferentiated stem cells; and the transcription factor is OCT-4, SOX-2, or Nanog; and wherein the condition of cellular damage is spinal cord injury, Parkinson's disease, Alzheimer's disease, cardiovascular injury, heart disease, stroke, burn, diabetes, osteoarthritis or rheumatoid arthritis.

The method may involve maintaining the isolated umbilical cord cells and changing the maintenance medium every 3-7 days; freezing the isolated umbilical cord cells; and thawing and restoring the isolated umbilical cord cells to viability. Optionally, the collagenase is Type I at 1 mg/mL.

Further, the method may involve maintaining the isolated umbilical cord cells by washing the isolated umbilical cord cells with PBS; adding trypsin-EDTA; harvesting the isolated umbilical cord cells into a tube containing maintenance medium; separating the isolated umbilical cord cells from the maintenance medium; mixing the isolated umbilical cord cells with new maintenance medium; diluting the new maintenance medium containing the isolated umbilical cord cells with additional maintenance medium to obtain a diluted maintenance medium containing the isolated umbilical cord cells; and maintaining the diluted maintenance medium containing the isolated umbilical cord cells under appropriate growth conditions of 37° C., 5% $CO_2$ and changing the maintenance medium every 3-7 days.

The method may involve freezing the isolated umbilical cord cells by washing the isolated umbilical cord cells with PBS; adding trypsin-EDTA; harvesting the isolated umbilical cord cells into a tube containing maintenance medium; separating the isolated umbilical cord cells from the maintenance medium; cooling the isolated umbilical cord cells to 4° C.; mixing the isolated umbilical cord cells with a freezing medium at 4° C., said freezing medium comprising DMSO; transferring the freezing medium containing the isolated umbilical cord cells to vials pre-chilled to −70° C.; storing the vials at −70° C. for 24 h; and storing the vials in liquid nitrogen.

The method may optionally involve thawing and restoring the isolated umbilical cord cells, which comprises: warming the vials to 37° C.; separating the isolated umbilical cord cells from the freezing medium; mixing the isolated umbilical cord cells with maintenance medium; maintaining the maintenance medium containing the isolated umbilical cord cells under appropriate growth conditions of 37° C., 5% $CO_2$, for 24 hours; replacing the maintenance medium with new maintenance medium; and maintaining the new maintenance medium containing the material under appropriate growth conditions, said conditions being 37° C., 5% $CO_2$ and changing the new maintenance medium every 3-7 days.

The method described herein may involve maintaining the isolated umbilical cord cells with the following steps: (i) aspirating the medium from the cells when the density of cells exceeds about 70% of the surface of a culture dish or flask in which the cells are maintained; (ii) washing the cells with PBS; (iii) adding trypsin-EDTA to cover the cells until the cells lift off of the dish or flask; and (iv) resuspending the cells in maintenance medium.

The damaged cell according to the method may be supplanted by the pluripotent cell differentiated to a neuronal cell, an osteoblast, a chondrocyte, a myocyte, an adipocyte, or a β-pancreatic islet cell. For example, the pluripotent cell is differentiated to a neuronal cell. This may be in a situation where the condition comprises spinal cord injury, Parkinson's disease or Alzheimer's disease, and spinal cord injury in particular. The pluripotent cell may be differentiated to a cardiomyocyte, which would be the situation when the condition is cardiovascular injury or heart disease.

According to one exemplary embodiment, collection of the sample can comprise: collecting fetal placenta tissue by surgical aspiration; and separating the umbilical cords from the fetal placenta tissue. Furthermore, the step of treating the sample can comprise: washing the umbilical cord with PBS; cutting the umbilical cord into pieces; treating the umbilical cord pieces with collagenase to obtain isolated umbilical cord cells; and washing the isolated umbilical cord cells with PBS. Any type of collagenase may be used provided it achieves the effect of separating the cells such as, for example, Type I collagenase at 1 mg/mL.

The incubating step may comprise: suspending the isolated umbilical cord cells in a maintenance medium composed of α-MEM, Fetal Bovine Serum, penicillin-streptomycin, and amphotericin; and maintaining the material under appropriate growth conditions of 37° C., 5% $CO_2$ and changing the maintenance medium every 3-7 days. Other maintenance medium or growth conditions may be appropriate as long as cell viability or growth is maintained.

In accordance with one embodiment, the present method can comprise an optional step of maintaining the isolated umbilical cord cells. Ideally, this step can comprise: washing the isolated umbilical cord cells with PBS; adding trypsin-EDTA; harvesting the isolated umbilical cord cells into a tube containing maintenance medium; separating the isolated umbilical cord cells from the maintenance medium; mixing the isolated umbilical cord cells with new maintenance medium; diluting the new maintenance medium containing the isolated umbilical cord cells with additional maintenance medium to obtain a diluted maintenance medium containing the isolated umbilical cord cells; and maintaining the diluted maintenance medium containing the isolated umbilical cord cells under appropriate growth conditions of 37° C., 5% $CO_2$ and changing the maintenance medium every 3-7 days. Other maintenance medium or growth conditions may be appropriate as long as cell viability or growth is maintained.

As mentioned above, another optional step in the method includes freezing the isolated umbilical cord cells. In one embodiment, this step may comprise: washing the isolated umbilical cord cells with PBS; adding trypsin-EDTA; harvesting the isolated umbilical cord cells into a tube containing maintenance medium; separating the isolated umbilical cord cells from the maintenance medium; cooling the isolated umbilical cord cells to 4° C.; mixing the isolated umbilical cord cells with a freezing medium at 4° C., the freezing medium comprising 80% Fetal Calf Serum and 20% DMSO; transferring the freezing medium containing the isolated umbilical cord cells to vials pre-chilled to −70° C.; storing the vials at −70° C. for 24 h; and storing the vials in liquid nitrogen. Other freezing medium may be appropriate as long as cell viability is maintained.

A further optional step in the described method includes thawing and restoring the isolated umbilical cord cells. In one embodiment, this step may comprise: warming the vials to 37° C.; separating the isolated umbilical cord cells from the freezing medium; mixing the isolated umbilical cord cells with maintenance medium; maintaining the maintenance medium containing the isolated umbilical cord cells under appropriate growth conditions of 37° C., 5% $CO_2$, for 24 hours; replacing the maintenance medium with new maintenance medium; and maintaining the new maintenance medium containing the material under appropriate growth conditions, said conditions being 37° C., 5% $CO_2$ and changing the new maintenance medium every 3-7 days. Other maintenance medium or growth conditions may be appropriate as long as cell viability or growth is restored.

The isolated umbilical cord cells may express one or more transcription factors associated with undifferentiated stem cells. Exemplary transcription factors include OCT-4, SOX-2, or Nanog.

The cells isolated according to the method described may undergo transformation into a differentiated cell such as a neuronal cell, an osteoblast, a chondrocyte, a myocyte, an adipocyte, or a β-pancreatic islet cell.

In accordance with another aspect, there is provided a method of obtaining a differentiated cell. In one embodiment, this method involves isolating the cell as described above from human umbilical cord and transforming it using any method acceptable to a person skilled in the art.

Treatment of conditions may be achieved as described herein where the condition requires the function of a damaged cell to be supplanted by a cell obtained according to the method described above. Such conditions may include Parkinson's disease, Alzheimer's disease, spinal cord injury, stroke, burn, heart disease, diabetes, osteoarthritis or rheumatoid arthritis.

Pluripotent cells or differentiated cells can be obtained by methods described herein.

While the first trimester of human gestation can be chronologically identified as the first 13 weeks of gestation, as used herein the term "first trimester" can be extended to further encompass from the 14th week to the 20th week of gestation. A person skilled in the art would recognize that cells isolated up to the 20th week of gestation according to the method described herein may still possess the described features found in those cells isolated in the first 13 weeks of gestation.

The steps described can be further sub-divided. In order to collect samples, fresh fetal-placenta samples are collected from first trimester terminated pregnancies by surgical aspiration into an aseptic bottle; the samples are then moved into dishes where they are searched using forceps, blades and Iris™ scissors for umbilical cords, which are removed.

In one embodiment, treating the umbilical cord sample involves: washing the sample several times with the Dulbecco's Phosphate Buffered Saline (PBS); cutting the sample into small pieces with the curved surgical scissors; transferring the cut sample into a centrifuge tube; digesting the sample; centrifuging; aspirating the supernatant; and washing the sample.

The resulting umbilical cord cells isolated from the treatment of the umbilical cord sample can be incubated by: preparing a warm maintenance medium; re-suspending the isolated umbilical cord cells in the maintenance medium; transferring the isolated umbilical cord cells into tissue culture dishes; adding maintenance medium; and keeping the isolated umbilical cord cells under appropriate growth conditions.

An optional step for the method of isolating cells includes maintaining the isolated umbilical cord cells. The maintenance of isolated umbilical cord cells is undertaken before the cells reach confluence or prior to the growth medium becoming acidic, whichever occurs first. However, the density of cells should exceed approximately 70% of the surface of the culture dishes. In order to maintain the isolated umbilical cord cells, essentially all of the medium is removed from the tissue culture dishes by aspiration; the cells are rinsed once with warmed PBS; room-temperature trypsin-EDTA is added to cover the cells; and the cells are incubated with the trypsin-EDTA until the cells begin to lift off. Cells are harvested into a tube containing maintenance medium and centrifuged to pellet the cell suspension; the media is removed by aspiration and the cells are re-suspended in maintenance medium; and a fraction of the maintenance medium is transferred into a flask containing maintenance medium. Maintenance of the cells in an undifferentiated state can be accomplished by repeating this procedure when the density of the cells exceeds approximately 70% of the surface of the culture flask at each passage.

Another optional step of the method of isolating cells is the storage of the isolated umbilical cord cells. Storage typically involves: freshly preparing freezing medium; harvesting isolated umbilical cord cells using trypsin-EDTA as described above to obtain harvested cells; briefly chilling the harvested cells; re-suspending the harvested cells in ice-cold freezing medium; placing the harvested in pre-chilled cryovials; placing the cryovials in a freezer for 24 hours; and transferring the cryovials to liquid nitrogen for long term storage.

Another optional step of the method of isolating cells is the thawing and restoring of the isolated umbilical cord cells to viability. This step typically involves: warming the maintenance medium; transferring the cryovial in the freezer containing the isolated umbilical cord cells to a water bath; transferring the isolated umbilical cord cells in the cryovial into a centrifuge tube and centrifuging; aspirating the supernatant and re-suspending the isolated umbilical cord cells in an appropriate amount of maintenance medium; and, at a predetermined time after thawing the isolated umbilical cord cells, removing all of the medium and replacing with fresh maintenance medium.

EXAMPLES

Example 1

Obtaining First Trimester HUCPV Cells

The following method describes obtaining first trimester human umbilical cord perivascular cells (HUPVC).

Materials—Reagents

A non-exhaustive list of possible reagents for use in the described method is provided below. Penicillin-streptomycin liquid containing 5000 U of penicillin and 5000 mg of streptomycin/mL (GIBCO; cat. no. 15070-63), aliquot and store at $-20°$ C. Amphotericin B solution (250 µg/ml, Sigma; cat. no. A-2942), aliquot and store at $-20°$ C. Dulbecco's phosphate-buffered saline (PBS) (+) (GIBCO™; cat. no. 14040-133), store at $4°$ C. Sterile water, tissue culture grade (GIBCO; cat. no. 15230-162), store at $4°$ C. Collagenase Type 1 (GIBCO; cat. no. 21985-023), store at $4°$ C. α-MEM (GIBCO; cat. no. 12571). Defined fetal bovine serum (HyClone, Logan, UT; cat. no. 30070-03) aliquot and store at $-20°$ C. Trypsin 0.25%/EDTA (GIBCO; cat. no. 25200-056), store at $-20°$ C. DMSO (Sigma™, cat. no. D-5879), store at room temperature. Any additional and acceptable reagents may be used.

Materials—Equipment

A non-exhaustive list of possible equipment to be used in the described method follows. Watchmakers' forceps (Fine Science Tools Inc., Vancouver, Canada); Iris scissors (Fine Science Tools Inc., cat. no. 14060-09) and dissecting curved surgical scissors (Fischer Scientific; cat. no. 08-935); single edge blades; Pipetmen (2, 10, 100, 200, and 1000 µL); 1-mL individually wrapped serological pipet (BD Biosciences; cat. no. 357522); 5-mL individually wrapped serological pipet (BD Biosciences; cat. no. 357543); 10-mL individually wrapped serological pipet (BD Biosciences; cat. no. 357551); 25-mL individually wrapped serological pipet (BD Biosciences; cat. no. 357525); 15 ml conical centrifuge tubes, high-clarity polypropylene (BD Biosciences; cat. no. 352196); 50 ml conical centrifuge tubes, high-clarity polypropylene (BD Biosciences; cat. no. 352070); 100×20 mm tissue culture dishes (TPP, cat no. 93100); 100×15 mm Petri dishes (Sigma, P5731); 75 cm² tissue culture flask (BD Biosciences; cat. no. 354114); Nalgene freezing box (Nalge Nunc, Rochester, NY; cat. no. 5100-0001); Cryogenic vials (VWR; cat. no. CA66008-284); UV tissue culture enclosure hood (Labconco); $37°$ C. water bath (VWR); Humidified incubator (Fisher); Inverted microscope with a range of phase contrast objectives (×4, ×10, ×20, and ×40) (Zeiss); liquid nitrogen storage tank; and a tabletop centrifuge. Any additional and acceptable equipment may be used.

Collection of Samples

Fresh fetal-placenta samples were collected from pregnancies terminated in the first trimester. The samples were surgically aspirated into an aseptic bottle, and immediately transported from operation room (OR) to the research lab for processing. All further steps described were undertaken in sterile conditions using appropriately sterile techniques. Samples were moved into the 100×15 mm petri dish. The samples were carefully searched for the umbilical cord using the forceps, blades and Iris™ scissors. The first trimester umbilical cord is a clear tube-like tissue connected to placental tissue. It is 0.5-2.0 cm in length and contains 2 vessels and one artery. The rest of any of the samples was put back into the bottle, which was filled with 10% formalin and pathology analysis.

Treatment of the Samples

Isolated umbilical cord was washed several times with PBS. The umbilical cord was cut into small pieces with the curved Iris™ scissors, and transferred into a 15 mL centrifuge tube. The sample was treated for 1 h with collagenase Type 1 (1 mg/ml) while in the 37° C. water bath. The sample was centrifuged at 800 rpm for 15 min at 4° C. to obtain a cell pellet comprising isolated umbilical cord cells and a collagenase supernatant. The collagenase supernatant was removed by aspiration. The cell pellet was washed twice with PBS, centrifuging each time at 800 rpm for 10 min at 4° C. to obtain a washed cell pellet and a PBS supernatant. The PBS supernatant was removed by aspiration.

Incubating the Isolated Umbilical Cord Cells

Maintenance medium (50 ml) was prepared by mixing 44 ml of α-MEM with 5 ml FBS, 0.5 ml of 100× Penicillin-streptomycin aliquot, and 100×0.5 ml Amphotericin B. The maintenance medium was warmed to 37° C. in the water bath before use. After treating the sample, the isolated umbilical cord cells were re-suspended in 1 mL of maintenance medium to obtain cells. The cells were transferred into 100×20 mm tissue culture dishes and 9 mL of maintenance medium was added. The dishes were placed in the incubator at 37° C. and 5% $CO_2$ for 3-7 days. The maintenance medium was changed every 2-3 days.

Maintenance of the Isolated Umbilical Cord Cells

The media was aspirated from the culture dishes and the cultures were rinsed once with PBS warmed to 37° C. in a water bath. Sufficient room temperature trypsin-EDTA was added to cover the cells, approximately 4 mL for a 100 mm dish. The cells were allowed to incubate at 37° C. until the cells just began to lift off. The cells were harvested into a tube containing 4 mL of maintenance medium and centrifuged to pellet the cell suspension (800 rpm for approximately 10 minutes). The media was removed by aspiration and the cells were re-suspended in approximately 2 mL of maintenance medium. Pipetting up and down against the bottom of the tube 4-6 times ensured that the cell pellet was disrupted to a single cell suspension.

In order to perform a 1:4 split of the cells, 0.5 mL of cells were transferred into a 75 $cm^2$ flask containing the balance of 10 mL of maintenance medium. The remainder of the cells could be stored or used for experiments. Continued maintenance as required to sustain the cells in an undifferentiated state was accomplished by repeat the above procedure when the density of cells exceeded 70% of the surface of the culture flask at each passage.

Storage of Material

Fresh freezing medium was prepared by mixing 80% FCS and 20% DMSO. Cryovials were pre-chilled to −70° C. in a Nalgene™ freezing box and cells at a concentration of between $5 \times 10^5$ and $1 \times 10^6$ cells/mL were harvested with trypsin-EDTA as described above. The majority of the media was removed by aspiration and the cells were chilled on ice for 1-2 min. The final cell pellet was re-suspended in ice-cold freezing medium. The cell solution (0.5 mL per cryovial) was transferred into the pre-chilled cryovials in the Nalgene™ freezing box. The Nalgene™ freezing box containing the cryovials was placed in a −70° C. freezer to arrive at frozen cells. Twenty four (24) hours after the cryovials were placed in the freezer, the frozen cells were transferred to liquid nitrogen for long term storage.

Thawing and Restoring the Material to Viability

Maintenance medium was warmed to 37° C. The cryovial containing the frozen cells was removed from the freezer and thawed quickly in a 37° C. water bath. Once thawed, the cells were transferred into 15 mL conical centrifuge tubes and centrifuged at 800 rpm for 10 minutes. The supernatant was removed by aspiration and the cell pellet was re-suspended in maintenance medium (5 mL for a 60 mm dish or 25 $cm^2$ flask; 10 mL for a 100 mm dish). Pipetting gently ensured that the cell pellet was disrupted into a single cell suspension. Twenty four (24) hours after thawing the cells all media was removed and replaced with fresh maintenance medium.

Results

FIG. 1 illustrates the proliferation profile of the cells in the material isolated from first trimester human umbilical cord. The number of cells is plotted against the number of days in culture. FIG. 1 shows an increase in cell number over 6 days, indicating that the cells are dividing.

Figure 2:
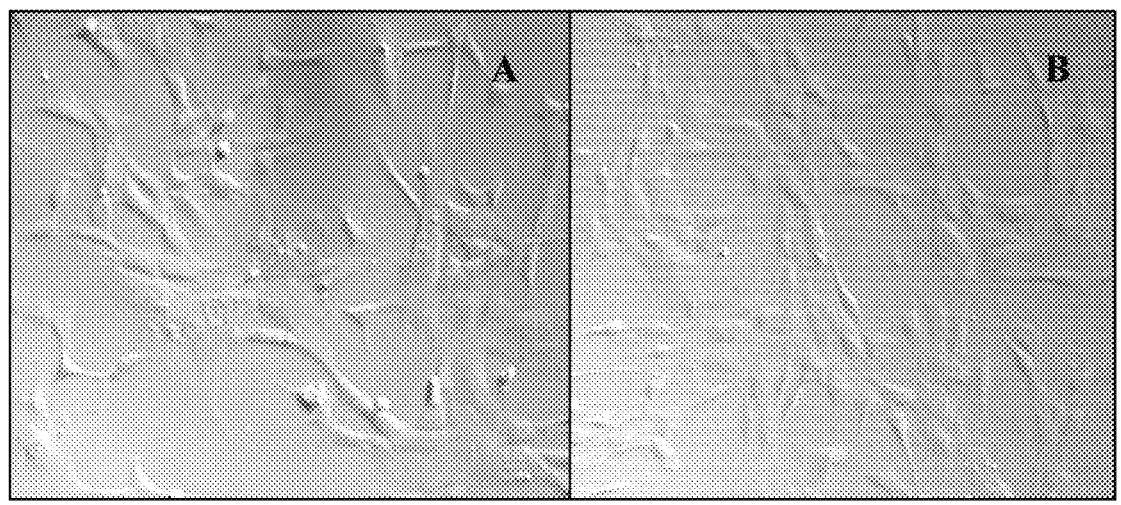
FIG. 2 is a micrograph at 100× magnification; cells are shown at second passage (A) and fifteenth passage (B).

FIG. 2 shows the morphology of the cells in the material isolated from first trimester human umbilical cord. The cells showed homogeneous fibroblast-like morphology. Part A of FIG. 2 shows the initial population of the cells at the second passage, while Part B of FIG. 2 shows the population of the cells at the $15^{th}$ passage. In both parts, the magnification is 100×.

Figure 3:
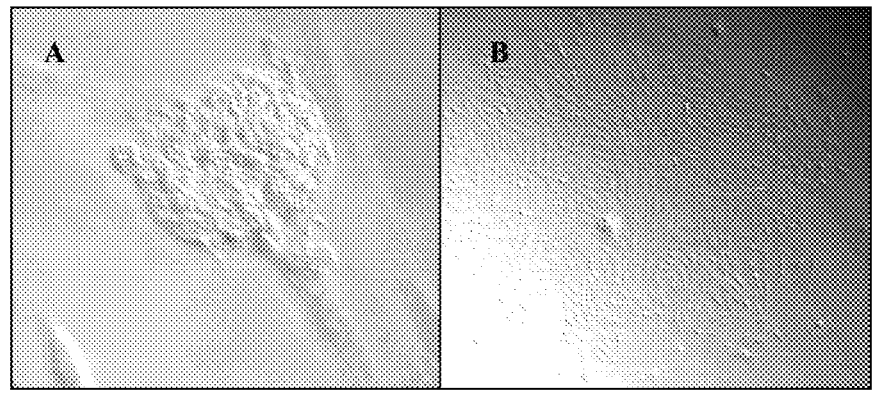
FIG. 3 is a micrograph; (A) is at 200× magnification, (B) is at 40× magnification.

FIG. 3 shows the colony-forming ability of the cells in the material isolated from first trimester human umbilical cord. Cells at earlier passages had a higher frequency of colony-formation as shown in FIG. 3. Part A of FIG. 3 shows said cells at the third passage (200× magnification), while Part B of FIG. 3 shows said cells at the $7^{th}$ passage (40× magnification).

Figure 4:
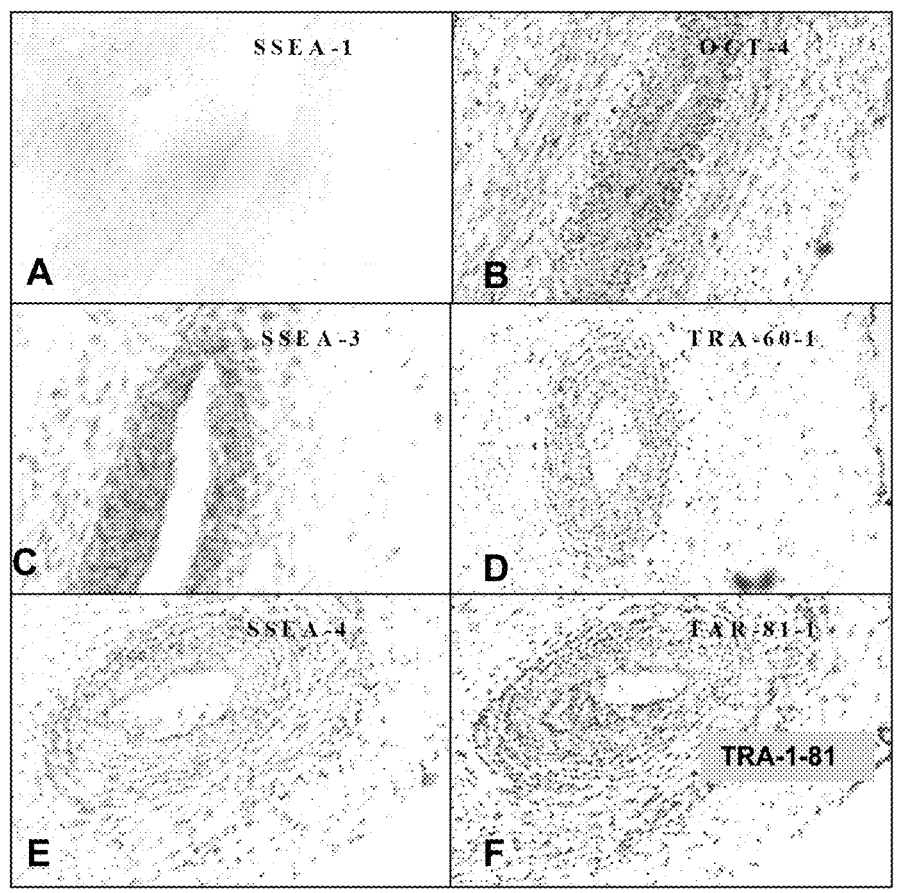
FIG. 4 is a micrograph showing immunohistochemical staining.

FIG. 4 shows the immunohistochemical (IHC) detection of early embryonic stem cell markers on the cells of first trimester human umbilical cord. IHC analysis revealed that the umbilical cord tissue was positive for TRA-1-60 (part D), TRA-1-81 (part F), SSEA-3 (part C), SSEA-4 (part E) and Oct-4 (part B), but not SSEA-1 (part A). This positive staining was mainly located in the perivascular cell population. This demonstrates that these cells have embryonic stem cell-like properties and derive mainly from the perivascular cell population. This appears to suggest that the markers are characteristic of embryonic stem cells. However, tumor cells that de-differentiate may express some of these markers. They are markers present on embryonic stem cells indicating that they could have the potential for pluripotential differentiation.

Figure 5:
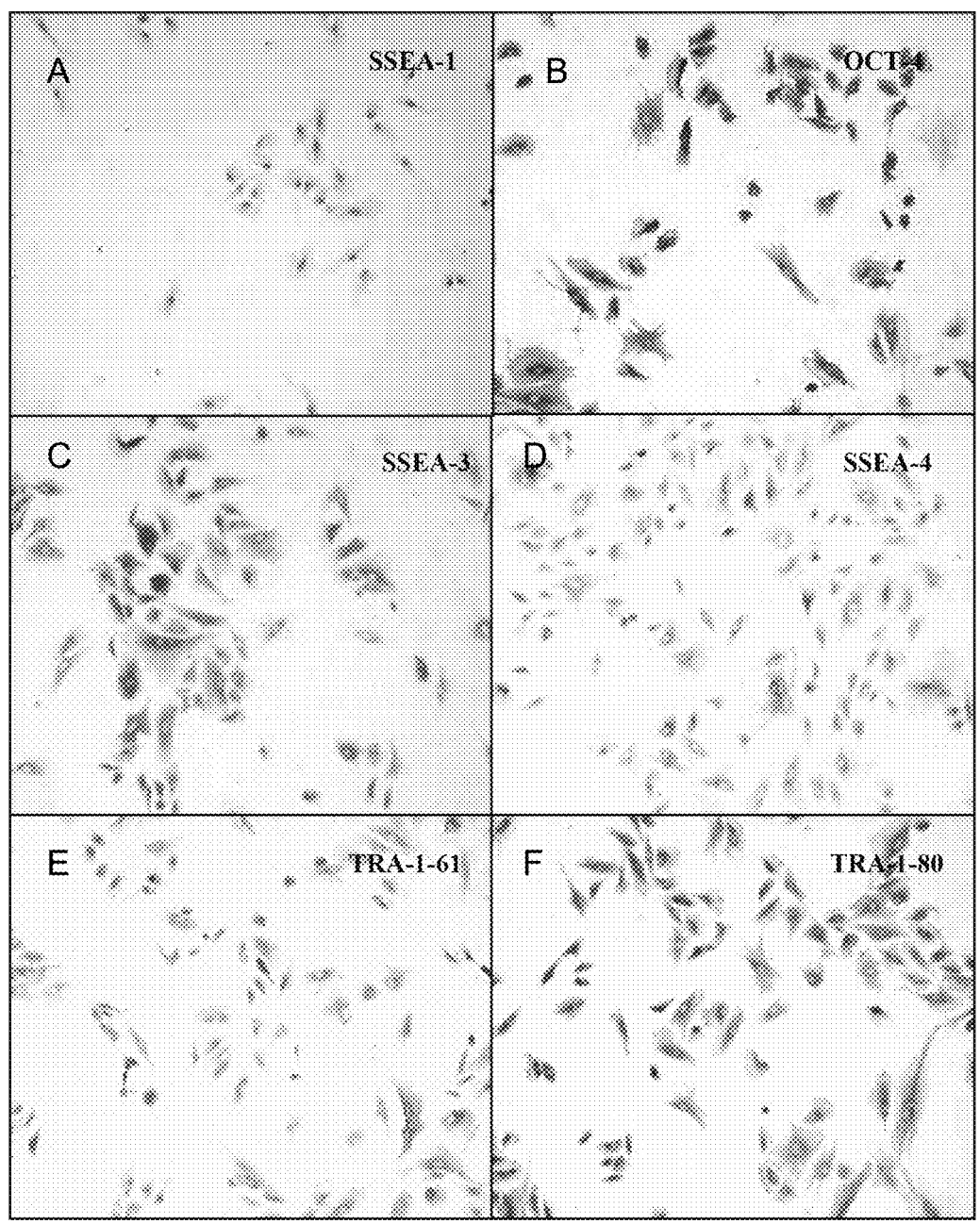
FIG. 5 is a micrograph showing immunocytochemical staining.

FIG. 5 shows the immunocytochemical detection of early embryonic stem cell markers on the $7^{th}$ passage of cells in the material isolated from first trimester human umbilical cord. This detection reveals the same markers as those found in the immunohistochemical analysis of the umbilical cord. Expression of these embryonic stem cell markers was consistent from passage 0 to 16, over 11 weeks of culture. Markers: SSEA-1 (part A), OCT-4 (part B), SSEA-3 (part C), SSEA-4 (part D), TRA-1-61 (part E), and TRA-1-80 (part F).

Figure 6:
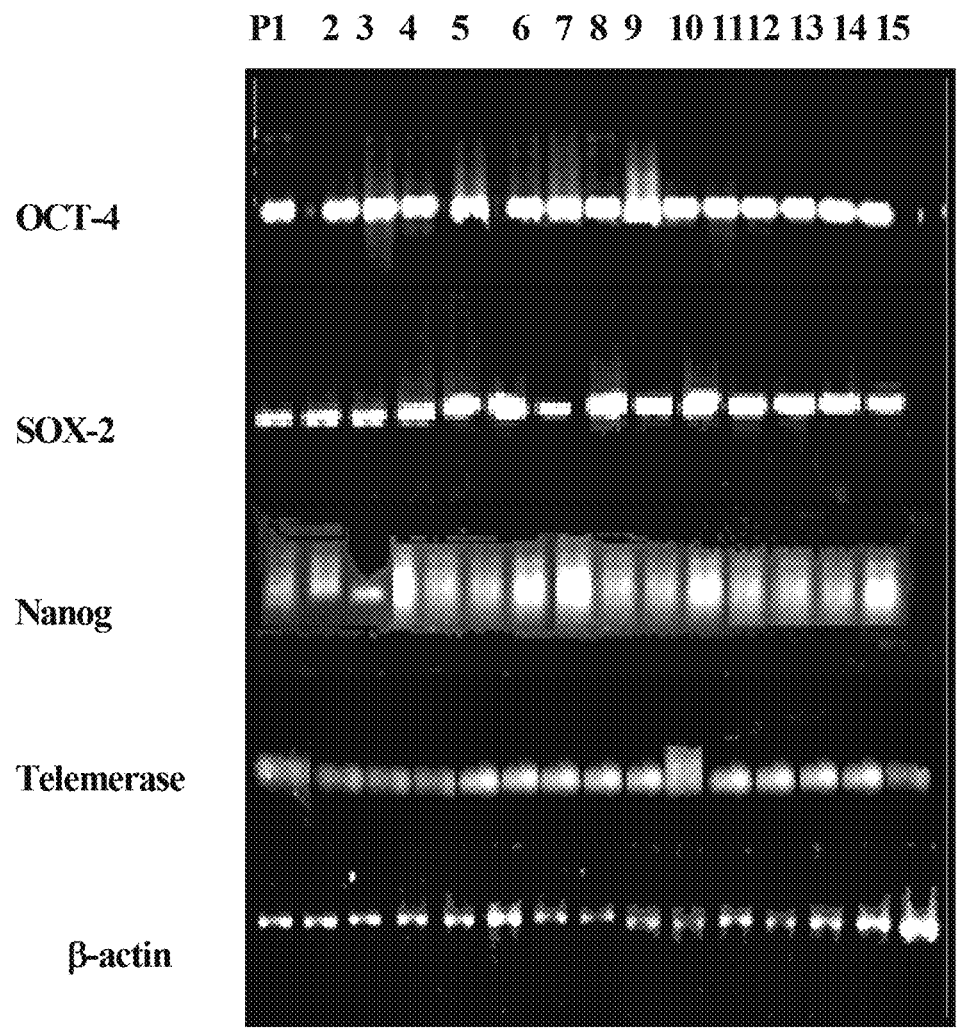
FIG. 6 depicts the results from an RT-PCR assay.

FIG. 6 shows the expression of OCT-4, SOX-2, Nanog and Telemerase transcripts by cells, from passages 1 to 15, in the material isolated from first trimester human umbilical cord. FIG. 6 shows that the cells retain expression of these early stem cell markers, and thus retain embryonic stem cell-like properties, for numerous passages in routine culture conditions without showing signs of spontaneous differentiation.

The presence of early embryonic stem markers, along with characteristics such as colony-forming ability, may indicate that material isolated from first trimester umbilical cord cells have embryonic stem cell-like properties. The data provided herein describe immunohistochemical staining that shows the isolated human umbilical cord cells are derived mainly from the perivascular cell population. In addition, the data illustrates the possibility of cryogenic storage and expansion of the isolated human umbilical cord cells, which can be kept undifferentiated in culture. The human umbilical cords isolated from first trimester terminated pregnancies, therefore, have the potential to be a large, and readily obtained source of stem cells. Advantageously, the method described herein does not utilize non-human based feeder layers.

Example 2

Differentiation of First Trimester HUCPV Cells in vitro and Expression of Tissue-Specific Markers.

Stem cells were isolated and expanded from the first trimester human umbilical cord (HUCPV), demonstrating that the cells have embryonic stem cell characteristics. These cells can express embryonic stem cell markers from passage 0 to 16 and have the ability to self-renew.

First trimester HUCPV cells were differentiated in vitro and examined for the expression of tissue-specific markers in the differentiated cells.

Methods

Perivascular cells were isolated from first trimester umbilical cords and were expanded in α-MEM containing 5-10% of FCS. These cells were grown in a suspension to induce their differentiation into EBs. EBs were transferred onto coated plates and cultured under appropriate condition. Morphology change was examined in these differentiation conditions. Dispersed EBs and differentiated cells were characterized using immunocytochemistry (ICC). RT-PCR assays were used to detect the presence of several tissue-specific molecular markers.

Results

Figure 7:
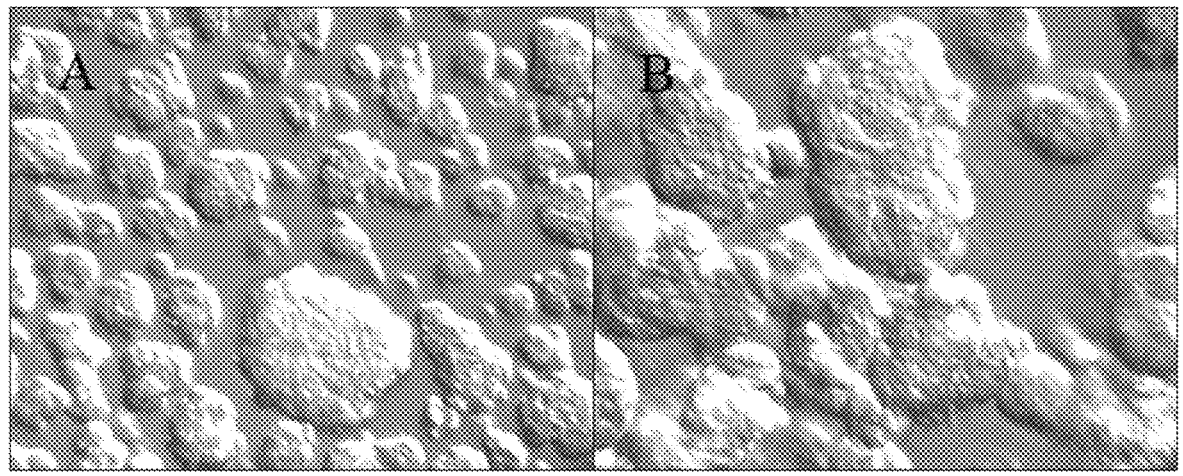
FIG. 7 shows EBs in suspension; (A) Magnification 200×; (B) Magnification 400×.

FIG. 7 shows that first trimester HUCPV cells have the ability to form EBs in a suspension culture condition. EBs in suspension may appear individually or as aggregates. (A) shows magnification 200×; and (B) shows magnification 400×.

Figure 8:
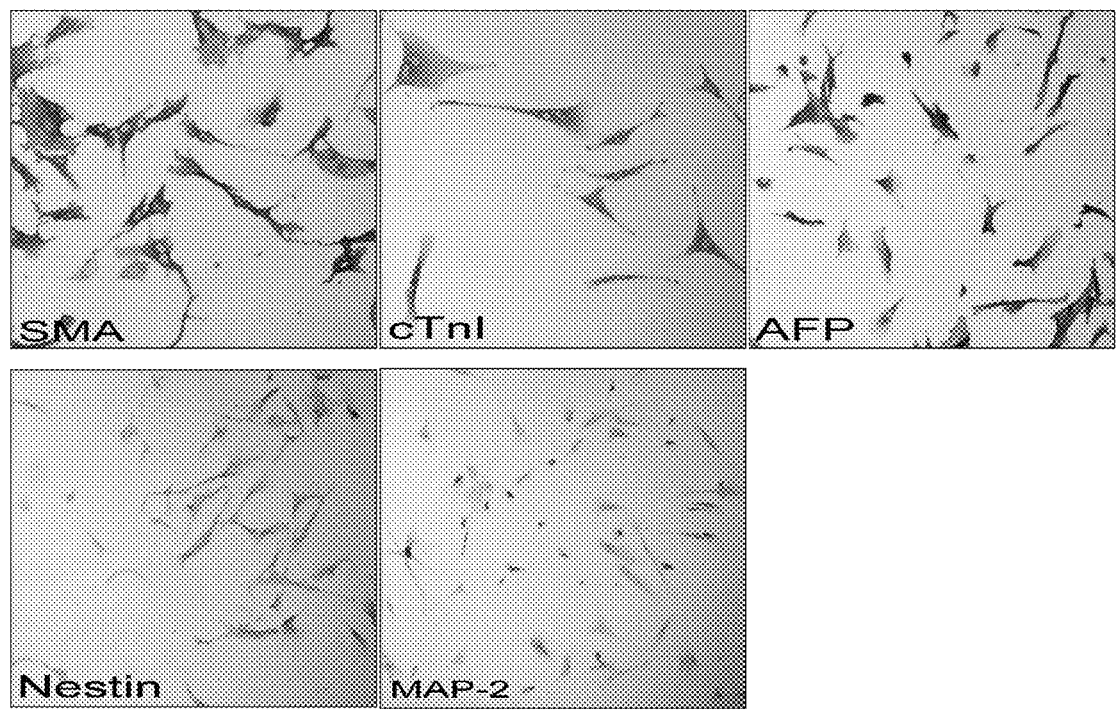
FIG. 8 illustrates immunocytochemistry to identify enzymatically dispersed EBs expression human embryonic germ layers characterization markers.

FIG. 8 shows that EBs can express protein markers characteristic of mesoderm (SMA and cTnI), endoderm (AFP), and ectoderm (nestin, MAP-2). FIG. 8 illustrates immunocytochemistry to identify enzymatically dispersed EBs expression human embryonic germ layers characterization markers.

Figure 9:
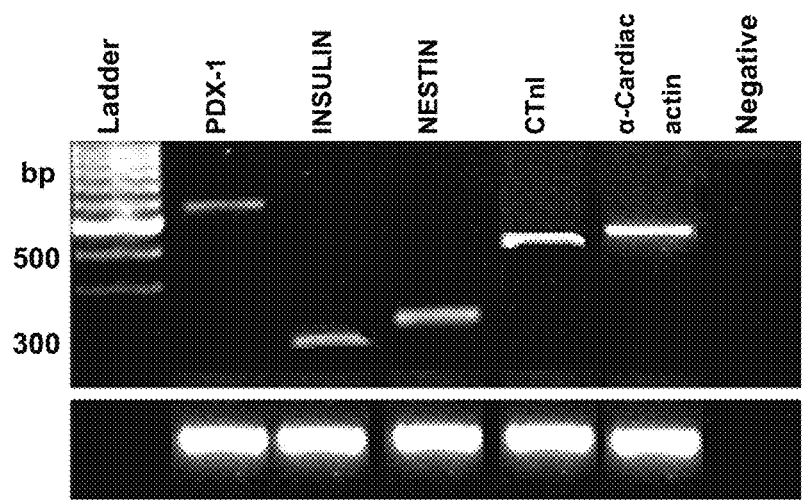
FIG. 9 shows expression of differentiation markers in embryo body (EB) by RT-PCR.

FIG. 9 shows expression of differentiation markers in embryo body (EB) by RT-PCR. This demonstrates the expression of three germ layer markers: PDX-1, insulin, nestin, cTnI and α-cardiac actin.

Figure 10:
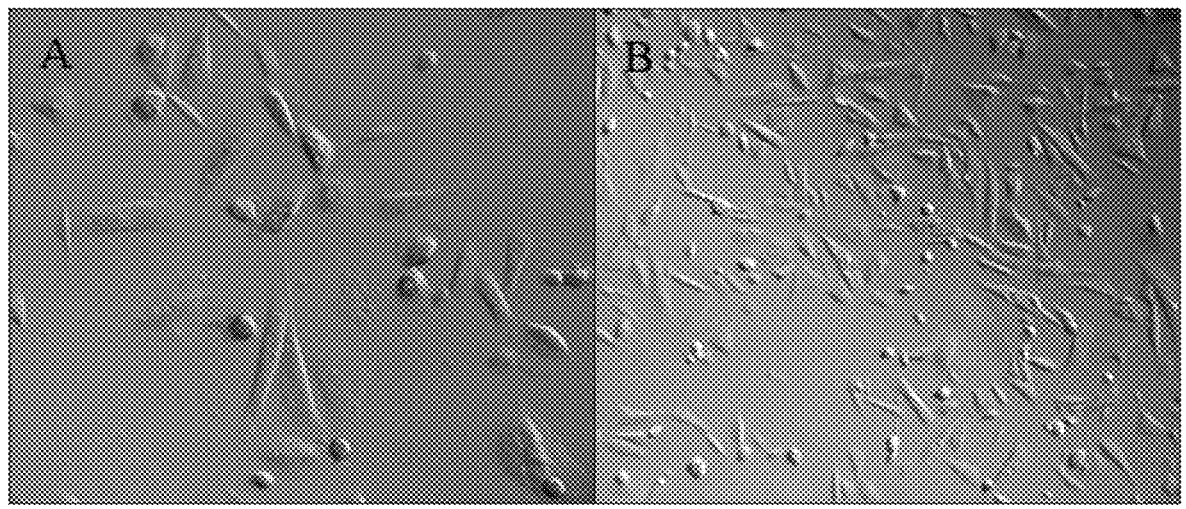
FIG. 10 shows HUCPVC differentiation to cardiomyocyte-like cells. (A) Magnification 100×; (B) Magnification 40×.

FIG. 10 shows that HUCPV cells have morphology change in cardiomyocytes culture condition. (A) shows magnification 100×; and (B) shows magnification 40×.

Figure 11:
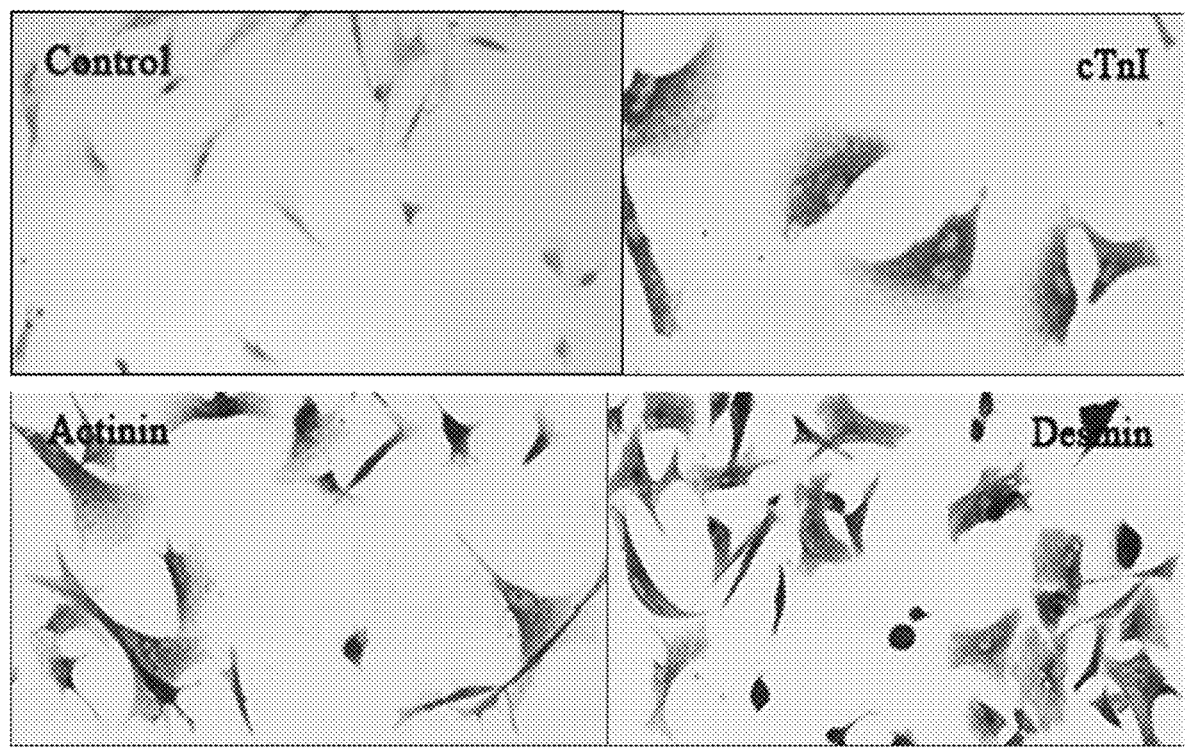
FIG. 11 shows immunocytochemical detection of mesoderm markers on HUCPVC differentiation into cardiomyocytes.

FIG. 11 shows immunocytochemical detection of mesoderm markers on HUCPVC differentiation into cardiomyocytes. Positive immunostaining was identified for cTnI, actin, and desmin.

FIGS. 9 to 11 show that cell morphology changed under differentiation culture conditions.

Figure 12A:
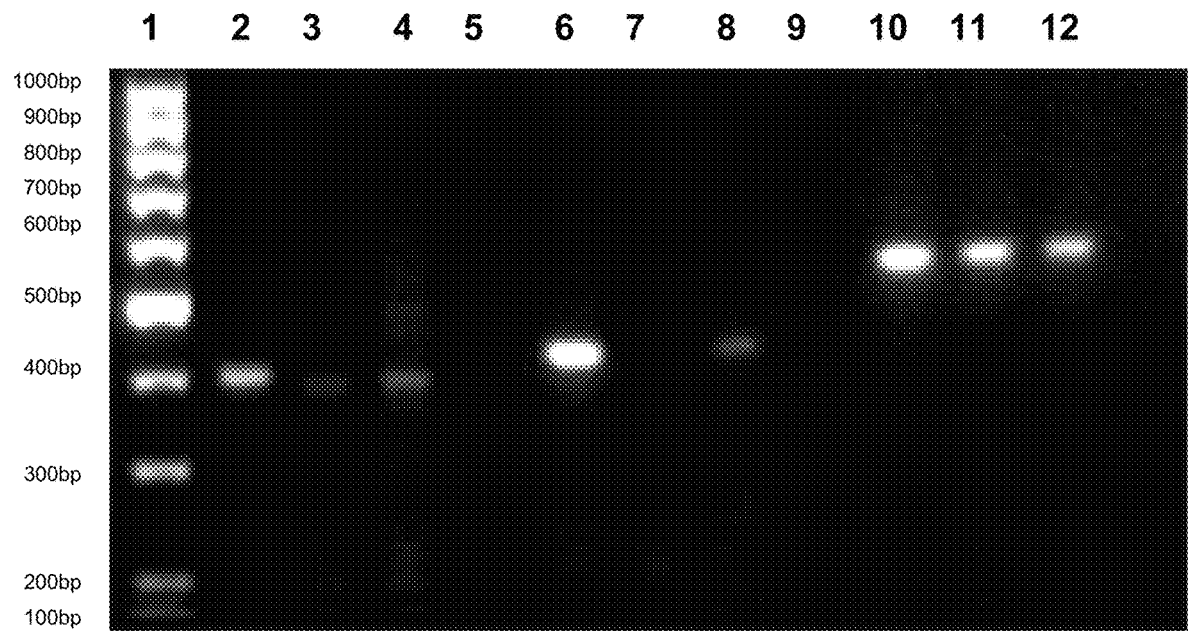
FIG. 12A shows RT-PCR analysis of first-trimester HUCPV cells expression cardiomyocyte marker genes after in vitro differentiation into cardiomyocytes. Differentiated cells express cTnI (lane 2, 416 bp) and alpha-cardiac actin (lane 6, 418 bp).
Figure 12B:
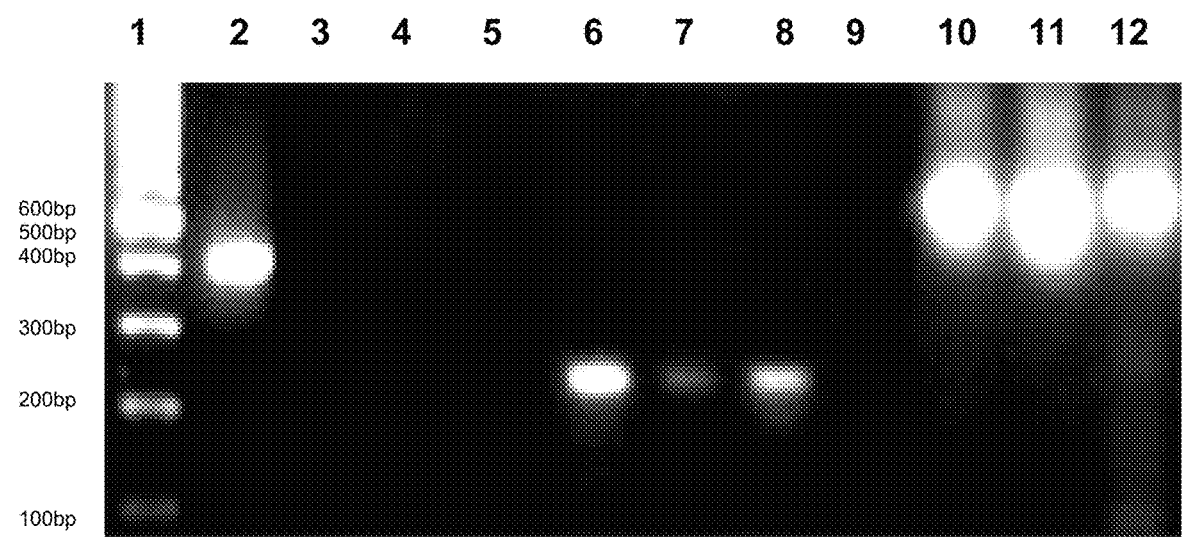
FIG. 12B shows RT-PCR analysis of first-trimester HUCPV cells expression cardiomyocyte marker genes after in vitro differentiation into cardiomyocytes, wherein differentiated cells express desmin (lane 2, 408 bp) and beta-myosin heavy chain (lane 6, 205 bp).

FIG. 12A shows RT-PCR analysis of first-trimester HUCPV cells expression cardiomyocyte marker genes after in vitro differentiation into cardiomyocytes. FIG. 12A shows differentiated cells express cTnI (lane 2, 416 bp) and alpha-cardiac actin (lane 6, 418 bp). FIG. 12B shows that differentiated cells express desmin (lane 2, 408 bp) and beta-myosin heavy chain (lane 6, 205 bp).

Figure 13:
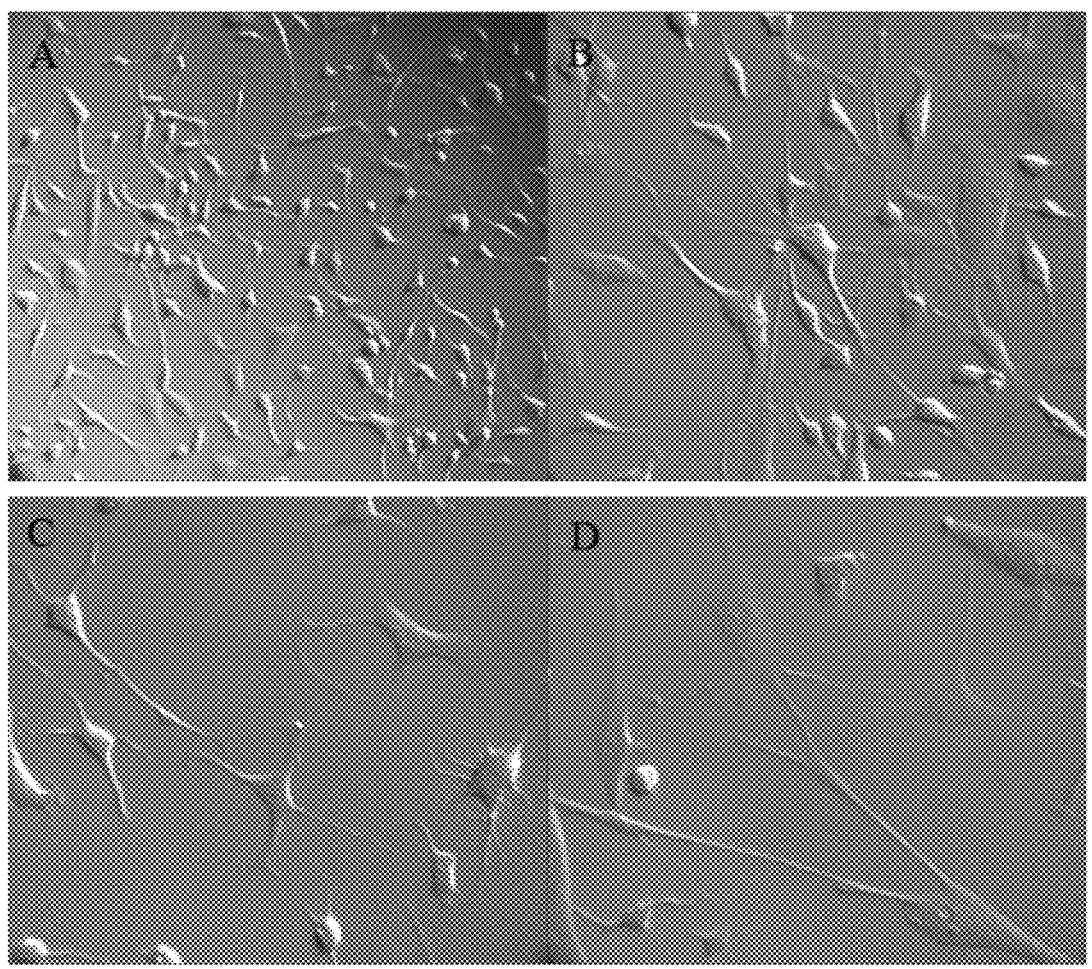
FIG. 13 shows cell morphology changes after HUCPVC cells were differentiated into nerve-like cells. (A): magnification 40×; (B) and (C): magnification 100×; and (D): magnification 200×.

FIG. 13 shows that nerve-like cells can be observed under neural culture conditions. (A) shows magnification 40×; (B) and (C) show magnification 100×; and (D) shows magnification 200×.

Figure 14:
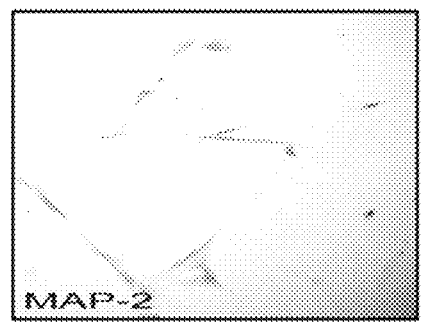
FIG. 14 shows immunocytochemical detection of ectoderm markers on HUCPVC differentiation into nerve-like cells. (A) MAP-2; (B) MBP; (C) beta-tubulin; and (D) nestin.
Figure 14:
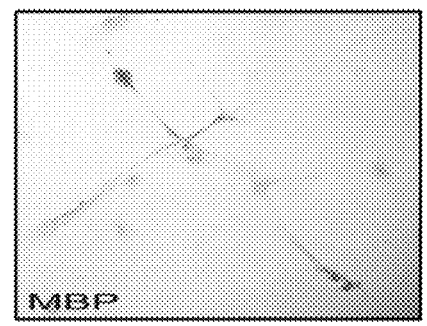
Figure 14:
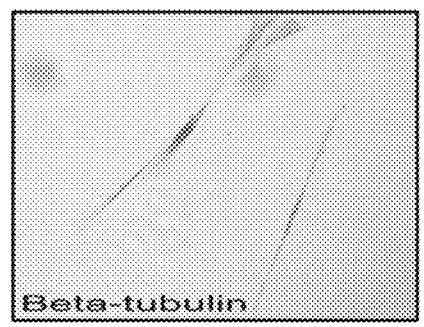
Figure 14:
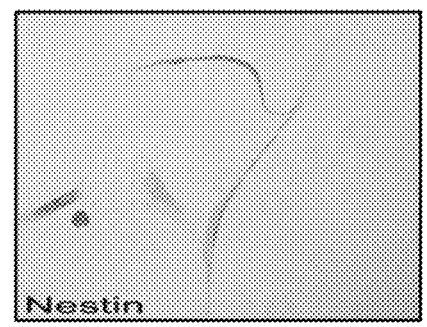

FIG. 14 shows nerve-like cells identified by ICC analysis using neural marker MAP-2, MBP, nestin and R-tubulin. This shows immunocytochemical detection of ectoderm markers on HUCPVC differentiation into nerve-like cells. (A) shows MAP-2; (B) shows MBP; (C) shows beta-tubulin; and (D) shows nestin.

Figure 15:
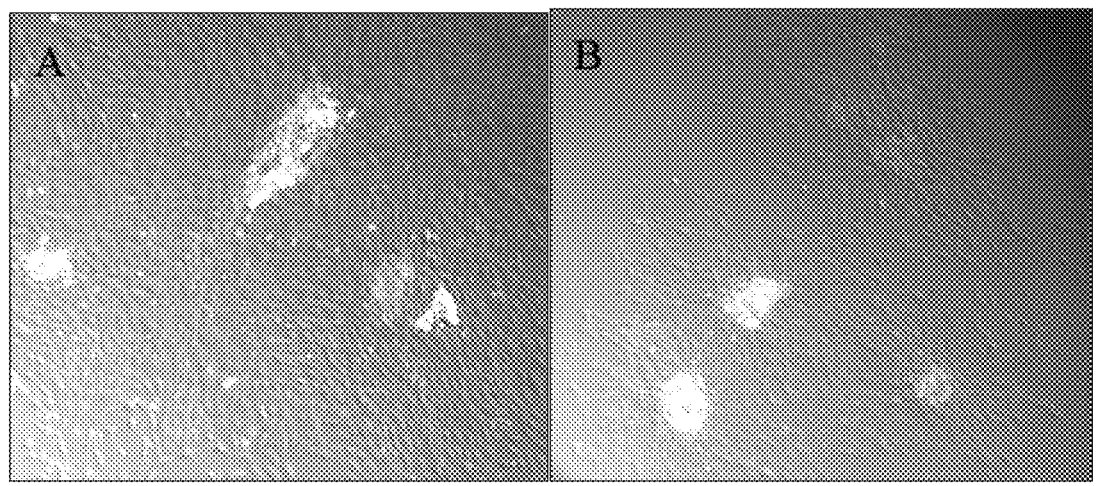
FIG. 15 shows morphologic changes observed in pancreatic differentiation stage. In part (A) (Step 2, Enrichment of Nestin Positive Cells) EBs have attached to the tissue culture dish and have differentiated into pancreatic-like cells. Part (B) (Step 3, Differentiation to Insulin-Secreting Pancreatic Islet-like Clusters) shows high density in central pancreatic-like cells.

FIG. 15. shows that morphologic changes were observed in pancreatic differentiation stage. In FIG. 15A (Step 2, Enrichment of Nestin Positive Cells), EBs have attached to the tissue culture dish and have differentiated into pancreatic-like cells. In FIG. 15B (Step 3, Differentiation to Insulin-Secreting Pancreatic Islet-like Clusters), high density in central pancreatic-like cells. During this differentiation stage, islets have a three-dimensional topology.

Figure 16:
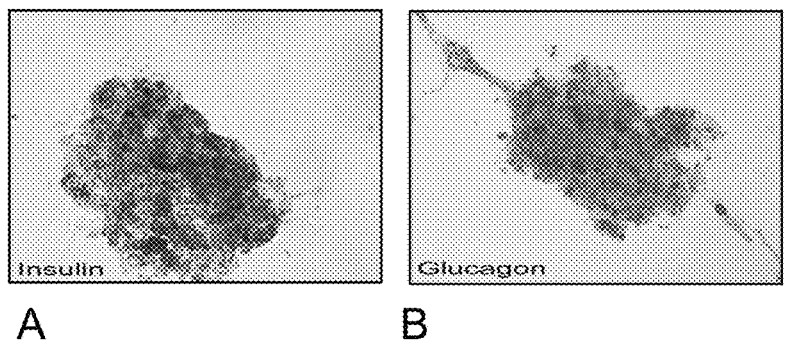
FIG. 16 shows immunocytochemical staining of HUCPVC-derived islet clusters with pancreatic markers in the presence of (A) insulin; and (B) glucagon.

FIG. 16 shows immunocytochemical staining of HUCPVC-derived islet clusters with pancreatic markers. The islet-like clusters can be stained with insulin (A) and glucagon (B).

Figure 17:
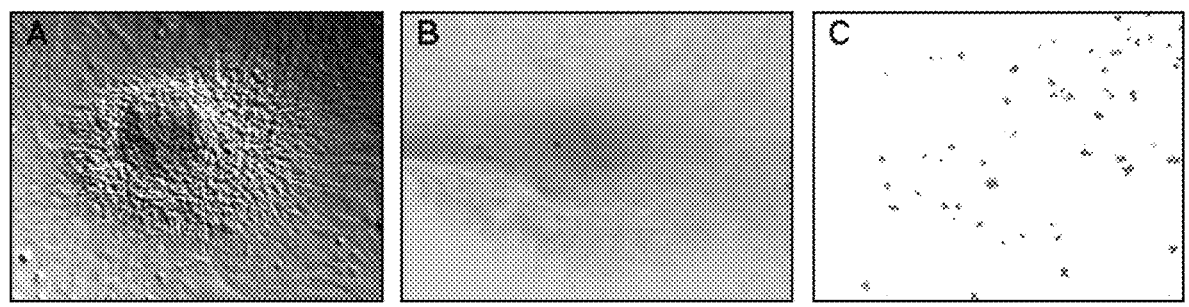
FIG. 17 shows that HUCPV cells can differentiate into osteogenic and adipogenic lineages. In (A), cells appear polygonal (osteoblasts) under the culture condition of osteogenic differentiation. In (B), cells were stained with Alizarin Red S. In (C), cells were stained with Oil Red O after cultured with adipogenic complete medium.

FIG. 17 shows that HUCPV cells can differentiate into osteogenic and adipogenic lineages. These differentiations can be detected by Alizarin Red S and Oil Red O staining. In (A), cells appear polygonal (osteoblasts) under the culture condition of osteogenic differentiation. In (B), cells were stained with Alizarin Red S. In (C), cells were stained with Oil Red O after cultured with adipogenic complete medium.

The above results show that cells derived from human first trimester umbilical cords represent an embryonic-like stem cell population with the capacity to form EBs in vitro. Further, the results show that the cells also have the capacity to differentiate into a wide variety of cell types that include derivatives of all three embryonic germ layers.

Example 3

Use of Early Intravenous First Trimester Human Umbilical Cord Cells in Spinal Cord Injury Summary This Example shows that early intravenous first trimester human umbilical cord-perivascular cell delivery after traumatic spinal cord injury significantly improves forelimb motor function and promotes weight gain. Localized vascular disruption as a result of spinal cord injury (SCI) triggers a cascade of secondary events, including inflammation, reactive gliosis and scarring that influence recovery. In addition to immunomodulatory and pathotropic properties, mesenchymal stromal cells (MSCs), including human umbilical cord matrix cells (HUCMCs), possess pericytic features. This makes MSCs ideally suited to targeting acute vascular disruption, which could reduce the severity of secondary injury, enhance tissue preservation and repair, and promote chronic functional recovery. Here, intravenous tail vein infusion of HUCMCs, first trimester human umbilical cord perivascular cells (FTM-HUCPVCs), adult bone marrow mesenchymal stem cells (BMSCs) and HBSS+2 mM EDTA (HE) control was performed 1 hour post-SCI followed by weekly behavioral testing. Rats were sacrificed 10 weeks post-SCI and immunohistochemistry was employed following perfusion and tissue fixation. Very high resolution ultrasound was used to measure lesional cavitation in live animals. At sacrifice, FTM HUCPVC-infused rats displayed the greatest improvement in grip strength (p<0.05 vs HE). As well, only FTM HUCPVC-infusion led to significant weight gain.

All cell infusion treatments resulted in reduced glial scarring ($p<0.05$ vs HE). Whilst percent cavitation was reduced with cell infusion, this was not significant. Unlike BMSCs, FTM HUC PVC- and term HUCMC-infusion led to increased axonal (NF200 antibody), myelin (FluoroMyelin stain), and vascular (LEA stain) densities ($p<0.05$ vs HE). Selective chronic functional recovery was demonstrated alongside histological improvements with acute umbilical cord-derived MSC infusion, most dramatically with FTM-HUCPVCs, in a clinically-pertinent model of cervical SCI. These findings highlight the potential of these cells, isolated according to the method described herein, for early therapeutic intervention in SCI.

In data provided and described herein, it is shown that early intravenous human umbilical cord-derived cell infusion in a clinically relevant model of SCI leads to long-term histological benefits including enhanced vascularisation, myelination and axonal density, reduced glial scarring and cavitation. Of the cells types tested, infusion of FTM-HUCPVCs resulted in the most significant selective functional benefits; specifically improved grip strength and body weight. This is the first study to compare MSCs derived from different donor ages and sources, and the first to identify similarities and differences between their efficacies on several chronic histological and functional parameters after traumatic SCI. Very high resolution ultrasound was used to accurately measure lesional cavitation in live animals. This minimally invasive and effective approach to cell therapy has significant translational implications to the acute treatment of traumatic SCI and other CNS injuries for the purposes of sustained benefit.

Material & Methods

Experimental Design. Passage-matched (passage 6 to 7) FTM HUCPVCs, term HUCMCs, adult BMSCs, new-born fibroblasts cultured under identical conditions were compared as detailed below. Animals were randomly assigned to a treatment group (10 per condition/treatment) and given a coded designation until data acquisition and processing was complete. Rats were sacrificed 4 or 10 weeks post-SCI.

Animal Use. All experiments involving animal use were approved by the University Health Network Animal Care Committee (Animal Use Protocol #979), in Toronto, Canada.

Tissue Procurement & Cell Isolation. Two to three centimeters of term umbilical cord was purchased from LifeLine Stem Cells (New Haven, Indiana, USA), and dissected in sterile Hank's Buffered Saline (HBSS, Gibco, Canada) containing 1% gentamycin using aseptic technique. The vein and arteries were carefully removed. Pieces of Wharton's jelly (umbilical cord matrix) were then transferred to collagenase I and II (1 mg/ml, Gibco, Canada), diced into small pieces and incubated for up to 2 hours at 37° C. on an orbital shaker before adding Ca2+ and $Mg^{2+}$-free Phosphate-Buffered Saline (PBS, Gibco, Canada) to the viscous cell suspension, followed by trituration, and centrifugation at 2000 rpm for 10 minutes at room temperature.

FTM HUCPVCs were isolated as described herein from Create Fertility Centre (University of Toronto, Toronto, Canada). Other cell types used included passage-matched adult human bone marrow stromal cells (BMSCs, Lonza) and newborn (CRL-2703, ATCC) human fibroblasts. Identical culture conditions were used for all cell types and sources.

Cell Culture. Cells were seeded into uncoated tissue culture T175 flasks (Greiner, Canada) in Alpha-MEM (Gibco, Canada) containing 10% batch-tested foetal bovine serum (FBS, HyClone, USA Lot #KTJ32091), 1% sodium pyruvate, 1% Glutamax and 0.1% gentamycin (Sigma-Aldrich, Canada) (complete medium). This culture was referred to as passage 1 (p #1). After 2 to 5 days, the non-adherent HUCMCs were discarded. Fresh complete medium was added to the original dish (p #1) and the adherent cells were grown to a maximum 70-80% confluence before passaging, harvesting for infusion or cryogenic storage. The medium was completely replaced twice a week.

Sub-confluent passage number 6-7 cultures were passaged at no more than 70-80% confluence using trypsin-like enzyme (TLE, Sigma-Aldrich, Canada). The cells were resuspended in 1 ml fresh medium and dissociated by gentle trituration. After passing the cell suspension through a 70 μm filter to remove any clumps, total cell counts and viabilities were determined haemocytometrically using the Trypan blue dye (Sigma-Aldrich, UK) exclusion assay. Cells were reseeded into fresh uncoated 140 mm tissue culture dishes (Greiner, Canada) at $5 \times 10^5$ cells per 20 ml. In order to prevent re-aggregation prior to infusion, cells were instead re-suspended in Hank's buffer containing 2 mM EDTA and were kept on ice for no more than 2 hours after dissociation.

SCI Model and Cell Infusion. All surgeries were performed by the same person (referenced herein as: RV). Young adult female Wistar rats (250-300 g) received a C7 35 g clip compression SCI for one minute under Isoflurane anaesthesia with a 1:1 mixture of O2/NO2 (1 L/min). Then 2.5 million cells were systematically infused in 1 ml Hank's buffer/2 mM EDTA (to prevent re-aggregation prior to infusion) via the tail vein 1 hour post-SCI, which translates into a realistic timeframe of acute intervention of a few hours in a patient. Cells were kept on ice for no more than 2 hours after dissociation. Infusion via the tail vein was performed manually but over a duration of no less than 5 minutes. Increasing the cell number and/or infusion any sooner was associated with a higher rate of mortality occurring immediately after cell infusion. Specialised post-operative husbandry protocols were followed by qualified and experienced personnel (also blinded to treatment conditions) to maximise animal welfare. These included corn cob (1¼") and Isopad™ bedding, Clavamox-supplemented drinking water and Bacon Softies diet (starting immediately postop). Animals were caged singly post-operatively with Nylabone™ and kept on a 12-hour light/dark cycle at all times. Bladder squeezing (three times a day), cyclosporine (Sandimmune) injections (10 mg/kg s.c. once daily) and Buprenorphine injections (0.05 mg/kg s.c. twice daily) were performed at regular times.

Careful consideration was given to approved standards of reporting for all procedures and data described.

Lesional Spinal Cord Cavitation & Neuroanatomical Assessment with Very High Resolution Ultrasound (Vhrus) and Unbiased Cavalieri estimation. The injured spinal cord was assessed by pre-sacrificial echography with very high-resolution ultrasound (VHRUS) with a 44 MHz probe (Vevo 770, VisualSonics, Toronto, Canada). Three-dimensional (3D) VHRUS acquisitions were made in B-mode. The 3D files were analysed with ImageJ software with minor modifications. Instead of using a set region of interest (ROI), the bright pixel lesions were delineated by three independent blinded observers within a 15 sagittal image slice, 102 μm thick stack to generate a reproducible cavity volume.

Histology. Spinal cords were isolated from rats perfused with 250 ml chilled PBS (without $Ca^{2+}$ and $Mg^{2+}$) followed by 50 ml of chilled 4% paraformaldehyde (PFA). Spinal cords were then post-fixed in 4% PFA overnight at 4° C. before transfer to 30% sucrose (at 4° C.) and storage in OCT (at 4° C. for 1-2 days then −20° C.) until embedding in fresh OCT and cryosectioning (20 μm thick cross-sections). The delay between spinal cord isolation and cryosectioning was minimised as much as possible. To assess vascularity, endothelial cells were labelled with a DyLight 594-conjugated tomato lectin from *Lycopersicon esculentum* agglutinin (LEA, VectorLabs DL-1177, 1:300). Myelination and axonal density were quantified using FluoroMyelin (Molecular Probes F34651; 1:100) and anti-NF200 (Sigma N0142, 1:200), respectively. Gliosis and glial scarring were quantified using anti-GFAP (Millipore AB5541, 1:200) and anti-CSPG (Clone CS-56, Sigma C8035, 1:200) antibodies, respectively. All appropriate goat secondary antibodies (Alexa Fluor) were used at a 1:200 dilution.

Slides were baked for 15 minutes at 55° C. so cryosections would adhere permanently to the slides. After blocking in PBS (without $Ca^{2+}$ and $Mg^{2+}$)+2% FBS+0.1% Triton-X for 1 hour at room temperature, primary antibodies diluted in the same diluent solution were applied overnight at 4° C. After 3 washes in PBS, secondary antibodies (1:200 dilution) were applied as necessary. Hoechst 33242 was used as nuclear counterstain. Slides were mounted in Mowiol after 5 PBS washes. Negative staining controls (primary or secondary antibody alone) were used to assess baseline image acquisition parameters. The latter were kept consistent for each fluorescent channel between slides and treatment conditions. All staining was done in one batch and the delay between mounting slides and image acquisition was kept to a minimum.

Unbiased Cavalieri Estimation of cavitation, tissue sparing and grey:white matter ratio was carried out on StereoInvestigator software on a Nikon Eclipse E800 microscope on longitudinal cryosections slides.

Image acquisition & Processing Protocol. Images were acquired at ×200 magnification. From 3 sections per rat, various view fields spanning a minimum of 5 mm rostrocaudal to the injury site were stitched automatically post-acquisition by the StereoInvestigator software on a Nikon Eclipse E800 microscope. Images were then thresholded (based on negative control slides) and binarised, and the area of fluorescent staining was determined as a proportion of the total area (kept fixed) of the lesional and peri-lesional spinal cord corresponding to 5 mm of tissue. Any cavity was excluded during this measurement. Cavitation was expressed as a proportion of the total volume of spinal cord corresponding to 6 mm of lesional and peri-lesional tissue, which equates to the acquisition viewfield of VHRUS.

Statistical Analyses. Statistical analyses were performed with GraphPad Prism software (La Jolla, CA, USA). Unless otherwise stated, One-Way ANOVAs and Bonferroni's multiple comparisons test were performed, with the Alpha threshold set to 0.05. Standard errors of means were compared using the Brown-Forsythe test.

Results

Figure 18:
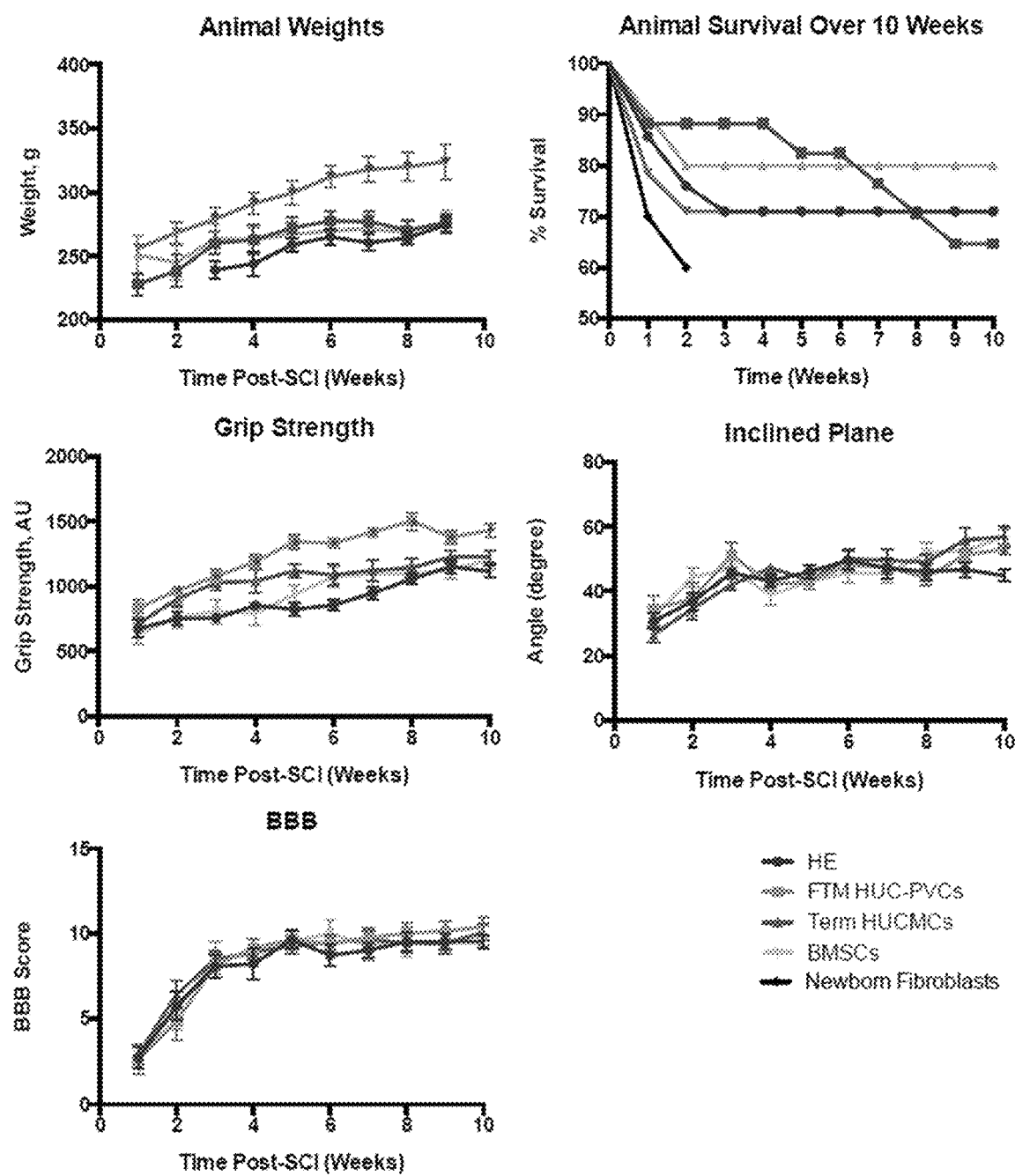
FIG. 18 shows animal survival, weight and functional readouts over 10 weeks post-SCI.

Functional Readouts. The antigenic profiles of the cells employed in this study were evaluated. A battery of standard weekly functional tests starting one week post-SCI (FIG. 18). All animals started off within the same weight range (250-270 g) at week 0. No animals showed any overt signs of infection that might impede weight gain. Rats treated with FTM HUCPVCs exclusively gained weight more than rats receiving other cells acutely and were at a higher pre-sacrificial weight than rats receiving other treatments. The significant weight gain demonstrated by the term HUCMC- and FTM HUCPVC-infused rats over HE-infused controls was not reflected in other functional readouts at the same time points, except for grip strength.

FIG. 18 shows animal survival, weight and functional readouts over 10 weeks post-SCI (1 minute C7 compression). Multiple t-tests with Sidak-Bonferroni correction (HE n=14, Term HUCMCs n=11, FTM HUC PVCs n=8, BMSCs n=8, * p<0.05).

The grip strengths of FTM HUC PVC-infused rats were significantly greater than term HUCMCs from 5 to 10 weeks post-SCI. The two grey asterisks at 2 and 4 weeks post-SCI represent term HUCMCs vs HE p=0.0504 and 0.0514 respectively. Rats treated with FTM HUCPVCs exclusively performed significantly better from 3 weeks post-SCI onwards compared to rats receiving HE vehicle acutely.

No significant differences in inclined plane (combined right and left) were detected between conditions at 1-8 weeks post-SCI, but term HUCMC-infused rats performed better than HE-infused controls at 9 and 10 weeks post-SCI (term HUCMC vs HE p=0.0394 and 0.0042, respectively) and all cell-infused rats were better than HE controls at 10 weeks post-SCI (BMSC vs HE p=0.009, FTM HUCPVC vs HE p=0.0012).

No significant differences were detected between conditions and most animals levelled off at a BBB score (combined right and left) of 9-11.

Chronic Histology

Chronic Tissue Preservation. Next, tissue preservation was examined, specifically: cystic cavitation, tissue sparing, grey:white matter ratio and spinal cord diameter were evaluated. Cavitation was assessed by two complementary techniques—VHRUS immediately prior to sacrifice at 10 weeks and Cavalieri estimation on StereoInvestigator software after histological processing. These two techniques showed a statistically significant correlation (p=0.0472). Although trends of reduced cavitation with cell infusion were clear, no statistically significant effect of cell infusion was found on cavity volume relative to HE controls (term HUCMCs and BMSCs, p=0.5507 and 0.5558 vs HE, respectively). There was also no significant difference in percent cavitation between cell-infused rats. A similar trend of reduced percent cavitation with cell infusion (relative to HE-infused controls) was found when cavity volume was assessed post-sacrificially using unbiased stereological Cavalieri estimation. No other neuroanatomical parameter (tissue sparing, grey:white matter ratio and spinal cord diameter) indicated that tissue preservation was enhanced with cell infusion and no significant difference between conditions was found. The functional benefits of term HUCMC and FTM HUCPVC infusion were not reflected by higher grey:white matter ratio, tissue sparing or lesion site spinal cord diameter compared to controls or other cells.

Cavitation was assessed by Cavalieri estimation on StereoInvestigator software (after histological processing). VHRUS and Cavalieri estimation of cavitation showed a statistically significant correlation (data not shown here). Tissue sparing parameters were assessed by Cavalieri estimation on StereoInvestigator software (after histological processing. As expected, tissue sparing and spinal cord diameter (at the lesion site) showed the inverse trend to % cavitation. Stitch of Longitudinal section (20 μm thick) of Peri-Lesional Spinal Cord 10 weeks post-SCI taken at ×20 was evaluated at ×4 magnification. Slides were stained with LEA (endothelial cells/vasculature), FluoroMyelin or anti-NF200 (axons). All parameters were expressed as the proportion of the area within a 5 mm length of lesioned spinal cord (2.5 mm rostrocaudal to the lesion site) with positive staining.

Vascular density, Myelination & Axonal Density. Following sacrifice and isolation of the spinal cord, cryosections were stained for antigenic markers of vascular density (LEA), myelination (FluoroMyelin, FM) and axonal density (NF200). All parameters were expressed as the proportion of the area within a 5 mm length of lesioned spinal cord (2.5 mm rostrocaudal to the lesion site) with positive staining. Only term HUCMC and FTM HUCPVC infusion resulted in significantly higher vascularity, myelination and axonal density compared to HE-infused control rats at 10 weeks post-SCI. There was no significant difference between term HUCMC- and FTM HUCPVC-infused rats for any of these three histological parameters. Adult human BMSC infusion consistently resulted in higher values for these parameters than HE controls without reaching statistical significance. There was no significant difference between HE- and term HUCMC-infused rats at 4 weeks post-SCI for these markers, the only two conditions compared at this time point (data not shown). LEA (endothelial cells/vasculature), FluoroMyelin or anti-NF200 (axons) staining was evaluated at 4 weeks post-SCI. All parameters were expressed as the proportion of the area within a 5 mm length of lesioned spinal cord (2.5 mm rostrocaudal to the lesion site) with positive staining. p values were obtained through the Mann-Whitney test.

Glial Scarring. Antigenic markers of gliosis (GFAP) and glial scarring (CSPG) were examined. Both parameters were expressed as the proportion of the area within a 5 mm length of lesioned spinal cord (2.5 mm rostrocaudal to the lesion site) with positive staining. Infusion of all three cells resulted in significantly lower glial scarring compared to HE-infused control rats. There was no significant difference between term HUCMC-, FTM HUCPVC- and BMSC-infused rats (data not shown). There was no significant difference between HE- and term HUCMC-infused rats at 4 weeks post-SCI for these markers. Stitch of Longitudinal section (20 µm thick) of Peri-Lesional Spinal Cord was evaluated 10 weeks post-SCI taken at ×20 Slides were stained with anti-GFAP (astrocytes/gliosis) and anti-CSPG (glial scar). All parameters were expressed as the proportion of the area within a 5 mm length of lesioned spinal cord (2.5 mm rostrocaudal to the lesion site) with positive staining.

Bladder Size. Bladder size has been correlated with functional performance. Despite the higher than control grip strength and body weight in term HUCMC- and FTM HUCPVC-infused rats, bladder size in this study was no different from controls and rats receiving other cells. Bladder sizes at 10 weeks post-SCI. No significant difference was found between conditions.

Discussion

In this Example, only rats infused with FTM HUCPVCs gained weight significantly more than controls and those receiving other cells over 10 weeks post-SCI. This was also reflected in better grip strength performance after FTM HUCPVC infusion from 2 to 10 weeks post SCI, but not other functional readouts. Inclined plane performance was slightly improved relative to HE controls only at 10 weeks post-SCI and only in rats receiving cell infusions. BBB scores levelled off at 9-10 by 5 weeks post-SCI and no difference was found between conditions. It was found that early systemic infusion of human umbilical cord MSCs, but not adult human BMSCs, significantly promotes vascular density, myelination and axonal density. It was also found that glial scarring is significantly reduced irrespective of which cells are infused. Other neuroanatomical parameters (cystic cavitation, tissue sparing, grey:white matter ratio and spinal cord diameter) and bladder size at 10 weeks post-SCI were not influenced by cell infusion.

The improved vascular density, myelination and axonal density could be a consequence of acute tissue preservation or enhanced repair, or both. There might be a threshold that needs to be achieved, alongside a sufficient reduction of glial scarring in order for functional benefits to become apparent. The absence of infused cells at or near the lesion site (data not shown) suggests the infused cells achieve their benefit through the provision of trophic support The most effective cell administration route for the integration of donor cells within and near the lesion site is still debated, even though the invasiveness of intra-parenchymal cell injection is well recognised, as well as the challenge this poses to the application of cell therapy especially during the acute phase of injury. However, the benefits of intravenous cell administration are clear from this Example.

Although not yet a validated therapy for SCI, the safety of this approach has already been established through pre-clinical SCI studies, and its clinical application to other conditions affecting the CNS, including multiple sclerosis and bone marrow transplantations. Nevertheless, this approach is not without its limitations. Osteoblastic differentiation of infused MSCs has been reported within lung tumours and although this has not been observed in injury and degeneration models, this possibility should not be dismissed.

At 10 weeks post-SCI, two out of 15 (one sub-cutaneous) of the rats receiving term HUCMCs and two out of 10 rats receiving FTM HUCPVCs intravenously developed tumours located either between the stomach and liver or sub-cutaneously (located on or very near the incision line). Immunostaining for the anti-human nuclear antigen revealed that none of these tumours were of donor (human) origin. Nevertheless, their presence indicates the possibility of the raised risk of tumour development which might be associated with term HUCMC and FTM HUCPVC infusions. In contrast, infusion of term and FTM HUCPVCs in nude mice observed over a 6 month period (n=3) in a myocardial infarction model, revealed no detectable tumor formation (data not shown). Nevertheless, this risk requires further investigation prior to clinical translation.

Conclusions

The lack of detection of infused cells within the peri-lesional area of the spinal cord imposes limits on the characterisation of the sub-population that reaches and/or survives that is likely to be responsible for localised vasculogenic effects detected. It also suggests that early benefit is preserved chronically even in the absence of infused cells at or near the lesion site. The secretory profiles of the cells used in this study can be used to identify potential molecular mediators of benefit. Culture conditions could be adjusted to prime cells prior to infusion to secrete more pro-angiogenic factors.

The choice of cells is important even though no differences in their acute beneficial effects on the vasculature can be determined. Umbilical cord-derived cells are better than adult BMSCs for chronic neuroanatomical integrity, and are better for glial scar reduction. Other characteristics of these cells may have a role to play in chronic functional recovery from traumatic SCI, including their myogenic differentiation.

This Example shows that the minimally invasive approach of early MSC infusion in a clinically relevant model of moderately severe cervical SCI leads to modest chronic neuroanatomical functional improvements, most prominently by MSC-like cells derived from the first trimester umbilical cord perivascular cells. This suggests that this cellular treatment could be applied in a combinatorial strategy with other approaches to achieve better recovery.

This could also be applicable to injuries and neurodegeneration affecting other parts of the CNS.

Example 4

Early Mesenchymal Cell Infusion Reduces Acute Vascular Disruption After Traumatic Spinal Cord Injury Summary In this Example, it is demonstrated that early mesenchymal cell infusion reduces acute vascular disruption after traumatic spinal cord injury. Disruption of the blood-spinal cord barrier occurs immediately after spinal cord injury (SCI) and plays a major role in triggering the secondary injury cascade. Mesenchymal Stromal Cells (MSCs), including human umbilical cord matrix cells (HUCMCs), have pericytic attributes and may promote vascular repair, reduce tissue loss and functional impairment. HUCMCs, adult bone marrow MSCs (BMSCs), first trimester human umbilical cord perivascular cells (FTM HUCPVCs) or newborn fibroblasts were infused via the tail vein 1 hour post clip compression-induced cervical SCI in rats, which were sacrificed 1 or 3 days later. Snap-frozen homogenates of spinal cord tissue were used for spectrophotometric quantification of vascular permeability and lesional hemorrhage using Drabkin's assay. Pre-sacrifice, very high frequency ultrasound (VHRUS) measurements of the hemorrhage were undertaken. Vascular density was assessed histologically using LEA staining. It was found that HUCMC- ($p=0.038$ vs HE), BMSC- and FTM HUCPVC-infused animals had significantly less vascular permeability and parenchymal hemorrhage than HE- (HBSS+2 mM EDTA) or newborn fibroblast-infused rats ($p=0.47$ vs HE) at 24 hours post-SCI. Similar results were obtained when comparing lesion volumes (VHRUS) at 24 and 72 hours post-SCI. LEA staining indicated that both FTM HUCPVCs and term HUCMC-infusion post-SCI led to significant preservation of blood vessels in the lesioned spinal cord parenchyma 72 hours post-SCI ($p=0.0177$ vs HE).

The reduction of acute vascular permeability and parenchymal hemorrhage by MSC infusion is demonstrated herein, in a clinically relevant model of cervical SCI. This minimally invasive and effective approach holds translational promise for the acute treatment of traumatic SCI and other CNS injuries.

Introduction

The prevalence of spinal cord injury (SCI) in Canada and the US exceeds 1.3 million individuals (www.christopherreeve.org), with approximately 13,000 new injuries annually, about 60% of which are in the cervical region. Despite medical advances, many patients with SCI still experience substantial and permanent loss of motor, sensory and autonomic function. As current treatments for SCI are only minimally effective, the development of novel non-invasive strategies to reduce the deleterious effects of secondary pathophysiological events is essential, particularly since it has been shown that a modest improvement in neuroanatomical integrity after SCI can have substantial, clinically relevant impact on neurological recovery.

SCI involves a primary insult, followed by a series of secondary peri-lesional events which include: vascular disruption, cell death, inflammation, ischemia, reactive oxygen species generation, disruption of ion channels, demyelination and reactive gliosis. Some of the reactive efforts intended to limit the extent of damage, paradoxically, exacerbate the condition by inhibiting endogenous regeneration as well as interventional therapeutic treatments by creating an inhibitory milieu within and around the lesion site.

Vascular disruption of the blood-spinal cord barrier (BSCB) and edema play a role in triggering the cascade of secondary events culminating in progressive tissue loss and functional deficits. The BSCB remains compromised long after the initial primary mechanical damage to local vasculature due to the effects of inflammatory mediators (including matrix metalloproteinases) on endothelial cells and loss of astrocytes. Recent studies have shown that vascular stabilization after traumatic SCI can limit the severity of secondary. Limited endogenous neovascularisation is believed to constrain endogenous repair as well as the efficacy of therapeutic interventions. Molecular strategies to promote angiogenesis might support repair but must be balanced against the fact that newly formed blood vessels are more permeable than more mature ones and might exacerbate inflammation. Nevertheless, VEGF, erythropoietin (EPO), FGF1, FGF2, Ang-1, PDGF and statins have all shown promise in pre-clinical studies. However, this purely pharmacological approach cannot address the requirement for precise and dynamic modulation of the peri-lesional concentrations of pro-angiogenic factors.

Cell therapy is well suited to addressing the multi-factorial nature of SCI. Different sources and types of stem/progenitor cells, including embryonic stem cells, neural progenitor cells and bone marrow mesenchymal stem cells (BMSCs) are contemplated. Cell therapy for SCI must overcome the hostile and inhibitory microenvironment of the lesion site to enable implanted cells to integrate within host tissue, or persist long enough to induce paracrine effects, and provide functional benefit. In this regard, mesenchymal stem cells are ideal. Intravenously administered adult BMSCs have been shown to provide benefit in models of SCI. Even with low engraftment, they have been shown to increase the density of new blood vessels in the lesioned spinal cord, which can have functional benefit. Similar observations have been made in models of cerebral ischemia. However, the optimal choice of cells for this mode of treatment remains unknown, despite several clinical trials investigating systemic infusion of bone marrow cells for treatment of SCI.

Typically, adult progenitor cells fare less well than their fetal and embryonic counterparts, not only in terms of proliferation and differentiation, but also with regard to post-implantation survival, migration and integration within the recipient CNS. It was therefore hypothesized that recently characterized cells with MSC-like properties from human umbilical cord tissue would be superior alternative source of MSCs to adult BMSCs.

The umbilical cord consists of an outer layer of amniotic epithelial cells enclosing a gelatinous matrix known as Wharton's jelly, which contains two arteries and a vein. The matrix, especially the perivascular region, is a rich source of progenitor cells. Both first trimester human umbilical cord perivascular cells (FTM HUCPVCs) and term birth human umbilical cord matrix cells (HUCMCs) are similar to BMSCs, but these cells are less mature and have superior proliferation potential, have higher levels of telomerase activity and, unlike BMSCs, they can undergo repeated freeze-thaw cycles without significant loss of viability and without accumulating karyotypic abnormalities. HUCMCs and FTM HUCPVCs are thought to be non-immunogenic, and may even suppress the immune response, potentially making them suitable for allogeneic transplantation. They are highly pathotropic following transplantation, and possibly more so than adult BMSCs. Of greatest relevance to SCI, they secrete a wide range of trophic factors known to promote neural cell survival. HUCMCs have also proven beneficial post-SCI in the clinic.

Acute vascular permeability and parenchymal hemorrhage are reduced by MSC infusion in a clinically relevant model of moderately severe cervical SCI. Vascular disruption is assessed herein in live animals using Very High Resolution Ultrasound, which has been previously validated, and complemented this method with more traditional techniques (Evans blue and Drabkin's assays). This minimally invasive and effective approach to cell therapy has profound translational implications to the acute treatment of traumatic SCI and other CNS injuries.

Material & Methods

Passage-matched (passage 6 to 7) FTM HUCPVCs, term HUCMCs, adult BMSCs, newborn and adult dermal fibroblasts cultured under identical conditions were compared as detailed below. Cells were infused intravenously 1 hour after SCI. Various readouts were obtained 24 or 72 hours later. Experimental rats were randomly divided into 5 per condition/treatment and sacrificed 24 or 72 hours post-SCI. All experiments involving animal use were approved by the University Health Network Animal Care Committee, Toronto Canada.

Cells were infused intravenously 1 hour after SCI. Various readouts were obtained 24 or 72 hours later.

Tissue procurement & Cell isolation. 2-3 cm of term umbilical cord was purchased from LifeLine Stem Cells (New Haven, Indiana, USA), and dissected in sterile Hank's Buffered Saline (HBSS, Gibco, Canada) containing 1% gentamycin using aseptic technique. The vein and arteries were carefully removed. Pieces of Wharton's jelly (umbilical cord matrix) were then transferred to collagenase I and II (1 mg/ml, Gibco, Canada), diced into small pieces and incubated for up to 2 hours at 37° C. on an orbital shaker before adding $Ca^{2+}$ and $Mg^{2+}$-free Phosphate-Buffered Saline (PBS, Gibco, Canada) to the viscous cell suspension, triturating and centrifuging at 2000 rpm for 10 minutes at room temperature.

FTM HUCPVCs were isolated as described herein, and obtained from Create Fertility Centre (University of Toronto, Canada). Other cells types used included passage-matched adult human bone marrow stromal cells (BMSCs, Lonza), and adult (PCS-201-012, ATCC) and newborn (CRL-2703, ATCC) human fibroblasts. Identical culture conditions were used for all cell types and sources.

Cell Culture. Cells were seeded into uncoated tissue culture T175 flasks (Greiner, Canada) in Alpha-MEM (Gibco, Canada) containing 10% batch-tested fetal bovine serum (FBS, HyClone, USA Lot #KTJ32091), 1% sodium pyruvate, 1% Glutamax and 0.1% gentamycin (Sigma-Aldrich, Canada) (complete medium). This culture was referred to as passage 1 (p #1). After 2 to 5 days, the non-adherent HUCMCs were either discarded or reseeded into a fresh dish (p #1B). Fresh complete medium was added to the original dish (p #1A) and the adherent cells were grown to a maximum 70-80% confluence before passaging, harvesting for infusion or cryogenic storage. The medium was completely replaced twice a week.

Sub-confluent passage number 6-7 cultures were passaged at no more than 70-80% confluence using trypsin-like enzyme (TLE, Sigma-Aldrich, Canada). The cells were resuspended in 1 ml fresh medium and dissociated by gentle trituration. After passing the cell suspension through a 70 μm filter to remove any clumps, total cell counts and viabilities were determined haemocytometrically using the Trypan blue dye (Sigma-Aldrich, UK) exclusion assay. Cells were reseeded into fresh uncoated 140 mm tissue culture dishes (Greiner, Canada) at $5 \times 10^5$ cells per 20 ml. In order to prevent re-aggregation prior to infusion, cells were instead resuspended in Hank's buffer containing 2 mM EDTA and were kept on ice for no more than 2 hours after dissociation.

SCI Model and Cell Infusion. All surgeries were performed by a single researcher. Young adult female Wistar rats (250-300 g) received a C6 28 g or C7 35 g clip compression SCI for 1 minute under Isoflurane anaesthesia with a 1:1 mixture of $O_2$/NO2 (1 L/min). Acute vascular disruption post-SCI was targeted by systemically infusing 2.5 million cells in 1 ml Hank's buffer/2 mM EDTA (HE, to prevent re-aggregation prior to infusion) via the tail vein 1 hour post-SCI (translating into a realistic timeframe of acute intervention of a few hours in a human patient). Cells were kept on ice for no more than 2 hours after dissociation. Infusion via the tail vein was performed manually but over a duration of no less than 5 minutes. Increasing the cell number and/or infusion any sooner was associated with a higher rate of mortality occurring immediately after cell infusion. Animals were randomly assigned to a treatment group and given a coded designation until data acquisition and processing was complete. Specialised post-operative husbandry protocols were followed by qualified and experienced personnel (also blinded to treatment conditions) to maximise animal welfare. These included corn cob (1¼) and Isopad bedding, Clavamox-supplemented drinking water and Bacon Softies diet (starting immediately postop). Animals were caged singly post-operatively with Nylabone and kept on a 12-hour light/dark cycle at all times. Bladder squeezing (three times a day), cyclosporine (Sandimmune) injections (10 mg/kg s.c. once daily) and Buprenorphine injections (0.05 mg/kg s.c. twice daily) were performed at regular times.

The effects of treatment relative to controls were evaluated by measuring hemorrhage, vascular integrity and inflammation. Rats were terminally sedated with Isoflurane and sacrificed by intracardial perfusion with PBS. The spinal cord was isolated along with other organs. A defined length (5 mm) of the lesioned spinal cord was isolated and snap-frozen on dry ice. An equal length of the spinal cord rostral and caudal to the lesioned spinal cord was also isolated and processed identically. Snap-frozen homogenates of 5 mm lesional and 5 mm peri-lesional (rostrocaudal) spinal cord tissue were divided into 3 equal portions for spectrophotometric quantification of Evans blue (EB) dye, myeloperoxidase (MPO) activity assay and Drabkin's assay.

Careful consideration was given to approved standards of reporting for all procedures and data described (Animals in Research: Reporting in Vivo Experiments, ARRIVE and Minimum Information about a Spinal Cord Injury Experiment, MIASCI).

Very High Resolution Ultrasound Imaging (VHRUS) & 3D Lesion Assessment. The injured spinal cord was examined in live rats by echography with very high-resolution ultrasound (VHRUS) with a 44 MHz probe (Vevo 770, VisualSonics, Toronto, Canada). Three-dimensional (3D) VHRUS acquisitions were made in B-mode. The 3D files were analysed with ImageJ software as previously described with minor modifications. Instead of using a set ROI, the bright pixel lesions were delineated by two independent blinded observers within a 15 sagittal image slice stack (102 μm) to generate a reproducible 3D lesion volume.

Parenchymal Hemorrhage—Drabkin's Assay. Parenchymal hemorrhage was assessed via a modified version of the manufacturer's instructions (Sigma D5941). The sample was sonicated in 100 μL of deionized distilled $H_2O$ and subsequently centrifuged at 13000 rpm for 15 minutes. The supernatant was collected and added to complete Drabkin's Reagent (Drabkin's Reagent powder in 1000 mL of distilled H$_2$O and 0.5 mL of 30% Brij 35 Solution) and allowed to stand for 15 minutes for the reaction to take place (haemoglobin to cyanomethaemoglobin). Colorimetric measurements were performed using the Perkin Elmer Victor2™ spectrophotometer (Wallac 1420 Victor2™, Perkin Elmer, Waltham, USA) at 540 nm, normalized to tissue weight (in grams) and calculated based on a bovine blood haemoglobin (H2500, Sigma-Aldrich, Canada) standard curve.

Vascular permeability—Evans Blue Assay. Wistar rats were infused with 2% Evans blue (EB) in PBS without Ca2+ and Mg2+ 30 minutes prior to sacrificial perfusion with 250 ml PBS without Ca2+ and Mg2+. The third of 5 mm lesion and peri-lesional (rostrocaudal) spinal cord tissue was homogenized in 500 µL of dimethylformamide (DMF) and incubated at 50° C. for 24 hours. The samples were subsequently centrifuged at 13000 rpm for 15 minutes. The supernatant was collected and 150 µL was aliquoted into a 96 well flat bottom glass plate (Zeisser, Germany) and colorimetric measurements were performed using the Perkin Elmer Victor2™ 1420 spectrophotometer at 620 nm. Samples were normalized to tissue weight (g) and EB concentration was calculated based on a standard curve in DMF.

Histology. Spinal cords were isolated from rats perfused with 250 ml chilled PBS (without Calcium and Magnesium) followed by 50 ml of chilled 4% paraformaldehyde (PFA). Spinal cords were then post-fixed in 4% PFA overnight at 4° C. before transfer to 30% sucrose (at 4° C.) and storage in OCT (at 4° C. for 1-2 days then −20° C.) until embedding in fresh OCT and cryosectioning (20 µm thick cross-sections). The delay between spinal cord isolation and cryosectioning was minimised as much as possible. To label endothelial cells, a DyLight 594-conjugated tomato lectin from *Lycopersicon esculentum* agglutinin (LEA, VectorLabs, 1:300) was used. Anti-human nuclear antigen antibody was used to detect human cells (Millipore MAB1281, 1:200). Slides were baked for 15 minutes at 55° C. so cryosections would adhere permanently to the slides. After blocking in PBS (without Calcium and Magnesium)+2% FBS+0.1% Triton-X for 1 hour at room temperature, primary antibodies diluted in the same diluent solution were applied overnight at 4° C. After 3 washes in PBS, secondary antibodies (1:200 dilution) were applied as necessary. Hoechst 33242 was used as nuclear counterstain. Slides were mounted in Mowiol medium after 5 PBS washes. Negative staining controls (primary or secondary antibody alone) were used to assess baseline image acquisition parameters. The latter were kept consistent for each fluorescent channel between slides and treatment conditions. All staining was performed in one batch and the delay between mounting slides and image acquisition was kept to a minimum. To use as additional positive staining controls, rats were injected intra-spinally with HUCMCs (25 000 cells/3 ul) after C6, 23 g SCI into 4 sites rostrocaudal to the lesion.

Auto-fluorescence Correction Protocol. Hemorrhage interferes with fluorescent microscopy due to the high auto-fluorescence of blood-borne components. Removing this signal manually is not possible. Images (18200×25000 pixels) were segregated into red channel (LEA) and green channel folders, and renamed to matching sample names. The images were then batch-downscaled in ImageJ® to 25% of their original dimensions for feasibility of analysis (Process>Batch>Macro). The red and green images were then thresholded using the Color Threshold function. The images were then saved as <SampleName>-LEA.tif, and using the OR function in the Image Calculator, the overlapping area (corresponding to the auto-fluorescent signal) between images of different channels was determined and saved as <SampleName>-Auto.tif. Following this, the images that were previously generated (<SampleName>-LEA, -Auto.tif) were all opened, and using the SUBTRACT function in the Image Calculator, the computed auto-fluorescence was subtracted from the thresholded LEA images, respectively. The final results were saved as <SampleName>-LEA-Final.tif, and their signal levels were represented as a % area fraction using the Measure function.

Statistical Analyses. Statistical analyses were performed with GraphPad Prism software (La Jolla, CA, USA). Unless otherwise stated, One-Way ANOVAs and Bonferroni's multiple comparisons tests were performed. Standard errors of means were compared using the Brown-Forsythe test.

Results

The antigenic profiles of the FTMHUCPVC cells employed in this study have been previously characterised. The majority of HUCMCs expressed the classical mesenchymal markers, including CD90, CD44, CD166, CD105, CD73, prolyl-4-hydroxylase, vimentin, collagen I, alkaline phosphatase but no haematopoietic markers (CD45 and CD34). Most fibroblasts expressed prolyl-4-hydroxylase, collagen I and the proliferative marker Ki67 but not the other MSC and haemotopoietic lineage markers tested. Passage-matched term HUCMCs, FTM-PVCs and BMSCs were morphologically similar (spindle-shaped) and proliferative.

Very High Resolution Ultrasound (VHRUS) enables the visualization of the spinal cord in live animals after laminectomy under anesthesia. The lesion site was examined using this technique after an extra rostral (C6) laminectomy—a double C7-T1 laminectomy had previously been performed for inducing SCI. A significant reduction in parenchymal hemorrhagic lesion volume was found at 24 and 72 hours after 35 g C7 SCI with 1-hour post-SCI infusions of FTM-PVCs, HUCMCs or BMSCs, but not newborn fibroblasts. This difference was no longer detected 1 week post-SCI. There was no statistical difference between the MSC sources.

Haemorrhagic lesion volumes were measured by VHRUS at 24 and 72 hours and 1 week post-C7, 35 g (1 minute) SCI.

Parenchymal hemorrhage was measured after C7, 35 g 1-minute clip compression SCI using the Drabkin's assay. MSC infusion 1 hour after C7 SCI significantly reduced the amount of hemoglobin in the lesioned spinal cord parenchyma 24 hours later, unlike newborn fibroblasts. However, this effect was lost at 72 hours post-SCI. Although a trend for reduced parenchymal hemorrhage was observed rostrocaudal to the lesion at 24 hours following cell infusion relative to vehicle-infused rats (also reduced lesional hemorrhage at 72 hours post-SCI), this failed to achieve statistical significance. No significant difference was seen between the MSC sources.

In order to confirm that these vasoprotective effects were indeed due to live cell infusion and not simply a passive mechanical effect on the spinal cord vasculature (and given the lack of significant difference between MSC sources on vascular permeability), lysed cells were infused. However, these resulted in immediate mortality upon infusion, even after resuspending the lysate in fresh vehicle. The same was seen after adult fibroblast infusion. Therefore term HUCMCs were infused, which had been fixed in 4% paraformaldehyde for 10 minutes, washed and resuspended in 1 ml vehicle per 2.5 million cells. No mortality was observed, but interestingly, parenchymal hemorrhage was reduced at a similar level to that seen with live cells.

Vascular permeability was examined after C7, 35 g 1-minute clip compression SCI using pre-sacrificial EB infusion. MSC infusion 1 hour post-C7 SCI significantly reduced the amount of dye that extravasated into the lesioned spinal cord parenchyma 24 hours later, unlike newborn fibroblasts. This effect was not seen rostrocaudal to the injury and was lost at 72 hours post-SCI at the lesion site. No significant difference was seen between the MSC sources.

In order to identify whether the observations made were specific to C7 injury, the efficacy of vascular permeability reduction with intravenous cell infusion was examined at different clinically relevant injury levels and severities. The same significant reduction in vascular permeability was seen at 24 hours post-SCI after HUCMC infusion 1 hour post-SCI at multiple cervical SCI levels and severities but, although the trend was maintained, significance was not reached at T11, 35 g SCI (p=0.2126). The reduction in lesional vascular permeability was smaller after C6, 18 g SCI compared to C6, 28 g but very similar between the two C7 SCI severities tested (28 g and 35 g). Lesional vascular permeability after intravenous term HUCMC infusion at different injury levels and severities was evaluated, with n=5 per group.

The effects of lesional vascular permeability of FTM-PVC, HUCMC and newborn fibroblast infusion 1 hour post-C6 SCI, another clinically relevant model was investigated. A significant reduction in the amount of dye that extravasated into the lesioned spinal cord parenchyma 24 hours post-SCI was found after MSC infusion, but not newborn fibroblasts. Unlike observations made after C7 SCI, this effect was maintained at 72 hours post-C6 SCI. No significant difference was seen between these two umbilical cell sources. This was found upon observing lesional vascular permeability after intravenous cell infusion at 24 and 72 hours after C6, 28 g SCI (n=5 per group).

In order to determine the mechanism of action of infused cells, term HUCMCs were infused intravenously 1 hour post-C6 28 g SCI, Evans blue was injected systemically and rats were sacrificed 30 minutes later. There was no significant reduction of lesional vascular permeability seen at this time point with this treatment. Lesional vascular permeability was assessed at 30 minutes after intravenous term HUCMC infusion 1 hour post-C6, 28 g SCI (n=4 HE; n=6 HUCMC; Unpaired two-tailed T-test with Welch's correction).

Vascularity was examined after C7, 35 g 1-minute clip compression SCI using LEA staining on histological cryosections. LEA labels endothelial cells. Parenchymal hemorrhage was clearly visible in cryosections. After C7 SCI, term HUCMC-infusion 1 hour post-SCI led to a significant preservation of blood vessels in the lesioned spinal cord parenchyma 72 hours post-SCI, unlike newborn fibroblasts. This effect was not seen at 24 hours post-SCI at the lesion site (data not shown). Human cells were not detected after intravenous infusion, even though the antibodies used were validated.

Cross-sections (20 µm thick) of peri-lesional spinal cord were observed at 24 hours post-SCI (×4 magnification). Lesional vascular density represented was assessed by area of staining for LEA (n=3 per condition). As positive staining controls, rats were injected rostrocaudal to the injury site with 90 000 term HUCMCs after a C6, 23 g 1-minute SCI (4 injection sites, 2 rostral and 2 caudal to lesion site; 3 µl per site) at 4 weeks post-SCI and sacrificed 3 days later. 20 µm thick longitudinal sections were stained with anti-human nuclear antigen antibody (Millipore MAB1281, 1:200).

It was found that an unavoidable distortion of the anatomy of the spinal cord occurred during isolation. In addition, many smaller hemorrhagic foci seen during cryosectioning were no longer visible after collection of cryosections onto microscope slides.

VHRUS image showed a loss of morphology during spinal cord isolation, when assessed pre-isolation, after cutting ends of spinal cord; rostral to injury site; and caudal to injury site.

Discussion

This Example found that early systemic infusion of human MSCs of various derivations, not including fibroblasts, significantly reduces acute vascular disruption after traumatic SCI. Vascular disruption was quantified using 3 complementary techniques. VHRUS signal of a hemorrhagic lesion in live animals correlates with both Evans blue-assessed vascular permeability and Drabkin's reagent-assessed parenchymal hemorrhage at 24 hours post-SCI, and Evans blue and Drabkin's assay data correlate with each other at the same time point. Combined VHRUS, Evans blue and Drabkin's quantification of vascular disruption may be more accurate than histological methods because of distortions in the anatomy of the spinal cord during isolation.

Although acute localised vascular disruption occurring post-SCI can trigger and determine the severity of secondary injury and functional impairment, treatment options are limited. Vaso-protective and/or pro-angiogenic cell therapies optimised by comparing multiple human cell types and sources specifically targeting this disruption have not been described for SCI. Previous studies using systemically infused rodent adult MSCs have found reduced acute vascular permeability and improved chronic functional outcome relative to controls. The optimal choice of cells for this mode of treatment remains unknown, despite several clinical trials testing the systemic infusion of bone marrow cells for the treatment of SCI. Although not yet a fully validated therapy for SCI, the safety of this approach has already been established by its clinical application to other conditions, including multiple sclerosis and also in pre-clinical studies.

Despite the effects of reducing vascular disruption, infused cells could not be found within the spinal cord using immunohistological methods. It is assumed that many accumulate in the lungs, liver and spleen and from there (if they survive) are able to secrete trophic and immunomodulatory molecules into the circulation to achieve their observed effects. The fact that no cells could be detected histologically suggests that very few localize or remain in the spinal cord after infusion. This might explain the absence of a detectable effect on peri-lesional neutrophil and macrophage/microglial infiltration. The absence of infused cells within the spinal cord might also be explained by the possibility that they are washed away during the perfusion of the animal prior to isolating the spinal cord. Not perfusing would mean that RBCs/haemoglobin would remain in the tissues and interfere with immunohistochemistry and possibly even with PCR.

The infusion of fixed cells on parenchymal hemorrhage 24 hours post-SCI demonstrates that the hemostatic effects seen in this study rely, not on live infused cells, but rather on a passive mechanical effect likely localized to the peri-lesional site. On the other hand, vascular permeability is likely to rely on live infused cells rather than being a passive mechanical effect since vascular permeability was not significantly reduced 30 minutes after live cell infusion, which would have likely been the case in a purely mechanical hemostatic scenario.

Neuro- and vasoprotective strategies have failed in clinical trials despite promising pre-clinical studies. One reason for this is likely to be the heterogeneity of injuries seen in the clinic as opposed to the standardised models employed and strived for in the laboratory. To address this issue, the efficacy of the approach taken herein was examined by administering cells after SCIs of multiple severities and at multiple levels. From these investigations, it emerged that early systemic cell infusion is effective at reducing BSCB disruption after cervical (which affects the majority of sufferers) but not lower thoracic SCI. Given that neuronal cell bodies have a higher metabolic requirement than axons and glia, gray matter is more highly vascularized than white matter. After SCI in the monkey, gray matter vascular perfusion drops whilst white matter perfusion increases, indicating that ischemic mechanisms play a lesser role in white matter damage following traumatic injury. This is a possible explanation for the greater vulnerability of gray matter (more abundant in cervical levels of the spinal cord) compared to white matter. The lack of significant vascular permeability reduction after T11 SCI compared to cervical SCIs might be a result of the drop in blood pressure after the latter but not the former. This fall in vascular perfusion post-SCI would exacerbate the death and dysfunction of peri-lesional endothelial cells and pericytes.

In this example infused cells could not be detected within the spinal cord even with significant cell infusion-induced reductions in parenchymal vascular permeability.

Conclusions

For the purpose of acute vasoprotection after SCI, the source of MSCs does not seem to matter but the type of cell used does. The choice of MSC source is determined by practical, ethical and logistical considerations, including ease of isolation and proliferation potential in culture.

Evans blue dye binds circulating albumin to generate a 69 kDa molecule that permeates the disrupted vasculature. However, many cytokines and neurotrophic factors are in the 12-45 kDa size range and might be able to cross the BSCB even when Evans blue-albumin can no longer do so. Thus, the use of smaller molecular markers of vascular disruption alongside Evans blue would be informative. Furthermore, red blood cells are in the 6-8 µm size range. Labelling these extravasating RBCs would also be useful in examining the extent of severe BSCB disruption in future studies.

In an effort to better understand the mechanisms of action of intravenously infused cells on the lesional and peri-lesional vasculature, acute changes in the molecular components of the BSCB can be examined after cell infusion.

Reduction of acute vascular permeability and parenchymal hemorrhage by MSC infusion is shown herein, in a clinically relevant model of moderately severe cervical SCI. This minimally invasive approach to acutely administered cell therapy has the potential to facilitate the clinical deployment of MSCs to reduce the vascular disruption resulting from traumatic CNS injury. As for other traumatic injuries to the CNS, it is unlikely that any single therapeutic approach will treat the myriad of secondary events occurring as a result of the insult. This paradigm is more likely to become part of the arsenal of multi-modal treatments not only for SCI, but also for injuries and neurodegenerative conditions affecting other parts of the CNS, and possibly other organ systems.

Example 5

First Trimester Human Umbilical Cord-Derived Perivascular Cells have Cardiovascular Regenerative Potential Summary In this Example, it is shown that first trimester human umbilical cord-derived perivascular cells (FTM HUCPVCs) exhibit superior cardiovascular regenerative potential compared to older sources of human MSCs. Younger human mesenchymal stromal cell (hMSCs) sources can be more effective than older sources of hMSCs for cell-based therapy of myocardial infarction (MI). In this Example, the objective was to compare the ability of first trimester (FTM) HUCPVCs versus other hMSC sources to 1: migrate towards and reconnect injured cardiomyocytes in vitro 2: support angiogenesis 3: engraft in a rat MI model and 4: improve cardiac function after MI. Matrigel™-coated transwell membrane infiltration by FTM, term HUCPVCs or bone marrow stem cells (BMSC) in response to injury of rat cardiomyocytes by wounding or hypoxia, was measured using live fluorophores. Intracellular and mitochondrial dye transfer between hMSCs and cardiomyocytes in co-culture was measured. The effect of hMSCs on developing endothelial networks was evaluated in a modified rat aortic ring assay. hMSCs were injected into the myocardium of Foxrnu rats 1 week following coronary artery ligation. At 2 weeks, cardiac function was assessed in rats by echocardiography, cell retention by AluII-based qPCR, and FISH. Scar tissue size and vasculature were assessed by IHC. It was found that FTM HUCPVCs showed increased invasion towards injured cardiomyocytes, reconnected cardiomyocytes, and promoted increased growth of endothelial networks in vitro compared to other hMSCs. Echocardiography showed significantly increased cardiac function in FTM HUCPVC- but not BMSC- and term HUCPVC-treated rats when compared to controls. A 2-fold and 5-fold increase in FTM HUCPVC retention was observed when compared to term HUCPVCs and BMSCs, respectively. FTM HUCPVCs significantly improved scar tissue vasculature. The effect sustained up to 6 weeks in nude mice.

Introduction

Cardiovascular disease is the leading cause of mortality and morbidity globally. While congenital heart disease affects the young and the middle aged, coronary heart disease predominantly afflicts adults and the elderly. Congestive heart failure (CHF) is the terminal form of all heart diseases, with the highest mortality rates worldwide. In 2015, approximately 5 million people lived with CHF in the USA.

During an episode of acute myocardial infarction (MI), impaired blood flow due to an obstructed coronary artery triggers an ischemic cascade leading to insufficient perfusion of the heart. The hypoxic injury results in permanent damage to heart tissue and, without successful intervention, frequently leads to CHF. In addition to drug-based therapies, major surgical procedures such as coronary artery bypass and medical devices providing mechanical augmentation for the ventricular myocardium are frequently administered, with significant risk of complications. Heart transplantation for post-MI patients with congestive heart failure is the most invasive procedure, considered extremely high-risk, and is limited by both organ availability and cost, making it unsustainable as a large scale solution. A highly successful and efficient therapy to replace damaged cardiac tissue and revitalize the cell-free fibrotic scar thereby preventing CHF has yet to be found.

Regeneration of the Cardiac Vasculature. The heart has the highest aerobic metabolic rate of any organ in the human body. The extensive nutrient and oxygen demand makes the maintenance and repair of heart vasculature essential both physiologically and post-injury. Endothelial cell damage plays an important role in cardiac pathologies such as atherosclerosis, thrombosis and hypertension, and physiological balance between endothelial cell loss and endothelial repair is crucial for reducing cardiovascular failure. Besides regrowth or repair of cardiomyocytes, efficient regenerative therapy following ischemic injury requires the repair of existing blood vessels as well as the formation of new blood vessels (neovascularization). While fully differentiated endothelial cells have a reduced capacity to regenerate vasculature, endothelial progenitor cells (EPCs) have been shown to be major contributors to angiogenesis and cardiac regeneration. Previous studies suggest that aging is associated with a reduced number and function endogenous EPCs. The combined effect of decreased EPC and BMSC numbers as well as function with age is a possible explanation for the limited cardiovascular regenerative potential in the elderly. An optimal cell type for cardiovascular repair should exert a significant beneficial effect on the vasculature in order to extend and prolong regeneration and reduce the risk of relapse and secondary heart failure. The vascular regenerative effect can derive from generating local, perfundable vasculature in situ and anastomose them with existing vessels and/or attracting blood vessel outgrowth from unaffected sites in the heart. Ultimately, the regenerated vasculature after an ischemic episode should resemble the features of healthy myocardium, both in terms of vascular density and blood vessel size in order to restore the heart's organized function as a whole.

MSC-based Cell Therapy for Cardiovascular Regeneration. Since the 1990s, many groups reported that implantation of healthy cells into the damaged myocardium can facilitate remodeling, enhance endogenous healing mechanisms and preserve ventricular structure and function in preclinical animal models of myocardial infarction (MI). The cellular and molecular mechanisms required for successful myocardial engraftment of transplanted cells have been described in detail elsewhere. Therapeutic cells need to survive and adapt in the microenvironment of the injured myocardium, promote the viability and proliferation of host cardiomyocytes, remodel the extracellular matrix (ECM) and activate resident and infiltrating progenitor cells to induce neoangiogenesis and cardiomyocyte turnover.

Mesenchymal stromal cells (MSCs), in particular bone marrow MSCs (BMSCs), have gained substantial interest in the context of tissue regeneration. MSCs can be isolated from many tissues, easily expanded, exhibit immunomodulatory effects, have properties of immunoprivilege, induce paracrine effects and they can be genetically modified in vitro. Extensive cardiac preclinical studies have demonstrated their safety and efficacy. Although the mechanism for the beneficial effects of cell transplantation remains unclear, ventricular function was improved in all studies.

Promising results from MSC-based pre-clinical studies has led to the initiation of greater than 20 NIH-registered clinical trials, which have mainly included autologous and allogeneic BMSCs. However, in sharp contrast to the improvements observed in animal models, the clinical trials using autologous cells produced only marginal benefits. Age-related limitations in the regenerative capacity of the implanted and endogenous progenitor cells are considered to be a major factor in the limited efficacy.

Human Umbilical Cord-derived Perivascular Cells. A young source of immuonoprivileged MSCs derived from the perivascular region of first trimester and term umbilical cord tissues is used, as described herein. First trimester human umbilical cord perivascular cells (FTM HUCPVCs) show pericyte-like characteristics, ability to differentiate into mesenchymal and non-mesenchymal lineages including cardiomyocyte-like cells. Superior multi-lineage differentiation, immunoprivileged and paracrine properties of FTM and also term HUCPVCs over BMSCs are exhibited. In this Example, it is examined whether FTM HUCPVCs have the ability to act at multiple levels of cardiovascular regeneration and their superior versatility could make these cells an optimal candidate for post-MI cell therapy.

Materials and Methods

All studies were performed with institutional research ethics board approval (REB No. 454-2011, Sunnybrook Research Institute; REB 29889, University of Toronto, Toronto, Canada). Established lines of FTM HUCPVCs and term HUCPVCs and a commercially available line of bone marrow MSCs (Lonza) were cultured in alpha-MEM (Gibco) supplemented with 10% FBS (Hyclone), and penicillin/streptomycin cocktail (Gibco), and passaged at 70-80% confluency. Rodent primary cardiomyocyte cultures were kept in DMEM-F12 containing 10% FBS (Hyclone) and penicillin/streptomycin cocktail (Gibco). MSC-monocyte co-cultures were kept in RPMI supplemented with 10% FBS (Hyclone) and penicillin/streptomycin. Cell cultures were kept in humidified incubators (37° C., 5% $CO_2$).

All animal procedures were conducted and reported according to ARRIVE guidelines and approved by the Animal Care Committee of the University Health Network (Toronto, Canada). All animals received humane care in compliance with the Guide for the Care and Use of Laboratory Animals (National Institutes of Health 1996). Primary rat cardiomyocyte cultures were prepared from rats sacrificed at p2-5. Ventricular myocardium was minced and agitated at 37° C. in 1.5% trypsin PBS solution. Primary cultures were treated with BrdU (16 h, 5 µM) and washed prior to addition of MSCs 24 hrs later. Dissociated MSCs were added to cardiomyocyte monolayers to achieve 5% MSC content in each well. Alternatively MSCs were labeled with viable, non-transferable fluorescent dye (CellTracker-Green, Invitrogen 5 µM, 1 h) prior to transfer, in order to visualize integrating MSCs.

In vitro Trans-membrane Invasion Assay. The extravasation capacity of MSCs in response to injured cardiomyocytes signals was evaluated using Corning Biocoat Transwell™ migration assays. Primary rat cardiomyocytes were plated in each well at high confluency. After cells attached, injury was applied by incisions (wound) or 24 h glucose/oxygen deprivation (ischemia), and FTM HUCPVC, term HUCPVC and BMSCs were plated on Matrigel™-coated membrane inserts separating human MSCs from rat cardiomyocytes. An endothelial cell invasion assay kit (BD #354141) was used to quantify trans basal membrane migration capacity of human MSCs. 30 k MSCs were plated on the Matrigel™-coated Transwell™ 3 µm pore plastic membrane inserts. Primary rat cardiomyocytes were seeded into 24 well tissue culture plates (200 k each). 24 h later, seeding media was replaced with FBS free D-MEM-F12 supplemented with 1% penicillin/streptomycin (assay media). Cardiomyocyte monolayers were injured by applying 6 radial incisions per well or incubating for 24 h in glucose free Ringers solution with air tight sealing (ischemia). Media was changed in ischemic wells to assay media before adding MSC-containing inserts. Inserts were incubated with cardiomyocyte wells for 24 h, stained with calcein-AM and scanned with a fluorescent plate reader (FilterMax F5 MolecularDevices) according to the manufacturer's description (BD). Cells were visualized by fluorescence microscopy (EVOS, LifeTechnologies).

In vitro Wound Healing Assay. In order to assess the direct regenerative potential of MSCs on physically injured primary cardiomyocyte cultures, an in vitro wound healing assay was performed. A modified version of an in vitro scratch assay was applied. Briefly confluent, synchronously contracting rat primary cardiomyocyte culture was subjected to scratch incision using a sterile 20 gauge needle. FTM, term HUCPVCs and BMSCs were administered to the cardiomyocyte cultures 1 hour after the incisions were made. Unstained cell suspensions of MSCs were applied at the time of the incisions to observe their effect on wound closure. Pre-stained (CellTracker™ Green) FTM HUCPVCs were used to follow cell migration in the wounded cardiomyocyte culture. Cardiomyocytes were counterstained with CellTracker™Orange CMRA. Both intact and wounded fields were imaged for 48 h with fluorescence microscopy (EVOS, LifeTechnologies) to record changes in localization of CTG positive cells. After 48 h real-time fluorescence and bright field microscopy video recordings were acquired (EVOS, LifeTechnologies, Epiphan Systems) to assess for contractions of primary cardiomyocyte fields and the distribution of labelled cells in the vicinity of the wounds. Wound healing of primary cardiomyocyte monolayers co-cultured with MSCs was followed for 1 week by phase contrast and fluorescence microscopy.

Cell Content Transfer Between HUCPVCs and Cardiomyocytes. To assess mechanisms of direct cell-cell communication, HUCPVCs were loaded with transferable cytoplasmic fluorophore CellTrackerTMOrange CMTMR and rat cardiomyocytes were labelled with non-transferrable CellTracker™Green: CTG prior to establishing direct co-cultures. The mitochondrial fraction of mammalian cells was labelled with Rhodamine123, that is selectively accumulated by live mitochondria with high membrane potential. To assess for mitochondrial transfer, undifferentiated FTM HUCPVCs were incubated with non-transferable cytoplasmic fluorescent dye (CellTracker™Green) and live mitochondrial dye Rhodamine123. A single cell suspension of double-stained FTM HUCPVCs was added to unlabelled primary rat cardiomyocyte cultures and allowed to integrate for 24. Transfer of mitochondrial fluorophore was assessed by fluorescence microscopy for 72 hours.

Flow Cytometry and FACS. For FC and FACS, cell cultures were dissociated with 0.25% Trypsin/EDTA solution (3 min 37° C.). Cell suspensions were incubated with fluorophore conjugated primary antibodies according to provider's description (1:40, 30 min 4° C.). FC analysis was performed using either analogue (FacsCalibur, BD; Create Fertility Centre, Toronto) or digital (LSR II., Canto II., BD; UHN SickKids Flow Cytometry Facility, Toronto) analytical cytometers. FACS was performed using digital cell sorters (MoFlo Astrios, Aria II., UHN SickKids Flow Cytometry Facility, Toronto) and sorted cells were re-plated within 1 hour after the procedure. MSC treated rat hearts were processed for flow cytometry analysis to evaluate immunologically relevant cell surface molecules HLA-A and HAL-G levels of the engrafted human cells 2 weeks after administration.

Rat Aortic Ring Assay. Aortic tissues were isolated from female rats of reproductive age. After sectioning and embedding in an extracellular matrix extract (Matrigel™), sprouting endothelial networks were monitored and imaged until closed loops and structured networks were established. Human MSCs expanded in serum-containing conditions (alpha-MEM, 10% FBS) up to passage 4-6 and labeled with CellTrackerGreen™ were seeded onto Matrigel™-embedded aortic endothelium originated networks (10 k MSCs per mm aortic tissue section). After 24 hours of incubation, bright field and fluorescent images were taken to document overall network development, MSC localization and physical interactions between MSCs and endothelial cells. Phase contrast images consistent for size of fields of sight were taken of endothelial networks to measure radial growth of endothelial network and total number of closed loops for up to 7 days. In aortic ring originated endothelial networks uniform quadrants (n=12) circumscribing areas of developed tube networks were defined and number of closed loops were compared between treatment groups (Image J).

Immunocompromised Rat Model of MI. Surgeries were performed on anesthetized immunocompromised rats (Foxn1rnu homozygous) by certified animal surgeons (University Health Network, AUP #1059.27). Myocardial infarction was induced by permanent left coronary artery ligation. One week after MI, cells (3×10⁶) were administered in 3 injections directly into the anterior myocardium of the left ventricle, around the ischemic region. Echocardiography was performed using ACUSON *SEQUOIA* C256 System (SIEMENS Medical Solutions USA, Inc; California, USA) 2 weeks after cell treatment to assess cardiac function.

Immunocompromised Mouse Model of MI. Nude (NOD scid) mice were subjected to coronary artery ligation under isoflurane anaesthesia and within 24 h they were injected with human MSC suspensions or media as control. Injections were administered into the apical myocardium of the left ventricule ($10^6$ cells each). Echocardiography was following cardiac output for up to 6 months.

Histological Evaluation of Rat Heart Tissue. Rat hearts were ectomized at 2 weeks after MSC administration and processed for FC, basic histological evaluation and immunohistochemistry (IHC). For FC, cells were harvested from the anterior myocardium of the left ventricle using trypsin/collagenase treatment. HLA-A and HLA-G levels were analyzed in the TRA-1-85high fraction by flow cytometry, to evaluate immunologically relevant cell surface molecules in the engrafted human cells 2 weeks after administration.

For basic histological analyses, rat hearts from each experimental group were perfused and fixed with 10% formalin and embedded in paraffin for sectioning. Masson's trichrome staining was performed on heart sections at three levels of the scarred ventricles to quantify scar tissue formation. Vascular formation and density was assessed on deparaffinized tissue sections using endothelial membrane specific fluorescent isolectin (IB4, LifeTechnologies, 100× dilution in PBS).

Fluorescent in situ Hybridisation (FISH) and qPCR for Human Genomic DNA Tracing. Human cell retention was assessed qualitatively and quantitatively in MSC treated heart tissues applying previously reported primers for AluII human retrotransposon ($10^6$ copies per genome). AluII FISH probe (ALU, green) was applied for human cell tracing in the ischemic regions of the rat myocardium. Human umbilical cord section (human cord) was used for positive and untreated rat heart (rat heart no tx) as negative control. Genomic qPCR was performed. FITC conjugated oligos of the same sequences were applied for FISH (ACGT Corp. Toronto Canada). Briefly, deparaffinised tissue sections were subjected to epitope retrieval (pH6), permeabilization (triton-X100, 0.1%) and incubated with fluorophore conjugated oligos (200 nM) in hybridisation buffer (20 mM Tris pH7.4, formamide, blocking solution (Roche)).

Statistical Analysis. ANOVA followed by Multiple t tests (grouped analysis) were performed to detect and verify statistically significant differences ($\alpha<0.01$) between cell lines using Prism software (Graph Pad). p value was calculated using a one-way ANOVA and Tukey's Post test.

Sample size for flow cytometry (FC) measurements were: FTM n=9, term n=9, BMSC n=6 independent experiments using 2 lines per cell type; for vascular IHC: n>20 random fields of sight were taken of 3 animals per experimental group. Aortic ring assay: N=3 rings per treatment group, n=4 fields of sight. Echocardiography n=6 animals per treatment group. Alu genomic qPCR: 5 samples per experimental group were tested.

Results

It was found that FTM HUCPVCs actively migrate towards injured cardiomyocytes through basal membrane-like structures. Quantification of fluorescently-labeled MSCs in the trans-membrane invasion assay revealed that cardiomyocyte injury significantly increased active migration of 2 independent lines of FTM HUCPVCs in comparison to non-injured controls ($p<0.01$). This effect was not observed for term HUCPVCs. The transmembrane migration of BMSCs was significantly inhibited by cardiomyocyte injury ($p<0.01$).

Further, it was found that FTM HUCPVCs promote wound healing and reconnect cardiomyocytes after injury in vitro. In order to assess the direct regenerative potential of MSCs on physically injured primary cardiomyocyte cultures, an in vitro wound healing assay was performed. Straight incisions closed after 1 week in both FTM and term HUCPVC-containing co-cultures, while BMSC-containing primary cardiomyocyte cultures still contained uncovered, open wounds after 1 week. Closer inspection of the closed wounds (10×) revealed that while term HUCPVC-treated incisions were bridged by the protrusions of the cells on the edges of the wounded cardiomyocyte sheets, FTM HUCPVC containing co-cultures had a high number of cell bodies filling the grooves between cardiomyocyte sheets with different morphology than those of the original primary cardiac culture. In order to clarify the contribution of FTM HUCPVCs to the observed wound healing effect, cells were pre-stained with viable fluorescent dye (CellTracker™ Green, CTG) prior to administration onto injured cardiomyocyte monolayers. CTG-loaded FTM HUCPVCs were initially randomly distributed shortly after plating (3 h). Over time CTG positive cells were found in increasing abundance in the vicinity of injured cardiomyocytes (16 h) and ultimately covered the wounds (48 h). Employing fluorescently labelled co-cultures, high magnification (200×) fluorescent microscopy images showed that instead of cells from the original primary culture (CM, red), FTM HUCPVCs (FTM, green) almost exclusively served as the building blocks to reconnect separated cardiomyocyte fields. Furthermore, it was evident that HUCPVCs initially (24 h) connected with, and covered, the wounded edges instead of attaching to cell-free surfaces. In time (48 h) HUCPVCs appeared to be expanded and reached the opposite side of the wound. Live imaging of injured cardiomyocyte co-cultures shows that pre-stained cardiomyocyte fields separated by incisions lose their synchronised contraction. Following administration of FTM HUCPVCs, the injured cultures reached critical abundance at the injury site, and they gradually connected the opposing sides of the wound. Following the reconnection, contraction waves begin to pass through the previously isolated fields.

It was found that FTM HUCPVCs transfer cytoplasmic content into rat cardiomyocytes in vitro. Functional integration of the implanted cells into the myocardium requires the establishment of functional interactions with cardiomyocytes. The non-transferable nature of CTG was confirmed by staining co-cultures for human nucleus specific marker (HuNu). CTO stain appeared in rat cardiomyocytes after 3 days of co-culture. Furthermore, only rat cardiomyocytes in direct contact with CTO-containing human cells showed dye uptake, suggesting that trans-membrane junctions may have formed.

It was observed that FTM HUCPVCs transfer mitochondrial content into rat cardiomyocytes in vitro. The observation regarding the transfer of cytoplasmic content from FTM HUCPVCs into rat primary cardiomyocytes in co-cultures raised the question of whether the transfer of such compounds has any physiological relevance. After 72 hours of co-culture, mitochondrial-associated signals derived from FTM HUCPVCs appeared in the cardiomyocytes (CM) that were in direct contact with integrated FTM HUCPVCs, suggesting direct cell-to-cell transfer of mitochondrial content.

FTM HUCPVCs were seen to have higher connexin43 expression than term HUCPVCs and BMSCs when co-cultured with rat cardiomyocytes. Direct cell-to-cell interaction and communication requires intercellular membrane channel complexes between connecting cells. Primary cardiomyocyte cultures were isolated from ventricular regions of rat pup hearts as described above. In primary culture, cardiomyocytes show strong staining for connexin43 (cx43). When separated by the non-cardiomyocyte cells found in primary culture (likely fibroblasts) cardiomyocytes demonstrated very few cx43 positive bridges between them. In contrast, co-cultures of first trimester (FTM) HUCPVCs with rat cardiomyocytes showed distinct puncta that appeared to connect the cardiomyocyte cells. Under the same conditions, term HUCPVC co-cultures contained similar puncta, but to a lesser degree. Whereas with BMSC co-cultures puncta were not observed. Flow cytometric analysis was performed on co-cultures to quantify the proportion of cx43-positive human cells (TRA-1-85+, cx43+ double positive cells). The three types of human MSCs from co-cultures (1 week) showed different ratios of positivity for cx43. When comparing the extent of staining, FTM HUCPVCs showed the highest ratio of cx43+ cells (30%) when compared to term HUCPVCs (21%) and BMSCs (12%). The amount and distribution of cx43 signal suggests that gap junctions are responsible for the observed cellular content transfer between FTM HUCPVCs and cardiomyocytes, and the resynchronisation of separated cardiomyocyte fields.

FTM HUCPVCs were seen to integrate with developing endothelial networks and results in higher network growth when compared to other MSCs in rat aortic ring assay. Pre-stained (CTG, CellTrackerGreen™) suspensions of human MSCs were administrated to developing endothelial networks of ex-vivo cultured rat aortic rings in order to observe cell integration and effect on network growth. CTG-positive cells were imaged within the network 24 h after cell administration. FTM HUCPVCs appeared to preferentially associate with the peripheral, developing areas of the endothelial networks and displayed an elongated morphology. In contrast, term HUCPVCs and BMSCs showed little site preference and also localized within areas with minor tube formation.

Total network growth was calculated as the distance between the first proximal closed network loops near the aortic ring and the most distal closed loop. The mean radial size of networks co-cultured with MSCs were as follows: FTM HUCPVCs 2.9±0.3 mm, term HUCPVCs 2.2±0.5 mm, BMSCs 1.7±0.3 mm (n=3 for each condition). Untreated rings developed endothelial networks with a mean radius of 2.4±0.5 mm. Statistical comparison of MSC treatment groups showed that FTM HUCPVCs resulted in significantly increased network growth compared to term HUCPVC (ps0.05) and BMSC co-cultures (ps0.01). Untreated endothelial cultures expressed significantly greater network growth when compared to BMSC co-cultures (ps0.05).

Regarding network structure analyses, the average number of total closed loops in FTM HUCPVC-treated aortic ring networks (70±43) was significantly higher than term HUCPVCs (29±12) and BMSCs (24±2) (ps0.05). Untreated rings (79±14) displayed similar loop numbers compared to FTM HUCPVC co-culture conditions, but was significantly higher than those of either term HUCPVC or BMSC treated networks (ps0.01).

Implantation of FTM HUCPVCs in a rat model with MI leads to diminished scar tissue formation, greater cell retention, increased vascularisation and significant improvements in cardiac function when compared to term HUCPVCs or BMSCs.

Two weeks after cell injection, hearts were sectioned and tissue was analyzed for fibrotic tissue content at the level of ischemic injury. Mean scar tissue mass proportion to normal tissue in FTM HUCPVC, term HUCPVC and BMSC-treated hearts was 15±9%, 18±10%, and 36±9% respectively. Fibrotic tissue was significantly decreased in FTM HUCPVC when compared to BMSC-treated hearts ($p<0.05$).

Fluorescent microscopy images showed a higher frequency of AluIIb+(human) nuclei in the scar tissue regions of the FTM HUCPVC-treated post-MI rat hearts compared to term HUCPVC- and BMSC-treated samples. Human cell content of ischemic rat hearts was quantified by genomic qPCR for AluIIb and correlated to scar tissue content. Hearts treated with FTM HUCPVCs after MI showed significantly higher human nuclear DNA content when compared to term HUCPVCs and BMSC-treated hearts post-MI ($p<0.05$) and showed an inverse relationship with the amount of fibrotic tissue.

HUCPVCs show low immunogenicity when isolated from rat heart 2 weeks after administration.

Two weeks after injection 55% and 65% of the TRA-1-85high (human) cells isolated from FTM and term HUCPVC-treated rat hearts were found to express HLA-A, while 25% and 20% expressed of FTM HUCPVCs and term HUCPVCs expressed HLA-G, respectively. This indicates low immunogenicity even after 2 weeks in the myocardial niche. The number of TRA-1-85high (human) cells within cardiac tissue after treatment with BMSCs was below the amount required for immunophenotypical analysis (data not shown).

It was found that FTM HUCPVC treatment improves vascularisation of the ischemic myocardium after MI. Fluorescent isolectin (IB4) was utilized as an endothelial-specific probe in myocardial tissue sections to reveal blood vessel abundance and distribution in the ischemic heart muscle. As described above, fluorescent microscopy images were quantified for number and size of IB4-positive entities (capillaries). Vascular density of the ischemic myocardium was significantly higher ($p<0.01$) in FTM and term HUCPVC treated hearts compared to untreated (MI only). BMSC treatment did not result in a significantly increased capillary density. Median area of blood vessel cross-sections was the highest among the 3 cell types after FTM HUCPVC treatment and was significantly higher ($p<0.01$) than in BMSC treated hearts, but not different than untreated MI vessels.

It was found that FTM HUCPVC treatment leads to significant functional improvement after MI. Cardiac output of the animals (Foxrun rats) in every treatment group was assessed by echocardiograpy. Functional improvements in cardiac output at 2 weeks post-intramyocardial cell implantation were observed in rat models of MI with all three cell types when compared to those with media injection. However, left ventricular internal dimension (LViDs) was significantly lower in animals treated with FTM HUCPVCs, but not the other 2 cell types ($p<0.01$ and fractional shortening (% FS) was significantly higher in FTM HUCPVC-treated animals, compared to untreated ($p<0.01$).

FTM HUCPVC treatment was found to induce sustained functional improvements in a mouse model of MI for up to 6 months. In an in vivo study, FTM and term HUCPVCs were implanted acutely into an immunocompromised (NOD scid) mouse model of MI. Echocardiography showed that FTM HUCPVCs have an increased ability to restore heart function following MI when compared to term HUCPVCs. Ejection fraction and fractional shortening was significantly higher, while left ventricular internal diameter was significantly lower in FTM HUCPVC-treated animals when compared to those treated with term HUCPVCs, respectively. These effects are apparent as early as 2 weeks following MI and are sustained for up to 6 months. Endpoint histology analysis on post-MI mouse hearts six weeks after administration showed that scar area is significantly lower and scar thickness is significantly higher in HUCPVC-treated hearts compared to media controls ($p=0.05$). Further analysis of FTM and term HUCPVC-treated experimental groups showed that these physical improvements are significantly increased in FTM HUCPVCs when compared to term HUCPVCs ($p<0.05$). The functional improvement of HUCPVC-treated post-MI mouse hearts was sustained up to 6 months after administration with FTM HUCPVCs maintaining higher ejection fraction and fractional shortening and lower left ventricular dimension than term HUCPVCs ($p<0.05$). This sustained effect can be a crucial advantage in large animal models of longer life-span.

Discussion

The ultimate goals of a successful regenerative cell therapy for congestive heart failure is clear from a functional and histological aspect. However, the underlying cellular mechanisms required to achieve this are multifaceted and complex in nature. While a candidate cell type may have beneficial effects on one or more aspects of the regenerative process (eg proliferation, immunomodulation, and remodelling), only cell types capable of fulfilling all aspects of tissue repair would be optimal for cell therapy. Pericytes are localized around blood vessels in every tissue of the human body and have a crucial role in blood vessel formation and support, as well as controlling transport mechanisms between the tissue constituent cells and their circulation. The regenerative importance of pericytes and pericyte-derived MSCs is becoming increasingly evident. Term HUCPVCs could contribute to neoangiogenesis, endogenous cell recruitment, and immunomodulation. Although other groups have shown that term HUCPVCs displayed induced expression of cardiac-related marker expression in vitro, the same studies did not find a significant change in scar tissue formation or cardiac function in an in vivo MI model, suggesting the absence of significant tissue remodelling using these cells. Cell therapy applied either locally or systemically requires that the administered cells home preferentially to sites of injury; thus a successful cell therapy candidate should possess or develop such ability. As shown herein, assessment of in vitro cell invasion demonstrated that FTM HUCPVCs are attracted towards injured cardiomyocytes, and actively migrate through basal membrane-like barriers. Term HUCPVCs did not display this capacity and BMSC migration was inhibited by the proximity of injured cardiac cells.

After cardiac injury, the disruption of functional intercellular connections due to cell loss or separation by pathological ECM often leads to akinetic or arrhythmic tissue. Functional restoration of the myocardium necessitates the reestablishment of cell-cell connections. The observed appearance of cx43-positive puncta on the FTM HUCPVCs between rat cardiomyocytes in co-cultures and the transfer of gap junction permeable fluorophores, suggest functional intercellular connections. Induction of the major gap junction protein, connexin43, in co-cultures of stem cells and cardiomyocytes may improve intercellular signaling and progressively increase conductivity. The reconnection of separated cardiomyocyte fields as seen herein suggests that electrophysiological connections are established between FTM HUCPVCs and rat cardiomyocytes. In order to avoid fibrillations and arrhythmia in vivo, implanted cells are required to inherently possess or develop such features. From the current data, it is apparent that FTM HUCPVCs could serve as supporting cells in vivo after MI, in part by helping to restore cardiac tissue conductance.

Healthy heart tissue has the highest oxygen consumption compared to any other organ in the human body, both in resting state (8 ml $O_2$/min per 100 g) and during exercise (70 ml $O_2$/min per 100 g). This intense aerobic metabolism requires a high number of functional mitochondria (~5000 per cardiomyocyte) which decreases with age in mammals. Mitochondrial impairment in the heart muscle is a component of many cardiac pathologies and is often a therapeutic target. It has been reported that mesenchymal stromal cells have the potential for cell to cell support and regeneration of mitochondria and in particular, MSCs can regenerate the mitochondria of ischemic cardiomyoblasts. In this Example, it was observed an intense transfer of mitochondria-associated fluorophores from FTM HUCPVCs into primary cardiomyocytes in co-cultures, within 4 days of co-cultures. This most likely represents intercellular transfer of mitochondria from FTM HUCPVCs into cardiomyocytes. A less likely, but possible explanation is the transfer of FTM HUCPVCs mitochondrial content through gap junctions, which is subsequently taken up and accumulated in the recipient cardiomyocyte's mitochondrial compartment. This may be another mechanism by which FTM HUCPVCs could potentially support cardiac tissue repair.

In the rat aortic ring assay, FTM HUCPVCs showed the highest interaction with endothelial networks and supported the development of endothelial networks more than term HUCPVCs and BMSCs. The radial growth of the in vitro Matrigel™-embedded rat aortic ring endothelial network appeared to be the combined result of endothelial cell proliferation and elongation and the capability of the tubular network to remodel the surrounding extracellular matrix. Conditions resulting in higher radial growth of endothelial cell populations suggest a higher tissue penetration rate when translated to in vivo models.

Besides the rate of radial network growth, the network structure of the emerging neo-vasculature must be optimal for efficient tissue regeneration. A higher number of closed loops in a functional capillary network would result in a higher perfusion rate, within a given tissue area. Higher radial growth combined with higher number of closed loops in the FTM HUCPVC treatment group in vitro, could translate into higher surface coverage of an endothelial network in vivo. This is consistent with the in vivo observation that vasculature in the scar tissue of FTM HUCPVC treated ischemic hearts significantly improved compared to an untreated animal after MI. Importantly, FTM HUCPVCs were found in the scar tissue in the highest amount compared to term HUCPVCs and BMSCs, and the human cell abundance showed a reverse correlation with the extent of fibrotic tissue. Assuming that during the 1 week between MI induction and cell implantation the majority of vascular degradation has run its course in the ischemic myocardium, it also has to be considered that higher vascular density compared to untreated hearts can be, at least in part, due to neovascularization. This neovasculature must also be of perfundable diameter, thus only the combined effect of increased number and an increased, or maintained, blood vessel size would be able to achieve a functional vascular regenerative effect. From the observations made in this Example on the three cell types examined, it appears that FTM HUCPVCs would likely be the best candidate to accomplish this type of vascular regeneration and provide adequate reperfusion in a clinical setting. It was notable to observe that the highly promising results observed in vitro, together with the histological changes observed in vivo that FTM HUCPVCs—as opposed to term HUCPVCs and BMSCs—translated into a significant functional regenerative effect on post-MI hearts 2 weeks after administration. Furthermore, HUCPVCs isolated from rat hearts also showed a favourable immunological phenotype, suggesting that in vivo integration does not compromise their immune-privileged nature, and may augment their retention for a longer period of time. In an immunocompromised mouse model of MI, the FTM HUCPVCs' beneficial effect was sustained for up to 6 months.

Extended retention of FTM HUCPVCs in the infarcted heart can be sufficient for their superior regenerative mechanisms to act and have provide sustained beneficial effects necessary in pre-clinical and clinical scenarios alike.

In summary, FTM HUCPVCs have in vitro properties consistent with a cell type that could be effective for cell therapy post MI. These properties were enhanced when compared to term HUCPVCs or BMSCs. In concert with this, they exhibited sustained and superior functional improvement in rodent in vivo models, as compared to the other older MSC sources tested. Therefore, FTM HUCPVCs are a promising new candidate for regenerative cellular therapy after MI.

Example 6

First Trimester Human Umbilical Cord-Derived Perivascular Cells Have Advantageous Regenerative Potential Summary First trimester human umbilical cord-derived perivascular cells (FTM HUCPVCs) obtained and treated as described herein (the "subject cells") exhibit superior characteristics in support of their regenerative potential. Employing the subject human umbilical cord perivascular cells (HUCPVC) from fetal tissue obtained in first trimester (FTM) has the following advantages versus other sources of cells in regard to following characteristics: (i) increased rate of cell growth; (ii) improved plasticity for cell differentiation; (iii) superior ability to generate myocardium; (iv) improved adaptation to stresses; (v) better regenerative immunomodulation; (vi) increased angiogenic properties; and (vii) improved in vivo heart function.

(i) Increased Rate of Cell Growth. An increased rate of cell growth was observed in the subject cells versus similarly isolated full term (or "term") cells. The expansive capacity and molecular characteristics of the subject first trimester (FTM) human umbilical cord perivascular cells (HUCPVC cells) obtained at less than 13 weeks of gestation are more amenable to cell therapy for treating cardiovascular injury or heart disease as compared with full term counterpart cells or other sources of MSC.

An increased rate of cell growth in regard to faster population doubling time has been observed. This faster doubling time leads to more cells for use in treatment purposes, such as for transplantation in a subject, at any given passage number between passages 2 and 10. PDT (doubling time) and accumulated cell numbers significantly improved.

(ii) Improved Plasticity for Cell Differentiation. An improved plasticity for cell differentiation, and specifically in the frequency of freshly isolated cells expressing the pericyte-associated marker CD146 as compared with full term cells has been observed. These pericyte-like properties are associated with regenerative potential of mesenchymal stem cells (MSC). First term (FTM) versus full term (TERM) cell comparisons were made, and the CD146 values were observed as follows: FTM 73.0+/−2.2 versus TERM 15.8+/−0.6, indicating greater expression of the CD146 marker.

Improved plasticity for cell differentiation in the subject cells has also been observed versus TERM cells in respect of an increased frequency of cells expressing SOX17 in cultured FTM HUCPVC. Observations based on FACS histograms for SOX17 and FGFR1 expression in undifferentiated FTM-PVCs (n-3) and TERM-PVCs (n-3) established an expression of 9.02% SOX17 for the subject FTM HUCPVC cells versus 0.03% for TERM cells. SOX17 is required for mesoderm cardiomyogenic specification in embryonic stem cells and will thus render a subpopulation of FTM (less than 13 weeks gestation) HUCPVC more amenable to differentiate into cardiomyocytes versus TERM cells.

Improved plasticity for cell differentiation was also observed in terms of an increased frequency of pluripotency marker Oct4A+ve cells in cultured first term cells from less than 13 weeks of gestation (FTM) HUCPVC when compared to TERM—HUCPVC. This observation was made with cell staining and photomicrograph assessment of cells for OCT4A staining. A striking improved/increased cell differentiation potential was observed in FTM-HUCPVC (Oct4A+ of: 87.4+/−2.2) cells when compared to full term HUCPVC cells (Oct4A+ of: 0.7+/−0.2).

(iii) Superior Ability To Generate Myocardium. The subject cells displayed a superior ability to generate myocardium, as well as improved plasticity for overall cell differentiation. Advantages of FTM (less than 13 weeks gestation) HUCPVC over TERM counterparts or other sources of MSC (with a focus on properties that are relevant for treating cardiovascular injury or heart disease with regard to regeneration) were established. Parameters of increased plasticity for differentiation towards many cell lineages are also observed in the subject cells.

A superior ability to generate myocardium versus TERM-PVCs, based on cardiomyocyte-like cell data was observed based on bright field micrographs of live cells at the end of differentiation, and immunofluorescence cytochemistry micrographs in a Transwell assay. This was observed for α-SA and cTnT in cells co-cultured with rat neonatal cardiomyocytes. Cardiomyogenic transdifferentiation rates showed improvement. The subject cells have showed a superior ability to generate myocardium based on FTM HUCPVC differentiation data showing the subject cells differentiate into cardiomyocyte phenotype in vitro when subject to the described method. Rat primary cardiomyocytes, FTM HUCPVC cocultures costained with human nuclear antigen- (HuNu-) specific and alpha-sarcomeric actinin- (aSarc-) specific antibodies were assessed using DAPI: nuclear stain; HuNu aSarc; and an overlay of DAPI+ HuNu aSarc, confirming this observation.

(iv) Improved Adaptation To Stresses. Improved adaptation to stresses was observed in the cells isolated according to the described methods. Advantages were observed in FTM (cells from tissue obtained at less than 13 weeks of gestation) HUCPVC as compared with full TERM counterparts or other sources of MSC (with a focus on properties that are relevant for treating cardiovascular injury or heart disease). The subject cells illustrated unique adaptability regarding upregulation of secretome properties, and increased resistance in stress conditions relevant to myocardial infarction (ischemia, glucose deprivation). Further, superior glucose data of cells from less than 13 weeks gestation (FTM), versus full TERM cells supported the improved adaptation to stress. Chemical stress data affirms this benefit of cells from less than 13 weeks gestation. An improved profile for stress resistance is maintained over population doublings. This adaptation to stress offers substantial advantages in cell therapy applications for ischemic injuries, and in particular to treat cardiovascular injury or heart disease.

(v) Better Regenerative Immunomodulation. Improved regenerative immunomodulation over full TERM cells so treated was observed. The advantages of this observation for FTM HUCPVC over full TERM counterparts or other sources of MSC regarding these properties is relevant for treating cardiovascular injury or heart disease. Improved immunomodulatory properties are pertinent for heart repair after myocardial infarction. Better regenerative immunomodulation in the subject cells versus bone marrow MSCs (BMSCs) was observed in regard to post-differentiation into cardiomyocyte with the subject cells resulting in less immunogenicity than observed with TERM and with BMSCs.

Improved regenerative immunomodulation in the subject cells was observed when transplanted into rodent heart with myocardial infarction. In this model, the subject cells altered the phenotype of macrophages towards an anti-inflammatory phenotype. The cells obtained according to the subject method displayed this advantage, and were less likely to induce an immunogenic reaction when used in the treatment of cardiovascular injury or heart disease.

(vi) Increased Angiogenic Properties. Increased angiogenic properties were observed in the subject cells, which provides an advantage in using first term (FTM) cells from umbilical cord from fetal tissue obtained at less than 13 weeks of gestation (HUCPVC) over TERM counterparts or other sources of MSC, such as bone marrow MSC, when treating cardiovascular injury through cardiovascular regeneration. These superior angiogenic properties were observed in the subject cells exhibiting pericyte-like cell properties as compared with TERM and BMSC cells. Further, the subject cells promoted increased angiogenesis, when present alone or in combination with endothelial cell types, as observed in an in vitro aortic ring assay.

Increased angiogenic properties in the subject cells were illustrated by the subject cells' increased angiogenesis in the heart following myocardial infarction when compared to TERM and BMSC. FTM HUCPVCs exhibited benefits over full TERM counterpart cells or BMSC in cardiovascular regeneration and increased tissue remodeling properties. FTM HUCPVC treatment resulted in less scar tissue formation after myocardial infarction (MI) compared to other sources of MSC (TERM and BMSC). Masson's Trichrome staining was conducted on post-MI, MSC-treated hearts showed differences in scar size normalised to section surface. Images were taken of the MI-affected ventricular region and assessed for area. The proportion (%) of fibrotic tissue attributable to each cell type treatment was observed, with FTM cells exhibiting significantly less at 8.9% versus TERM (25.5%) and BMSC (29.7%).

(vii) Improved In Vivo Heart Function. The subject cells improve in vivo heart function. FTM HUCPVC have advantages over term counterparts or other sources of MSC with regard to properties that are relevant for cardiovascular regeneration, treating cardiovascular injury and treating heart disease. Subjects treated with the subject cells show improved cardiovascular regeneration upon treatment of cardiovascular injury and heart disease. The subject cells contributed to better functional recovery in rodent models of myocardial infarction (coronary artery ligation) treated with the subject FTM HUCPVC when compared to other MSC sources, such as TERM and BMSC. FTM HUCPVCs improved heart function after MI versus TERM and BMSC as observed by functional assessment of human MSC treated post-MI rat hearts. FTM (<13 weeks gestation) HUCPVCs, term HUCPVCs and BMSCs were implanted into rats 1 week after permanent coronary artery ligation. Echocardiography was performed 2 weeks after cell administration. Myocardial contractility and cardiac output was observed as left ventricular internal systolic diameter (LVIDs) and fractional shortening. While improvements were observed for all three MSC types compared to no cell infusion (MI only+media), LVIDs was significantly lower only for FTM HUCPVC and fractional shortening was significantly improved for FTM HUCPVC (n=6, p<0.5), whereas no significant difference was seen for BMSC or TERM groups.

The subject cells improved in vivo heart function by inducing cardiac improvement that was sustained up to 6 months post MI. The heart function of MSC treated mouse hearts was observed in a 6 months study. Animals were treated with either FTM HUCPVC or TERM cells following a myocardial infarction (MI) event in the model. A reduction of ventricular dilatation (left ventricular diastolic internal distance, LVDD) was observed in the by the implantation of FTM versus TERM, and the superiority of FTM cells was maintained over 6 months following myocardial infarction. Improvement in percent ejection fraction and fractional shortening in hearts implanted with FTM versus TERM HUCPVCs was also established and sustained over 6 months after MI. Thus, cardiac function was improved by treatment with FTM HUCPVC implantation compared to TERM.

Example 7

Reprogramming of FTM-HUCPVCS Into Induced Pluripotent Stem Cell Lines And Characterization of Their Tri-Lineage Derivatives First trimester human umbilical cord-derived perivascular cells (FTM HUCPVCs) can be utilized in vascular and regenerative medicine. This example shows that reprogrammed induced pluripotent stem cells (iPSCs) from first trimester human umbilical cord perivascular cells (FTM-HUCPVCs) demonstrate tri-lineage differentiation potential in 2-D and 3-D cultures. Successful reprogramming of HUCPVCs into iPSCs and their tri-lineage differentiation into endodermal, mesodermal, and ectodermal derivatives is described herein.

Using a non-genome integrative reprogramming vector, this platform has generated four human induced pluripotent stem cell (hiPSC) lines from two male and two female FTM-HUCPVC parental cell lines (i.e. FTM-iPSCs). Reprogrammed iPSCs were assessed to retain the normal karyotype of their corresponding parental cell, while expressing the distinct immunophenotype of pluripotent cells. The absence of a genomic footprint avails these FTM-iPSCs to subsequent genetic manipulation (i.e. CRISPR-Cas), to delineate the effect of specific genes against isogenic controls, thereby negating result disparity arising from genetic diversity.

Characteristic of pluripotent cells, these generated FTM-hiPSC lines' ability to undergo indefinite self-renewal circumvents the limitation of eventual cellular senescence in parental FTM-HUCPVCs following successive culture passage. Moreover, FTM-iPSC lines have also demonstrated their ability to undergo both spontaneous and directed tri-lineage differentiation in vitro. These include, but are not limited to differentiation into neural, vascular and pulmonary cell types, representative of the ectodermal, mesodermal and endodermal germ layers, respectively. Notably, directed differentiation into all cell types did not necessitate direct or indirect cultures with primary mammalian cell types or animal-derived feeder layers, which could potentially confound subsequent result interpretation. This has direct implications for the downstream use of FTM-iPSC derived cells in 2-D and 3-D cultures to investigate early stages of human fetal development, as well as, a high-throughput platform for disease modeling and drug screening. The parental origins of these FTM-iPSCs afford a further opportunity to investigate the effect of sex difference in disease development and drug response. Differentiated derivatives of FTM-iPSCs have been used in isolation or employed as "assembloids". The latter may be subjected to a number of combinations to increase the complexity and maturity of resultant organoid, which better recapitulates fetal organ development. An extension of the assembloid technology/approach, is the use of their secretome either in isolation (i.e. cell-free therapy) or in combination with other cells to enhance repair and/or regeneration efforts.

Materials and Methods

All experimental studies were performed with Veritas independent research ethics board approval (REB No. 16540, per Appendix IX, Sub-study 5). Medium and associated culture/enrichment reagents were sourced from ThermoFisher Scientific, Stemcell Technologies. Small molecules used in differentiation studies were sourced from Biotechne, Stemcell Technologies and Sigma-Aldrich. Antibodies used in characterization studies were sourced from Miltenyi biotec, Abcam, Cell Signaling Technology, and ThermoFisher Scientific.

Established lines of early passaged (passage 2-5) male and female FTM-HUCPVC lines were plated in HUCPVC culture media composed of alpha-MEM, human platelet lysate (HPL), penicillin-streptomycin cocktail; and maintained under normoxic growth conditions henceforth defined as 37° C., 21% $O_2$, 5% $CO_2$. The maintenance medium was replaced every 3 days.

When the FTM-HUCPVC cultures reached 85% confluence, they were harvested and replated on a tissue culture-treated 6-well plate coated with hESC-Qualified Matrix at $5\times10^4$ cells/well. This step may comprise: washing the FTM-HUCPVCs with PBS; adding Trypsin-EDTA (0.25%); harvesting the cells in a tube, centrifugation at 300×g for 5 minutes, and mixing the cells in fresh culture media. The cells were maintained under normoxic growth conditions for 24 hours.

Reprogramming of FTM-HUCPVCs with ReproRNA Mixture. The culture media was aspirated from the culture dishes and the cultures rinsed once with PBS before replacing with 1 ml of warmed Growth Media per well of the 6-well plate; and maintained for 20 minutes in normoxia. The Growth Media is composed of Advanced DMEM, FBS, 200 mM L-Glutamine, and recombinant B18R protein (175 ng/ml). ReproRNA mixture composed of an RNA replicon vector containing reprograming factors: OCT-4, KLF-4, SOX-2, GLIS1, and c-MYC, Opti-MEM reduced-serum medium, transfection supplement and transfection reagent; the mixture was added to each well containing FTM-HUCPVCs. The cultures were maintained under normoxia for 24 hours.

In the first 5 days post-transfection, the media was aspirated from each well and replaced daily with fresh Growth Media containing puromycin (0.8 pg/ml). On day 6, the cells were cultured in Growth Media without puromycin for 48 hours. From day 8-15, the cells were maintained in Repro-TeSR™ media containing B18R with media changes performed daily. Day 16 onwards, the cells were cultured in ReproTeSR™ medium alone until the emergence of iPS colonies. Post-transfection, all cultures were maintained under normoxic growth conditions.

Putative iPS colonies were manually isolated and dissected into fragments using a 22-25-gauge needle. The fragments were added to a tube containing fresh mTeSR™ medium and Rho kinase inhibitor (8 µM) and immediately replated on culture plates coated with Matrigel®; maintenance under normoxia for 24 hours. Fresh daily media changes were performed to sustain the cells in an undifferentiated state. The PS colonies were passaged when the density reached 70%-85% of the surface by repeating the same manual isolation procedure.

Cryopreservation of iPS Colonies. This step may comprise: washing the iPSCs with PBS; adding Trypsin-EDTA (0.25%); harvesting the cells in a tube, centrifugation at 300×g for 5 minutes, and mixing the cells in CryoStor® animal-component free cell preservation medium. 1 ml of cell mixture was transferred to pre-chilled cryovials in Nalgene™ freezing box before storage in a −80° C. freezer for 24 hours. For long term storage, the frozen cells were transferred to liquid nitrogen.

Thawing and Restoration of the iPS Colonies to Viability. The cryovial containing frozen PS colonies was removed from the liquid nitrogen tank and thawed quickly at 37° C. Thawed cells were transferred into fresh tubes and centrifuged at 250×g for 5 minutes. The cells were resuspended in media composed of mTeSR and Rho kinase inhibitor (8 µM), and replated on matrix-coated plates. The cultures were maintained under normoxic growth conditions for 24 hours prior to the replacement of the culture media with fresh mTeSR™ medium.

Characterization of Generated iPS Lines. A random selection of PS clones from each line were submitted for genetic testing for chromosomal aneuploidy screening and copy number variation using in-house next generation sequencing (NGS) technology. The pluripotent state of newly generated PS clones was visualized using light microscopy in accordance with conventional pluripotent morphology; defined as: compact colony morphology, with well-defined borders, and cells exhibiting high nucleus-to-cytoplasm ratio; and confirmed by expression of a panel of flow cytometric markers. The pluripotent potential of each line (passage-matched) was evaluated using diverse and distinct tri-lineage differentiation strategies.

Differentiation of iPSCs into Endodermal Pulmonary Lineage Cells. The multi-step procedure involved primitive streak formation, definitive endoderm induction, anterior foregut endoderm induction, lung progenitor induction and expansion, lung epithelium maturation and expansion occurred over 60 days. A serum-free differentiation medium composed of IMDM, Ham's F-12, BSA, GlutaMAX™, N2, B27, and penicillin/streptomycin was used as a basal culture medium. The concentration of supplements used is PS line-dependent.

Primitive Streak Formation. Human PS colonies were washed twice with PBS, dissociated with pre-warmed 0.05% trypsin for 5 minutes, harvested and centrifuged at 250×g for 5 minutes. The cell pellet was resuspended in basal medium supplemented with Rho kinase inhibitor (8 µM), Wnt3a (10-20 ng/ml), and BMP-4 (5 ng/ml) and placed in ultra-low attachment plates to form embryoid bodies (EBs). The cultures were maintained under hypoxic conditions defined as 37° C., 5% $O_2$ for 24 hours.

Definitive Endoderm (DE) Induction. EBs were collected in a fresh tube and pelleted at 150×g for 1 minute. They were then resuspended in fresh basal medium supplemented with Rho kinase inhibitor (5 µM), Activin A (100-125 ng/ml), BMP-4 (0.8 ng/ml), and FGF-2 (3 ng/ml). The cultures were maintained under hypoxic conditions for 48 hours. Fresh supplemented medium was replaced every 2 days for a total of 5 days.

Patterning of Anterior Foreqgut Endoderm (AFE). EBs were collected in a fresh tube and warmed trypsin (0.05%) added, the tube was flicked with appropriate force to dissociate them completely. The cells were centrifuged at 300×g for 5 minutes at 4° C. They were then resuspended in fresh basal medium supplemented with dorsomorphin dihydrochloride (1.5 µM) and SB431542 (8-10 µM). The cells were replated on fibronectin-coated surfaces and maintained at 37° C., 5% $O_2$ for 24 hours. Fresh supplemented medium was replaced every day for a total of 2 days before the medium was switched to one supplemented with IWP-2 (1-2 µM) and SB431542 (8-10 µM) for a further 2 days in hypoxia.

Induction of Lung Progenitors (LPs) and Expansion. The AFE medium was aspirated and replaced with fresh basal media supplemented with a Wnt agonist (3 µM), FGF-7 (10-15 ng/ml), FGF-10 (10-15 ng/ml), BMP-4 (8-12 ng/ml), EGF (10 ng/ml) and retinoic acid (50 nM). The cells were maintained in hypoxia. Fresh supplemented medium was replaced every 2 days for a total of 10 days. Once the cultures reached 85% confluence, they were replated on fresh fibronectin-coated plates. Following 8 days, the media was aspirated and replaced with fresh basal media supplemented with a Wnt agonist (3 µM), FGF-7 (10-15 ng/ml) and FGF-10 (10-15 ng/ml). The cultures were maintained under hypoxic conditions. Fresh supplemented medium was replaced every 2 days for a total of 12 days.

Derivation of Pulmonary Epithelium. The lung progenitor expansion media was aspirated and replaced with fresh basal media supplemented with a Wnt agonist (3-5 µM), FGF-7 (10-15 ng/ml), FGF-10 (10-15 ng/ml), BMP-4 (8-12 ng/ml), IBMX (0.05-0.1 mM), cAMP (0.05-0.1 mM), and dexamethasone (20 ng/ml). The culture hereafter was maintained in normoxic growth conditions. Fresh supplemented medium was replaced every 2 days for a total of 30 days. The cultures can be maintained for at least two months in this medium.

Enrichment of Pulmonary Lneage Cells. At specific milestones of pulmonary differentiation such as the induction of DE, and post-ventralization of AFE, the cells were magnetically labelled with antibodies targeted to various surface antigens and fluorochrome-labelled microbeads prior to the separation of cell fractions using the magnetic field of a MACs separator. The pulmonary surface antigens include but are not limited to CXCR4, carboxypeptidase M (CPM), and EpCAM. The enriched cells were replated within 15 minutes after the selection procedure and maintained under the appropriate growth conditions in accordance with their stage of differentiation. A further optional step includes the cryopreservation of enriched pulmonary epithelial cells in freezing medium and storage in liquid nitrogen.

Differentiation of iPSCs into Intermediate Mesodermal Renal Lineage cells. The procedure involving the induction of the primitive streak in 2-D cultures and the subsequent generation of 3-D kidney organoids occurred over a three-week period. The cultures were maintained under normoxic conditions. In the first step, PS colonies were washed with PBS, dissociated with Accutase®, centrifuged at 280×g for 5 minutes, resuspended in mTeSR™ media containing Rho kinase inhibitor (8 µM) and replated at a density of 3000-7000 cells/well pre-coated with Matrigel for 24 hours. The media was aspirated and replaced with mTeSR™ media supplemented with a low percentage of Matrigel to induce the formation of cavitated spheroids within 24 hours before culturing in fresh mTeSR™ medium for a further 24 hours. Induction of the primitive streak was achieved by aspirating the old media and replacing with STEMdiff™ kidney basal medium supplemented with SG growth factors. Following 36-40 hours, the late primitive streak was formed and the cells were cultured with STEMdiff™ kidney basal media containing DM growth factors. Fresh supplemented media changes were performed every 2-3 days depending on the confluence.

Differentiation of iPSCs into Lateral Plate Mesodermal Cardiac Lineage cells. The cardiac differentiation procedure differed with respect to 2-D and 3-D cultures, but was maintained under normoxic growth conditions. For 2-D cultures, iPS colonies were dissociated into single cells using Accutase and maintained in mTeSR™ medium supplemented with Rho kinase inhibitor (8 µM) for 24 hours. The medium was replaced daily with fresh mTeSR™ for a further 3-5 days. The cells were then cultured in basal RPMI/B27-insulin supplemented media (Wnt agonist (6-12 µM) or activin A (100-150 ng/ml)) for 24 hours. The media was then replaced with basal medium supplemented with IWP2/4 (5 µM) or BMP-4 (5-10 ng/ml) for 48 hours or 4 days, respectively. The cells were then maintained in RPMI/B27 medium for one week with medium changes every 2-3 days. For 3-D cultures, iPS cell aggregates previously treated with BIO for 3 days were cultured in ultra-low attachment plates overnight in RMPI medium supplemented with KnockOut™ serum replacement (20%) for 24 hours to form EBs. The EBs were cultured for a further 5 days in fresh RPMI supplemented with 20% HPL and the desired small molecules (as in 2-D culture). Following 12 days of differentiation, the EBs were cultured in RPMI media supplemented with 2% HPL. The plates containing 3-D organoids were placed on an orbital shaker (70 rpm) at 37° C.

Enrichment of Cardiac Lineage Cells. Following cardiac differentiation, metabolic selection was performed under normoxic growth conditions. The cells were cultured in enrichment medium composed of RPMI medium (without glucose) supplemented with sodium lactate for four to six days; fresh medium changes performed once every 2 days. Post-metabolic selection, the cells were cultured in maintenance media composed of RPMI/B27 medium. A further optional step includes the cryopreservation of enriched cardiomyocytes in freezing medium and storage in liquid nitrogen.

Differentiation of iPSCs into Cerebral Organoids. Differentiation into cerebral organoids was performed according to manufacturer's instruction as per STEMdiff™ Cerebral Organoid kit (Cat. No. 08570, StemCell Technology, Vancouver, Canada) which is a proprietary defined, serum-free cell culture media. FTM-iPSCs were harvested and grown as embryoid bodies for 5 days in Media A, prior to culture with Induction Media between days 5-7. Organoids were then embedded in hESC-qualified Matrigel and cultured with Expansion media from days 7-10 in an ultralow attachment 6-well plate. Thereafter, media change was performed once every 3-4 days with Cerebral Organoid Maturation Media.

Characterization of Differentiated iPSC-derived Cell Types. The morphologies of endodermal-, mesodermal- and ectodermal-lineage cells or 3-D organoids were visualized by light or fluorescent microscopy. Images were acquired at ×100 magnification (EVOS, LifeTechnologies). To quantify the protein expression of various markers associated with the specific lineage, cell cultures were washed twice with PBS, and dissociated with trypsin-EDTA (0.25%). The cell pellet was resuspended in 2% FBS and resultant cell suspensions incubated in the dark for 25 minutes at 4° C. with antibodies at dilutions according to the manufacturer's recommendations. Flow cytometry (FC) was performed with appropriate isotype controls using the MACSQuant® Analyzer 10 (Miltenyi Biotec) and results analyzed using FlowJo™ software (BD).

Sample Size and Statistical Analyses. The sample size for NGS technology was n=15 (3-4 clones per iPS line); n=4 iPS lines for each of the tri-lineage differentiation strategies. Where appropriate, statistical analyses were performed using the GraphPad Prism software. Unless stated otherwise, one-way ANOVAs and post-hoc tests such as Bonferroni's multiple comparisons test were performed to determine statistical significance (*$p<0.05$; #$p<0.01$).

Results

It was found that FTM-HUCPVCs could be successfully reprogrammed to generate iPS lines with multiple clones that were determined to be karyotypically normal (46, XX or 46 XY genotype) following subject to NGS testing (Table 1).

TABLE 1

Report: Genetic Testing for Aneuploidy and Copy Number Variation

| Sample # | Sample ID | Results | Interpretation |
| --- | --- | --- | --- |
| MH-1 | CELL-LINE-MH1-NextSeq | 46, XX | Euploid, female |
| MH-2 | CELL-LINE-MH2-NextSeq | 46, XX | Euploid, female |
| MH-3 | CELL-LINE-MH3-NextSeq | 46, XX | Euploid, female |
| MH-4 | CELL-LINE-MH4-NextSeq | 46, XX | Euploid, female |
| MH-5 | CELL-LINE-MH5-NextSeq | 46, XX | Euploid, female |
| MH-6 | CELL-LINE-MH6-NextSeq | 46, XX | Euploid, female |
| MH-7 | CELL-LINE-MH7-NextSeq | 46, XX | Euploid, female |
| MH-8 | CELL-LINE-MH8-NextSeq | 46, XX | Euploid, female |
| MH-9 | CELL-LINE-MH9-NextSeq | 46, XX | Euploid, female |
| MH-10 | CELL-LINE-MH10-NextSeq | 46, XX | Euploid, female |

TABLE 1-continued

Report: Genetic Testing for Aneuploidy
and Copy Number Variation

| Sample # | Sample ID | Results | Interpretation |
|---|---|---|---|
| MH-11 | CELL-LINE-MH11-NextSeq | 46, XX | Euploid, female |
| MH-12 | CELL-LINE-MH12-NextSeq | 46, XX | Euploid, female |
| MH-13 | CELL-LINE-MH13-NextSeq | 46, XY | Euploid, male |
| MH-14 | CELL-LINE-MH14-NextSeq | 46, XY | Euploid, male |
| MH-15 | CELL-LINE-MH15-NextSeq | 46, XY | Euploid, male |

Figure 19:
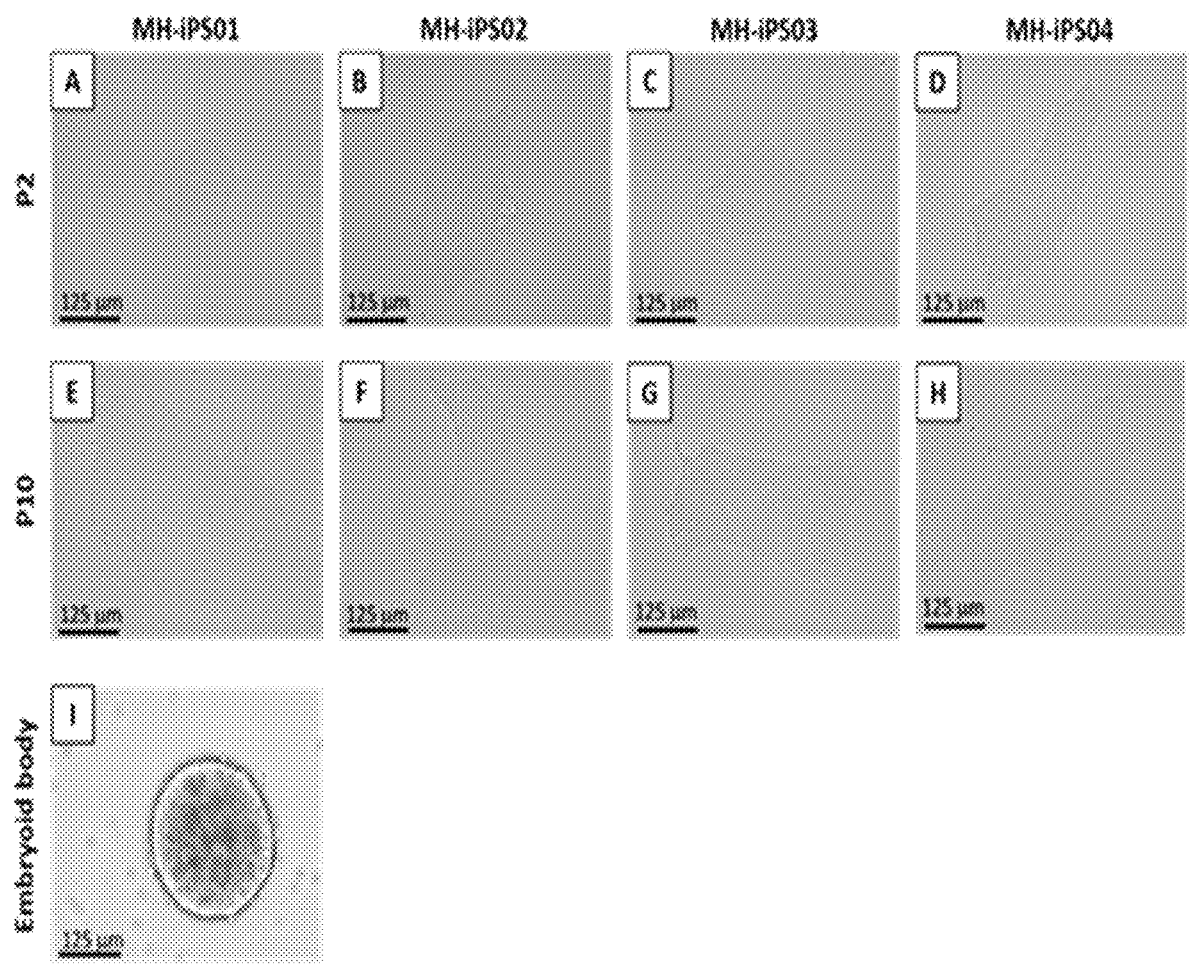
FIG. 19, in Panels A-H, depicts micrographs at 100× magnification showing representative iPS colonies from each line at early and later stage passage in 2-D culture; and Panel I shows representative embryoid body formed by 3-D aggregates of iPS cells.

FIG. 19, in Panels A-H, depicts micrographs at 100× magnification showing representative iPS colonies from each line at early and later stage passage in 2-D culture; and Panel I shows representative embryoid body formed by 3-D aggregates of iPS cells.

It was observed that all clones derived from the newly generated iPS lines retained pluripotent colony morphology similar to other pluripotent stem cells (e.g. embryonic stem cells) in published literature for at least 10 passages. This was evinced by their tight, compact structure, well-defined borders and high nucleus-to-cytoplasm ratio in 2-D cultures. The iPS lines also demonstrated equivalent ability to form 3-D embryoid bodies (FIG. 19).

Figure 20:
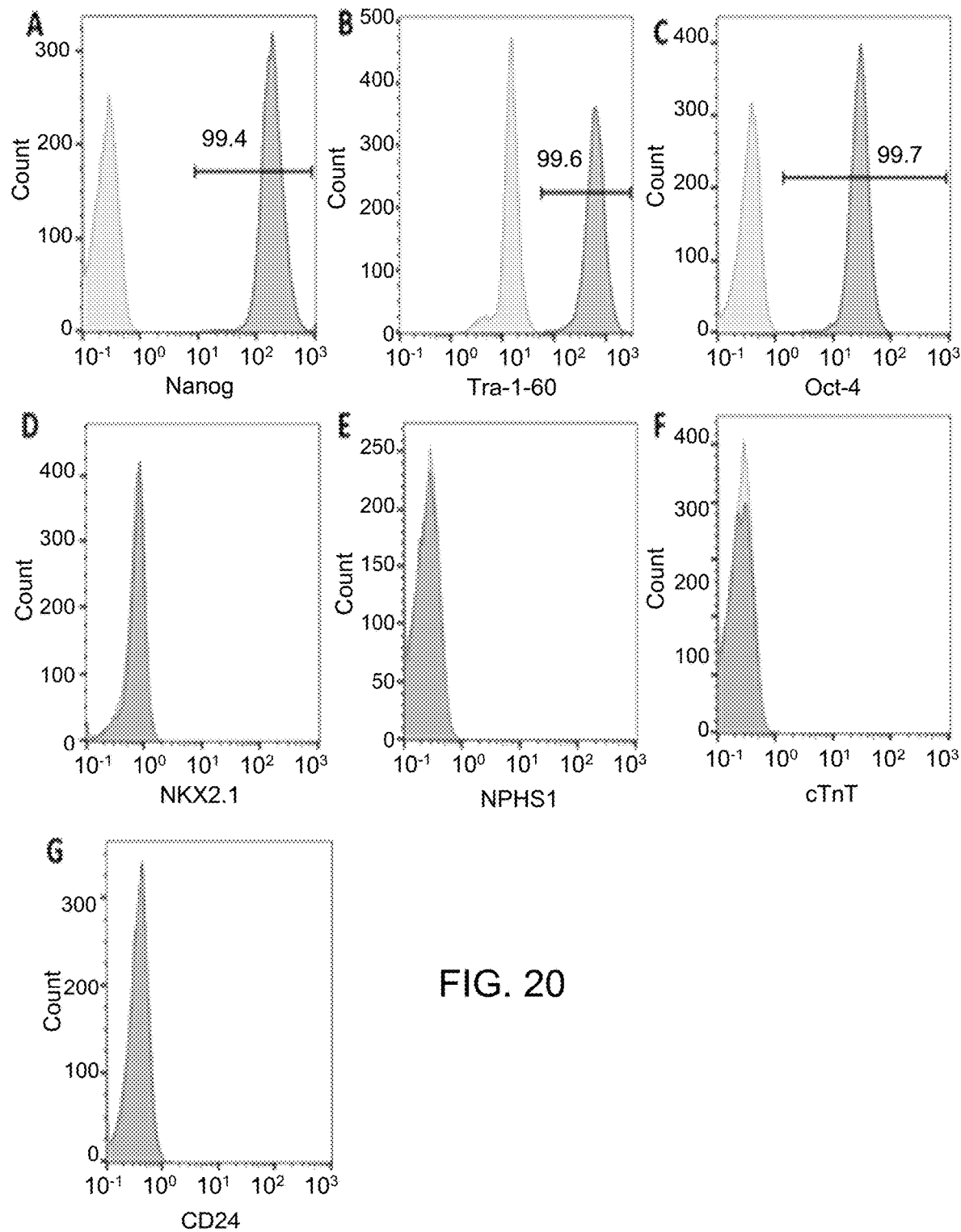
FIG. 20 shows, in Panels A-C, representative iPS flow cytometric plots of pluripotency-associated markers expressed by iPS lines; and in Panels D-G, representative flow cytometric plots are depicted of markers associated with differentiated cell types which are absent in iPS lines.

FIG. 20 shows, in Panels A-C, representative iPS flow cytometric plots of pluripotency-associated markers expressed by iPS lines; and in Panels D-G, representative flow cytometric plots are depicted of markers associated with differentiated cell types which are absent in iPS lines.

It was found that all reprogrammed iPS lines highly expressed pluripotent proteins such as Oct-4, Nanog, and Tra-1-60. It was also found that the same population did not exhibit expression of markers associated with pulmonary (NKX2.1), renal (NPHS1), cardiac (cTnT), or neural (0024) lineage cells. These results confirmed the pluripotent nature of the iPS lines (FIG. 20).

Figure 21:
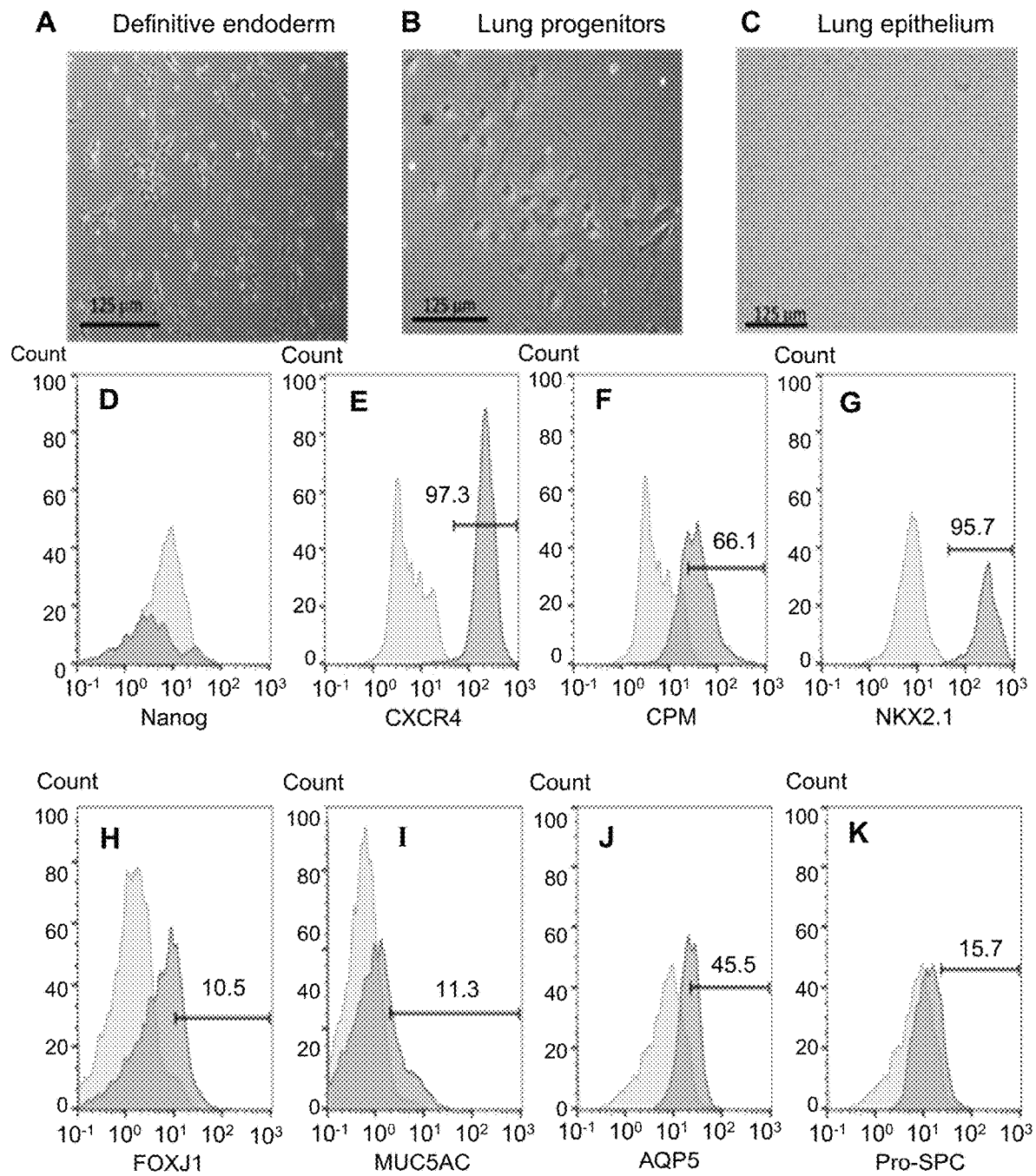
FIG. 21 shows micrographs in Panels A-C of iPS cells at milestones of pulmonary differentiation, taken at 100× magnification; Panels D-K depict representative flow cytometric plots at key stages.

FIG. 21 shows micrographs in Panels A-C of iPS cells at milestones of pulmonary differentiation, taken at 100× magnification; Panels D-K depict representative flow cytometric plots at key stages.

It was found that all iPS lines could be differentiated into endodermal derivatives including pulmonary lineage cells. Successfully differentiation was first observed by the dramatic downregulation of Nanog expression. Post-first stage of lung development (i.e. DE intermediate), all lines expressed a negligible percentage of the pluripotent marker. Concurrently, a high expression of CXCR4 in DE cells (95±3%) was observed. It was observed that the DE cells migrated away from the compact colony structure and adopted petal morphology, which progressively formed a uniformed monolayer within 5 days (FIG. 21. panels A, D, E).

It was found that post-ventralization of AFE, approximately 63±7% of LPs were generated as evidenced by FC quantification of CPM+ cells. Previously, CPM has been published as a surface marker to prospectively isolate LPs. Enrichment of CPM+ cells through magnetic labeling and subsequent FC analyses confirmed that the vast majority expressed NKX2.1 (>92±6%)—verifying that these are bona fide LP cells. Visually, the LPs appeared morphologically distinct from DE cells, revealing broad, flattened structures (FIG. 21 panels B, F, G).

It was found that expansion and maturation of LPs using combinations of small molecules generated a closely packed epithelium with minimal intracellular space between each cell, highly reminiscent of in vivo respiratory tissue. FC analyses of epithelial cells 45 days post-differentiation revealed that the heterogeneous nature of these cells. The cells expressed proteins found in both proximal and distal airways. The proximal markers, MUC5AC and FOXJ1, suggested the presence of a small proportion (<15%) of mucous secreting goblet cells as well as cells undergoing ciliogenesis, respectively, in the upper airways. Conversely, the presence of distal lung epithelium, responsible for forming the gas exchange interface, was noted by the positive expression of alveolar epithelial type I and II markers: AQP5 and pro-surfactant (pro-SPC) (FIG. 21 panels H-K).

Figure 22:
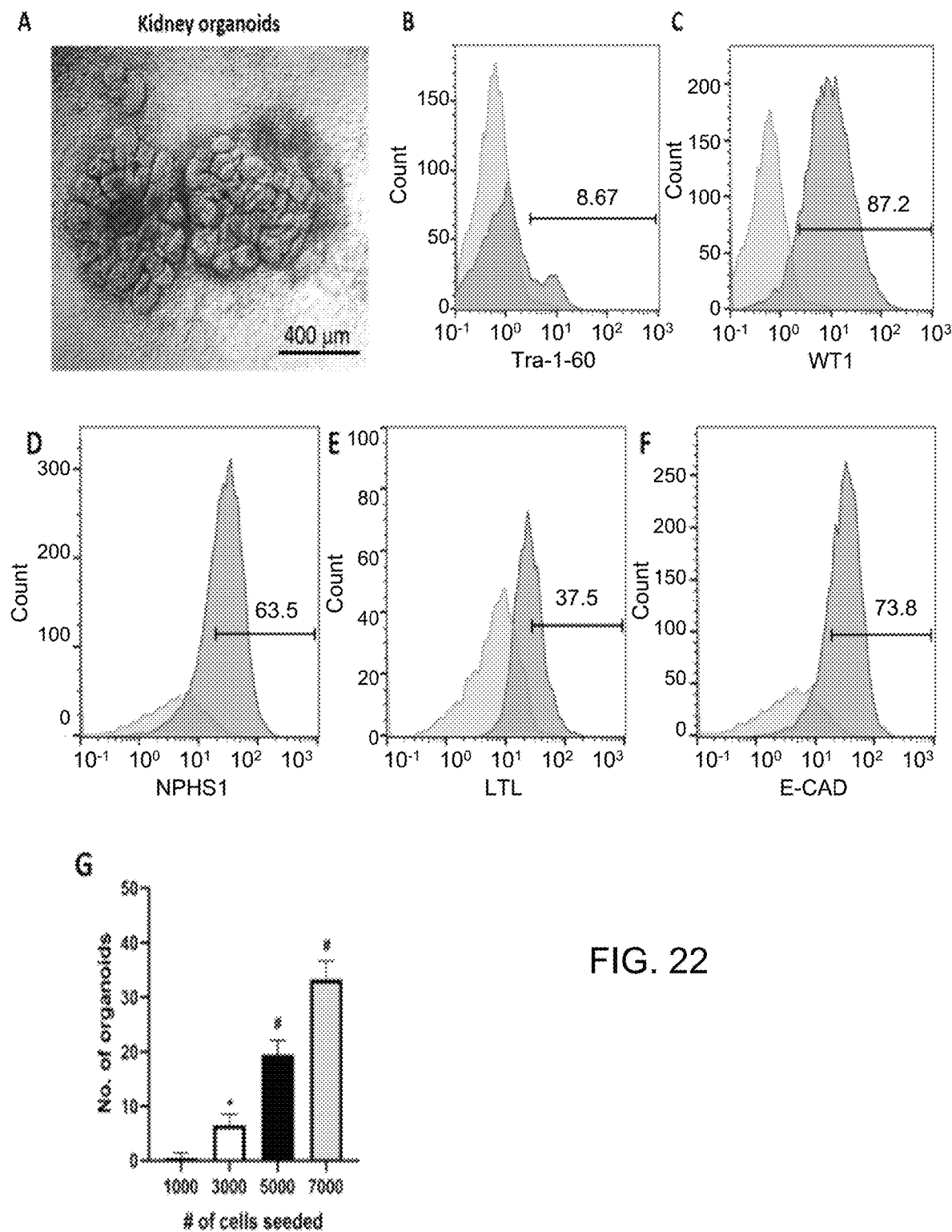
FIG. 22 shows, in Panel A, a micrograph of kidney organoids, taken at 100× magnification; Panels B-F depict representative flow cytometric plots post-renal differentiation; Panel G shows the results from optimized initial seeding cell density.

FIG. 22 shows, in Panel A, a micrograph of kidney organoids, taken at 100× magnification; Panels B-F depict representative flow cytometric plots post-renal differentiation; Panel G shows the results from optimized initial seeding cell density.

It was found that all iPS lines could generate tubular 3-D organoids composed of cells from the renal lineage using a matrix-overlay approach. Successful differentiation was first observed by the significant downregulation of TRA-1-60 expression. At the final stage of kidney development, all lines expressed <10% of the pluripotent marker. Early tubular kidney organoid patterning was observed between day 6-9 for all lines. The self-organizing structures progressively became more convoluted and densely packed within the next 7-10 days. By day 20, FC analyses confirmed induction of the posterior intermediate mesoderm through the expression of WT1 (>85±6%) and further differentiation into renal cells. Importantly, these markers suggested the presence of clusters of multipotent nephron progenitor cells (typically found during kidney organogenesis), glomerular podocytes (NPHS1: >59%±6), elongated/proximal tubule cells (LTL: >35±3%), and loop of Henle/distal tubule cells (E-cadherin: 69±7%). These segmental nephron-like structures could be found evenly distributed across the well with a variable production of approximately 25-40 kidney organoids from each iPS line (FIG. 22).

Figure 23:
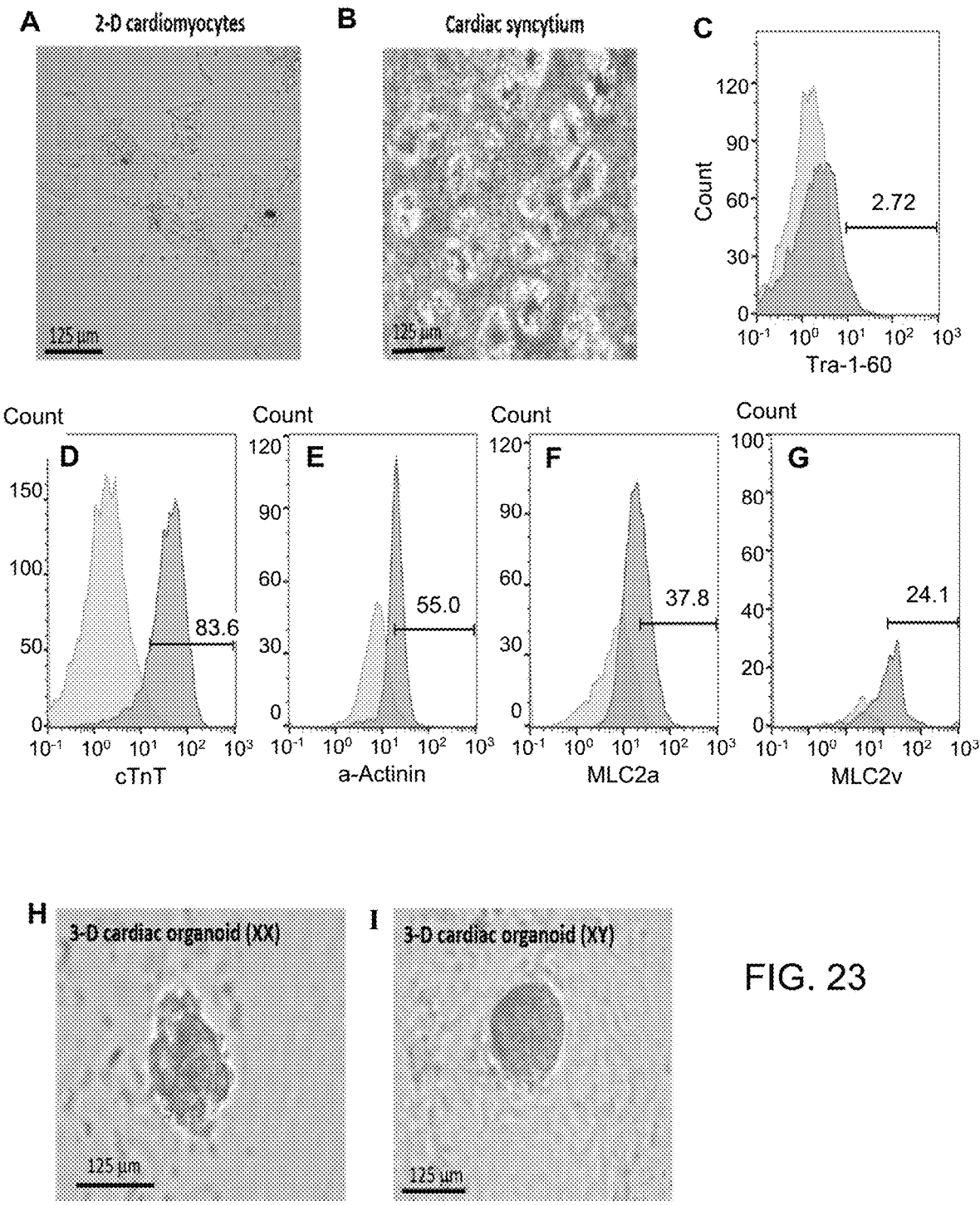
FIG. 23 shows, in Panels A & B, micrographs of a monolayer of cardiomyocytes and syncytium, taken at 100× magnification; Panels C-G depict representative flow cytometric plots post-cardiac differentiation; micrographs of representative 3-D cardiac organoids cultured from (Panel H) female and (Panel 1) male iPS lines.

FIG. 23 shows, in Panels A & B, micrographs of a monolayer of cardiomyocytes and syncytium, taken at 100× magnification; Panels C-G depict representative flow cytometric plots post-cardiac differentiation; micrographs of representative 3-D cardiac organoids cultured from (Panel H) female and (Panel I) male iPS lines.

It was found that all iPS lines demonstrated similar potential to generate cardiomyocytes in 2-D monolayer cultures in the absence of any supportive cell type. Successfully differentiation was first observed by the significant downregulation of TRA-1-60 expression. At this final stage of cardiac organogenesis, all lines expressed <5% of the pluripotent marker. The presence of spontaneously contractile cells could be observed in discrete regions as early as day 10. Eventually, the cells connected end-to-end, propagating beating "waves" when visualized. Post-lactate enrichment, FC analyses revealed that cardiac troponin T most abundantly expressed (>82±5%), followed by alpha-actinin (>55±2%). The same analyses also quantified cardiomyocyte subtype-specific markers: myosin light chain 2a (MLC2a) and 2v (MLC2v) which are hallmarks of contractile atrial and ventricular cells, respectively. The results suggested that iPS lines induced to undergo cardiogenesis possessed more atrial (>33±5%) compared to ventricular (23±2%) potential. The cardiomyocytes retained their beating capacity for >30 days in culture at the time of reporting (FIG. 23 Panels A-G).

It was found that both male and female iPS lines demonstrated similar potential to generate spontaneously contracting 3-D cardiac organoids in the absence of any supportive cell type, emerging as early as 10 days. It was observed the syncytium of cardiomyocytes aggregated to form a muscular structure reminiscent of the heart in vivo (FIG. 23, Panels H and I). The 3-D cardiac organoids in close proximity to each other were observed to undergo coordinated contraction-relaxation cycles.

Figure 24:
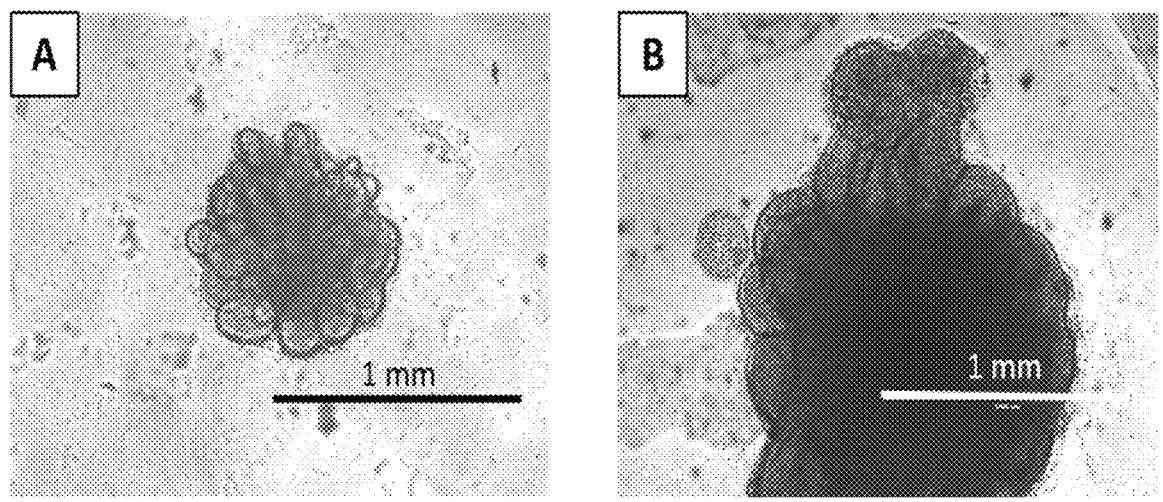
FIG. 24 shows micrographs of representative cerebral organoids at (Panel A) day 10 and (Panel B) day 20, taken at 40× magnification.

FIG. 24 shows micrographs of representative cerebral organoids at (Panel A) day 10 and (Panel B) day 20, taken at 40× magnification.

It was observed the formation of neuroepithelium structures within the developing cerebral organoid at Day 10 which continued to expand till Day 20 of differentiation (FIG. 24). Clear visualization of these structures became more challenging as the organoid grew in size and complexity to take on an opaque appearance.

Discussion

Creation of FTM-iPSCs from FTM-HUCPVCs allows the indefinite proliferation of these cells thus negating the challenge of passage-induced senescence and associated reduction in functional potency. Pluripotency of FTM-iPSCs is well-evidenced by the expression of hallmark pluripotency associated surface markers including Tra-1-60, Nanog and Oct-4. Importantly, FTM-iPSCs are able to undergo both spontaneous differentiation into embryoid body as an in vitro surrogate for teratoma formation, as well as directed differentiation into cell types representative of ectoderm, mesoderm and endoderm.

It is noteworthy that all differentiation protocols did not necessitate co-culture with animal cell types or feeder layers, which could otherwise confound interpretation of downstream results and/or restrict the clinical utility of these cells as candidates for cell therapy. Each of these differentiated cell types in isolation afford an unprecedented clinically-relevant platform for disease and development modeling, in addition to high content drug screen. While not demonstrated here, secretome of these cell types may also be employed as cell-free therapy to enhance endogenous repair and/or regeneration efforts.

Moreover, the exploitation of other technologies including 3D bioprinting and organ-on-a-chip allows individual cell types to function as "assembloids" that may be combined to better reflect complex organ systems i.e. renal-cardio axis, cardiopulmonary axis etc.

The iPS-differentiated derivatives may be used as a platform to interrogate human fetal developmental milestones in vitro. This is advantageous over the use of developmentally and physiologically distinct animal models which may not always faithfully recapitulate human disease condition.

Conclusion

The use of FTM-iPSC as a cellular tool capable of further adding to this pre-existing array of differentiated cells allows us to build a cellular armamentarium with the versatility to study a range of pathological conditions.

Example 8

Use of Vascular Derivatives from FTM-iPSCs to Enhance Angiogenesis Summary

This Example shows that vascular derivatives from FTM-iPSCs, specifically endothelial cells (i.e. iECs) and pericyte-like smooth muscle cell (i.e. iSMCs) are able to initiate and/or enhance angiogenesis. Superior angiogenesis is observed when cells are used in isolation or in combination. Organ repair and regeneration following injury shares a direct correlation with the presence of viable vasculature. Accordingly, approaches to promote growth of patent vasculature at or near the site of injury has been observed to facilitate highly efficient tissue repair. These methods typically involve the direct administration of vascular cells or the use of chemically-defined pro-angiogenic small molecules. Here, a Matrigel assay is used as an in vitro surrogate model of angiogenesis to show that conditioned media derived from iSMC monoculture or co-culture with iEC was observed to result in increased endothelial network formation. Therapeutic modalities within this complex secretome may be utilized as cell-free therapy, thus circumventing potential adverse events associated with administration of allogenic cell types.

In addition to its role in mediating repair and regeneration, patent vasculature is also critical for the continual growth and development of complex organs. 3D organoids are increasingly recognized as being superior disease-modeling and high throughput drug-screening platforms compared to 2D cell culture systems. The spontaneously formed spatio-temporal organization of organoids allows them to more precisely recapitulate in vivo organ development. This translates to higher confidence in extrapolating in vitro results in clinically-relevant human models as opposed to developmentally and physiologically distinct animal models. Progress of this promising technology is currently hampered by concerns of insufficient vasculature required to sustain organoid growth. With time, the organoid's initial dependency upon passive diffusion becomes increasingly untenable and incompatible with cell survival. The lack of patent vasculature within the organoid thus restricts their growth and maturation owing to inadequate oxygen and nutrient circulation. Formation of 3D organoids with pluripotent stem cells typically necessitates an initial embryoid body (EB) intermediary. It is during this short period of time that vasculature may be spontaneously generated de novo, albeit at extremely low frequency, thus contributing to their insufficiency. An embryoid body formation strategy was adapted to include vascular cell types prior to commencement of organ-specific differentiation. Inclusion of iSMCs within EBs was observed to more rapidly induce differentiation of endogenous endothelial cells. Incorporation of iECs led to their proliferation throughout the EB. In both instances, the presence of ready-made vascular cells alleviated at least partially, the concern of inadequate vasculature, while simultaneously promoting endogenous vascular formation.

Material and Methods iEC differentiation. FTM-iPSCs was subjected to mesoderm induction with BMP-4 and Activin A for 48 Hrs prior to differentiation into endothelial cells (ECs). Cells were differentiated following culture in DMEM/F12 supplemented with B27, N2 and BIO for a further 3 days. Media change was performed daily, ECs were then expanded in StemPro-34 supplemented with $VEGF_{165}$ for an additional 2 days prior to enrichment with CD144 microbeads. Selected $CD144^{+ve}$ cells may be cultured and passaged in StemPro-34+$VEGF_{165}$, with media change performed once every other day.

iSMC differentiation. FTM-iPSCs were passaged and cultured in ultralow attachment plates for a period of 10 days to generate EBs. Media change with E6 media supplemented with 10% FBS was performed every other day. On day 11, EBs were transferred to a gelatin-coated plates to allow for cellular outgrowths for the next 3 days. Finally, cellular outgrowths were harvested and cultured on Matrigel-coated plates with Smooth Muscle Cell Growth Media (SMGS) commercially purchased from Lonza.

Vascularized embryoid body. FTM-iPSCs were dissociated into single cell suspension prior to the addition of either iECs or iSMCs. Q-tracker 625 was used to pre-stain both vascular cell types as per manufacturer's instruction to allow for visualization of these cells, as well as their subsequent progeny. The final cell suspension was added to a microwell plate and subjected to centrifugation at 300×g for 1 min. The plate was then placed in a 5% $CO_2$, 37° C. incubator. 24 Hrs later, EBs were gently dislodge from the microwell plate using a P1000 pipette and transferred to a 6-well ultralow attachment plate for culture. Media change with E6 media supplemented with 10% FBS was performed every 2 days.

Matrigel Assay. Growth factor reduced Matrigel was thawed and 20 µl added to each well of a 96-well plate, prior to incubation in a 37° C. incubator. Upon Matrigel polymerization, single cell suspension of the desired cell type (15K cells/well) added onto the Matrigel and the plate placed in a 5% $CO_2$, 37° C. incubator until imaging is desired. Cells were resuspended in basal EBM-2 media supplemented with 5% FBS (i.e. control media), unless otherwise stated. Conditioned media was generated by culturing iSMCs monoculture or iSMC-iEC co-culture in control media for 48 Hrs prior to collection.

Results

A brief discussion of each of FIG. 25-31 is provided below, followed by additional detailed comments pertaining to the results.

Figure 25:
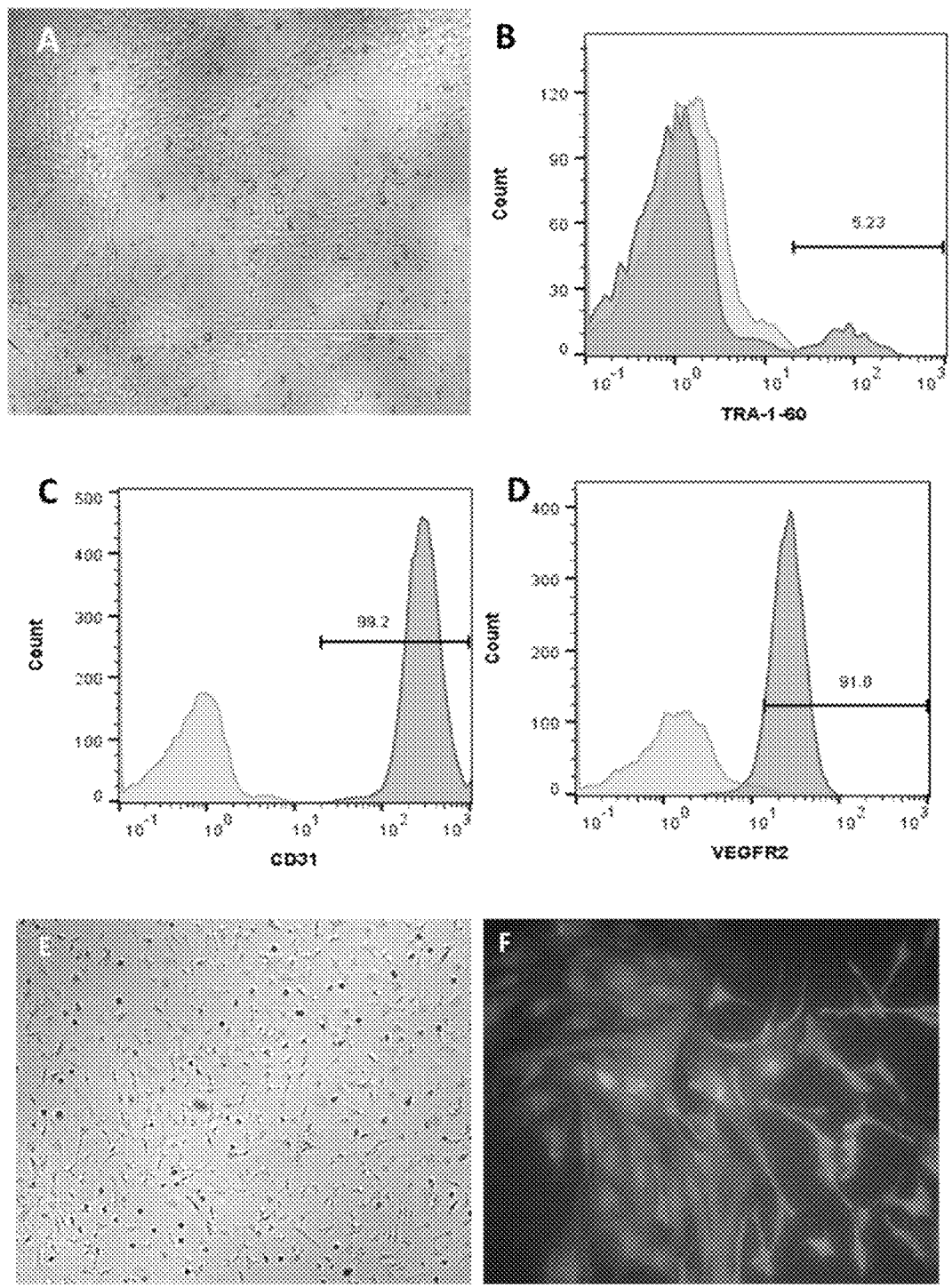
FIG. 25 shows cell morphology relevant to Example 8. Panel A shows the cobble-stone morphology of iECs. Panels B-D are representative flow cytometric plots showing expression of pluripotency marker Tra-1-60 and endothelial-associated markers CD31 and VEGFR2 following differentiation into iECs. Panel E shows the spindle-like morphology of differentiated pericyte-like iSMCs, which express Calponin as illustrated in Panel F.

FIG. 25 shows cell morphology. Panel A shows the cobble-stone morphology of iECs. Panels B-D are representative flow cytometric plots showing expression of pluripotency marker Tra-1-60 and endothelial-associated markers CD31 and VEGFR2 following differentiation into iECs. Panel E shows the spindle-like morphology of differentiated pericyte-like iSMCs, which express Calponin as illustrated in Panel F.

Figure 26:
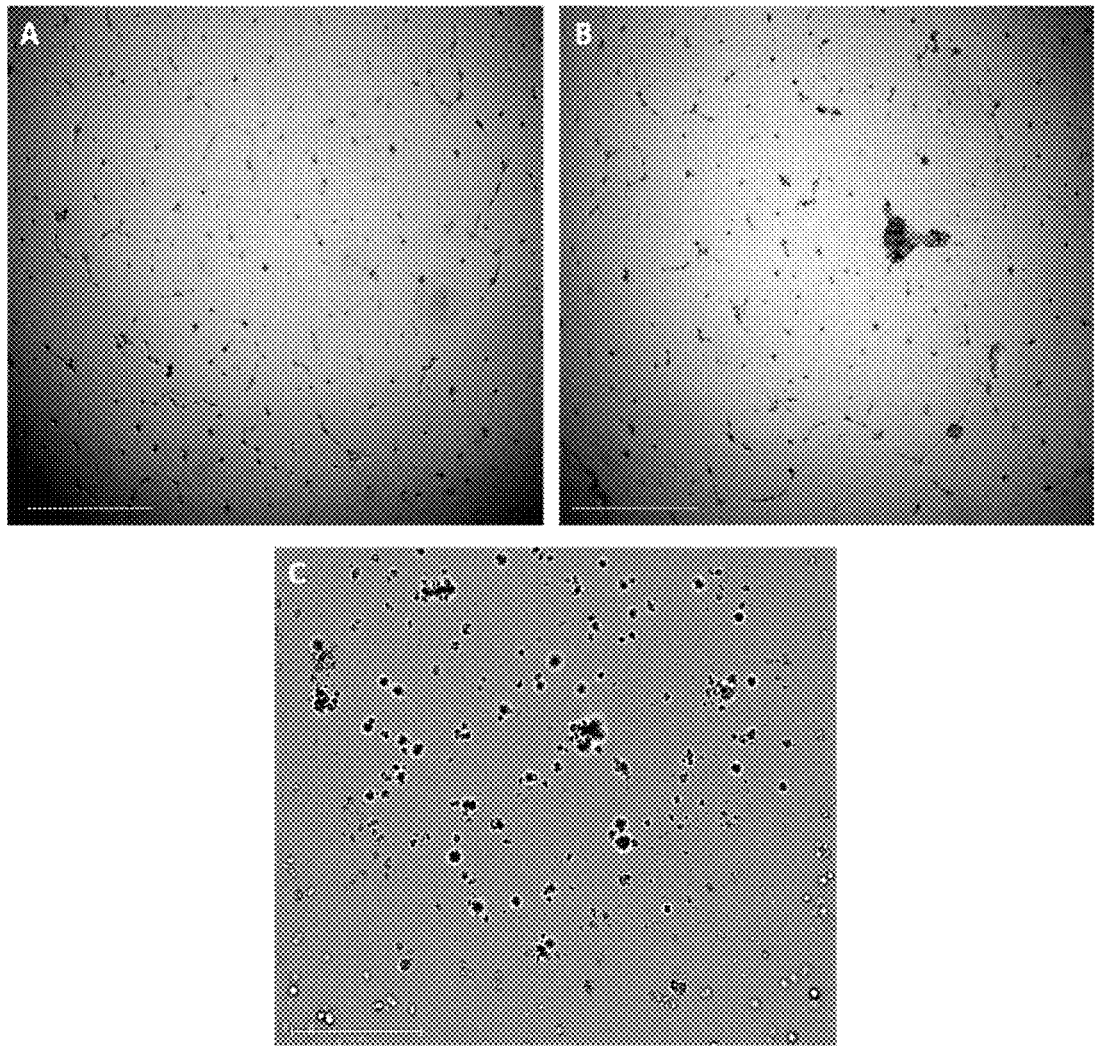
FIG. 26 shows representative micrographs taken at 40× magnification of HUVECs cultured with conditioned media derived from (Panel A) iSMC monoculture, (Panel B) iSMC-iEC co-culture and (Panel C) basal EBM-2 media.

FIG. 26 shows representative micrographs taken at 40× magnification of HUVECs cultured with conditioned media derived from (Panel A) iSMC monoculture, (Panel B) iSMC-iEC co-culture and (Panel C) basal EBM-2 media.

Figure 27:
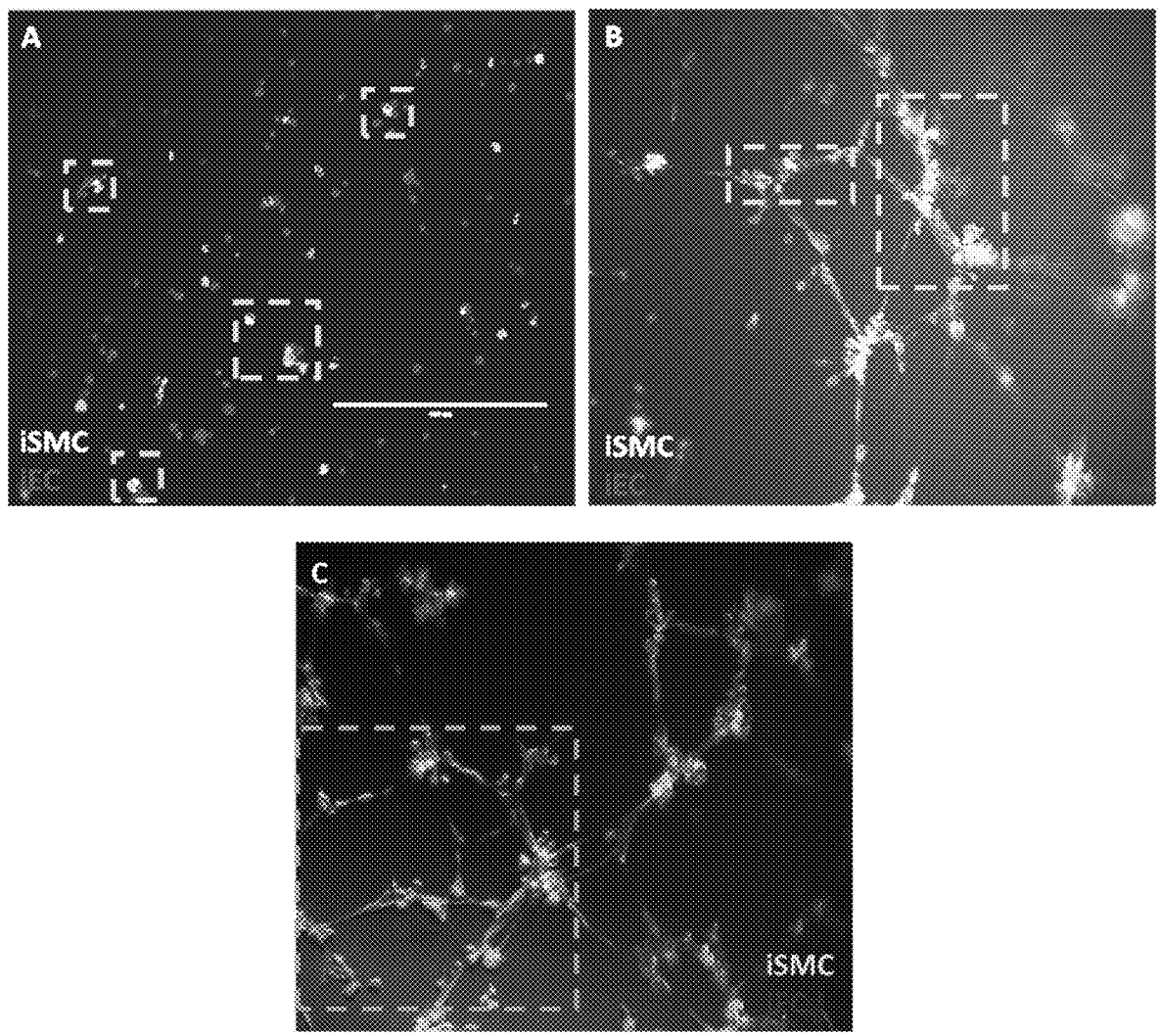
FIG. 27 shows representative micrographs of iSMC-iEC co-culture on Matrigel assay, taken at 100× magnification. Association between iSMCs and iECs was observed as early as (Panel A) 3 Hrs. This interaction persisted and continued to develop at (Panel B) 9 Hrs and (Panel C) 24 Hrs post-plating.

FIG. 27 shows representative micrographs of iSMC-iEC co-culture on Matrigel assay, taken at 100× magnification. Association between iSMCs and iECs was observed as early as (Panel A) 3 Hrs. This interaction persisted and continued to develop at (Panel B) 9 Hrs and (Panel C) 24 Hrs post-plating.

Figure 28:
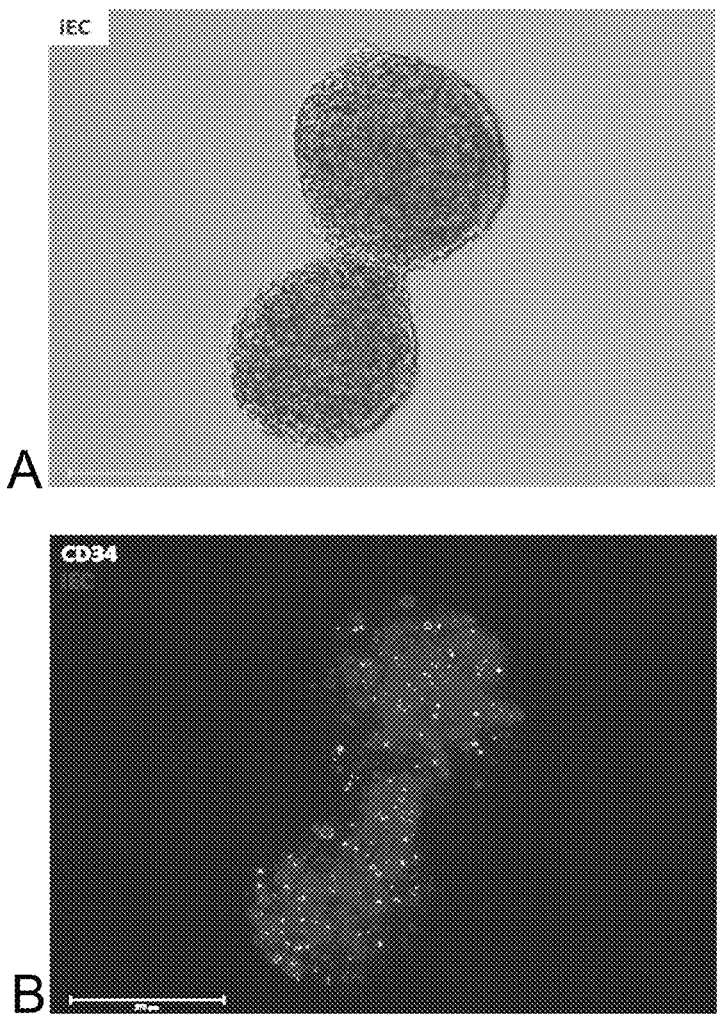
FIG. 28 shows representative micrographs of embryoid bodies prevascularized with exogenous iEC, taken at 100× magnification. iECs are well-distributed across the embryoid bodies (Panel A), albeit no absence of CD34 (Panel B) suggests absence of endogenous EC.

FIG. 28 shows representative micrographs of embryoid bodies prevascularized with exogenous iEC, taken at 100× magnification. iECs are well-distributed across the embryoid bodies (Panel A), albeit no absence of CD34 (Panel B) suggests absence of endogenous EC.

Figure 29:
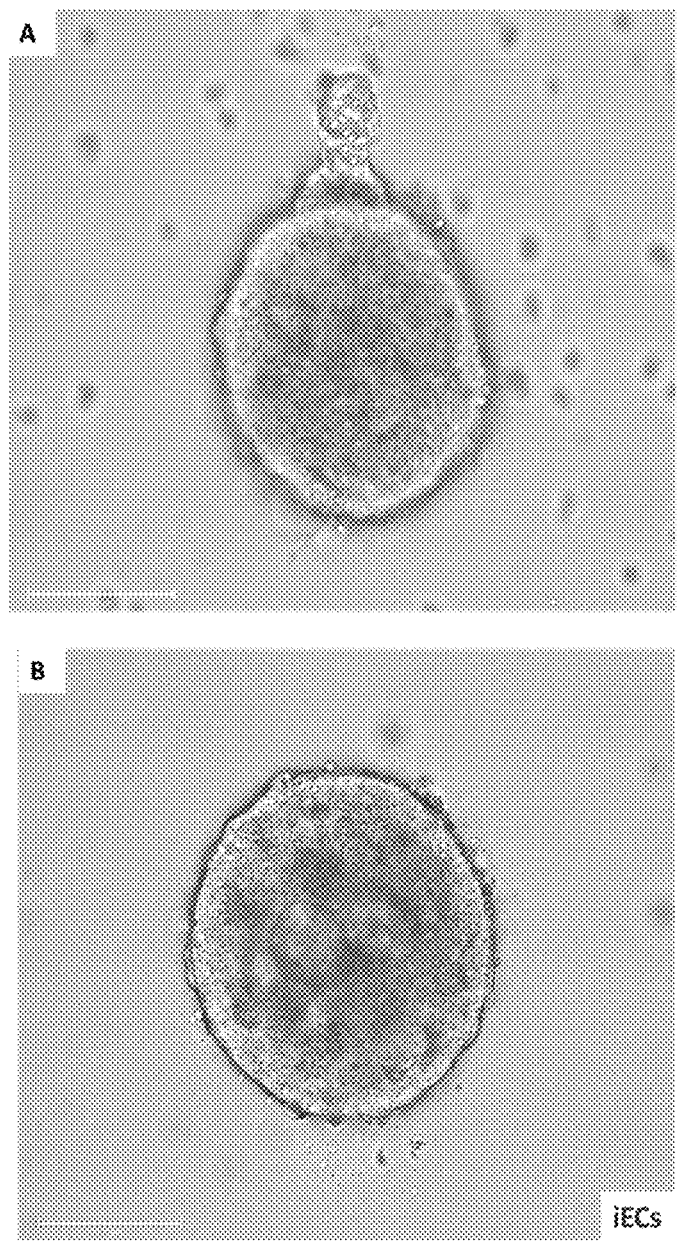
FIG. 29 shows representative micrographs of embryoid bodies, taken at 100× magnification which do not incorporate iECs (Panel A) and which do incorporate iECs (Panel B).

FIG. 29 shows representative micrographs of embryoid bodies, taken at 100× magnification which do not incorporate iECs (Panel A) and which do incorporate iECs (Panel B).

Figure 30:
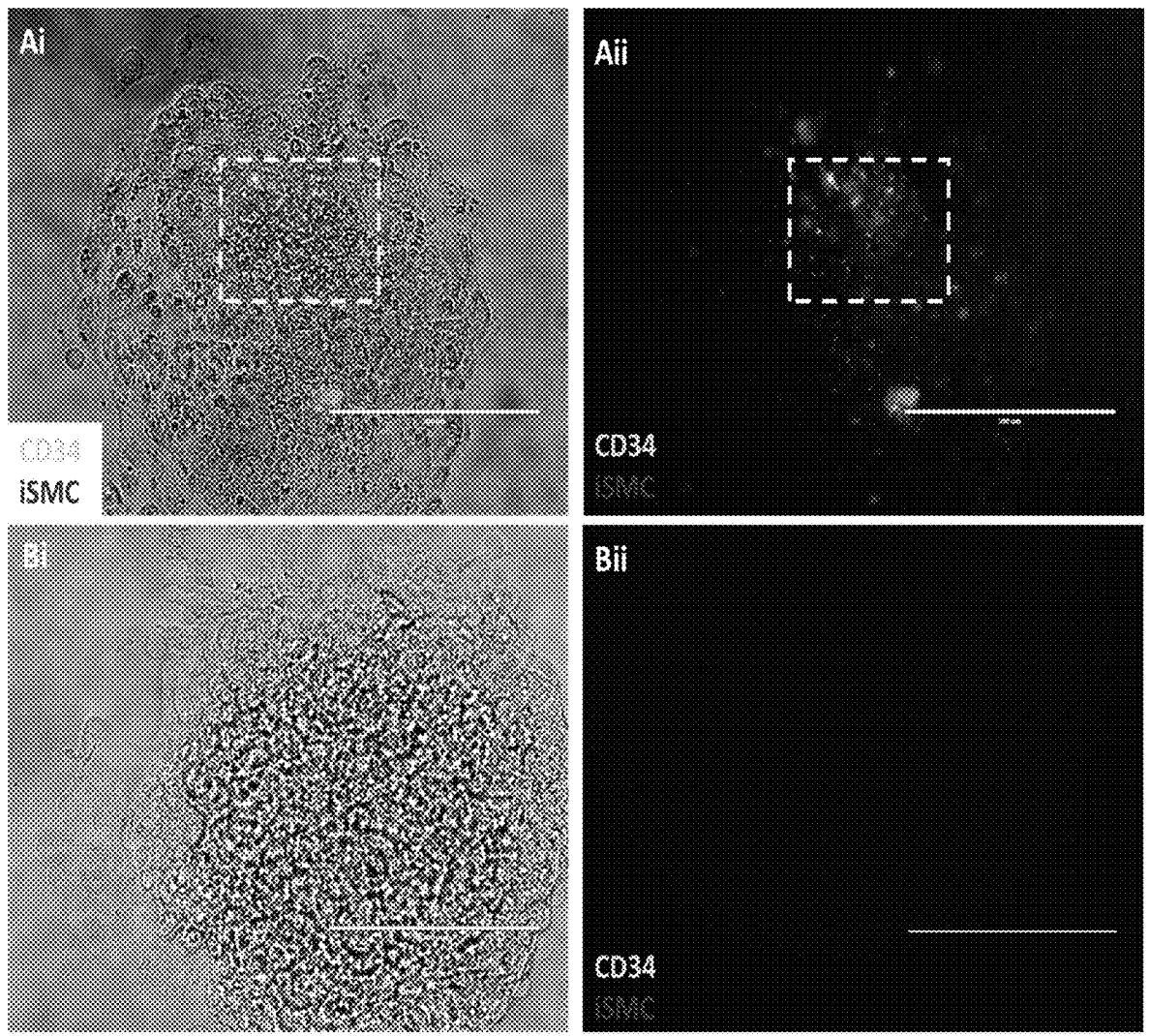
FIG. 30 shows representative micrographs of embryoid bodies, taken at 100× magnification. The presence of endogenous endothelial cells (CD34) was only noted in embryoid bodies which have incorporated iSMCs (Panels Ai and Aii) but not in embryoid bodies formed from FTM-iPSC alone (Panels Bi and Bii).

FIG. 30 shows representative micrographs of embryoid bodies, taken at 100× magnification. The presence of endogenous endothelial cells (CD34) was only noted in embryoid bodies which have incorporated iSMCs (Panels Ai and Aii) but not in embryoid bodies formed from FTM-iPSC alone (Panels Bi and Bii).

Successful differentiation of FTM-iPSCs into iECs was evidenced by their characteristic cobblestone morphology and ability to form network-like structures in in vitro cultures (see FIG. 25, Panel A). Flow cytometric analysis also noted downregulation of pluripotency-associated protein Tra-1-60 but high expression of endothelial-associated proteins CD31 and VEGFR2 (see FIG. 25, Panels B-D). Differentiated iSMCs also showed characteristic spindle-like morphology and expression of the smooth muscle associated protein, Calponin (see FIG. 25, Panels E-F).

It was observed that culture of HUVECs with conditioned media derived from iSMC alone or iSMC-iEC co-culture over a 48 Hr period led to more rapid formation of neovessels within a 5 Hr timeframe (see FIG. 26, Panels A and B, respectively). Comparatively, HUVECs cultured in control media demonstrated far inferior capacity for sprouting angiogenesis at this early time-point (see FIG. 26, Panel C).

It was found that even at a very early time-point (3 Hr post-plating), iSMCs which were pre-stained with CellBrite Green Cytoplasmic Membrane dye demonstrated a high propensity to co-localize with iECs (stained red with Q-tracker 625). This cellular association remains as networks emerged at later time-points of 9 Hrs and 24 Hrs (see FIG. 27, Panels A to C, respectively).

As illustrated in FIG. 28, Q-tracker labelled iECs were able to be evenly dispersed and proliferate throughout the 3D embryoid body. Unlike addition of iSMCs, it is not immediately obvious that presence of exogenous iECs promote spontaneous differentiation of endogenous CD34+ve cells.

As illustrated in FIG. 29, the mixture of pre-stained iPS-derived endothelial cells (iECs) with undifferentiated iPSCs prior to induction of 3-D cardiomyocyte differentiation yielded slightly larger but not necessarily a greater number of cardiac organoids in a given time period. The vasculature was observed to line the surface of the organoid as well as found to be incorporated within its body for at least 10 days.

Similar to results from Matrigel assay, successful incorporation of iSMCs into 3D embryoid body formation was also observed to promote the spontaneous differentiation of endogenous endothelial progenitor cells. This was evidenced by green fluorescence emitted by CD34+ve cells which cluster with Q-tracker labelled iSMCs which fluoresce red (see FIG. 30, Panels Ai and Aii). In contrast, green CD34+ve cells were completely undetected in control EBs comprised solely of pluripotent FTM-iPSCs (see FIG. 30, Panels Bi and Bii).

Discussion

This Example found that iECs and iSMCs differentiated from FTM-iPSCs are able to leverage upon the epigenetic memory of the parental FTM-HUCPVCs and exert proangiogenic effects in both 2D and 3D culture systems. Proangiogenic cues may be mediated directly by the presence of these vascular cell types or indirectly, through their secreted paracrine factors. The intricacies of varied cellular mechanisms orchestrated to work in concert to ensure maintenance of homeostatic angiogenesis underscores the synergistic interaction amongst multiple cell types. The multifaceted nature of these interactions provides compelling reasons for regenerative efforts to target support cells in addition to just ECs. For example, the stabilization and functional maturation of patent vasculature hinges upon bilateral crosstalk between ECs and mural cell types including pericytes in microvessels and SMCs in larger vessels. As with most pluripotent stem cell derivative, the immaturity of iSMCs is likely to confer upon them a progenitor function which allows it to function in a manner akin to pericytes. As seen from the Matrigel assay, these pericyte-like iSMCs preferentially home towards iECs at the earliest opportunity and remain closely associated as network formation progresses. It is likely that the physical presence of iSMCs strengthens the otherwise fragile capillary-like EC networks.

Subsequent maturation of EC networks may also be a function of paracrine factors secreted by iSMCs. Compared to control media, conditioned medium derived from iSMC monoculture was able to aid neoangiogenesis processes, albeit this remains inferior to conditioned medium derived from iSMC-iEC co-culture. This observation strongly suggests that while the secretome of iSMCs at basal state is beneficial for neoangiogenesis, the physical proximity of the two cell types likely results in differences in their activation status. Consequently, alterations in both iSMC's and iEC's secretome profile, to one that possess superior pro-angiogenic properties occurs.

Similarly, presence of iSMCs in 3D EB models was also able to induce rapid de novo generation of endogenous ECs. While iSMCs were observed to be distributed across the EBs in a manner similar to incorporated iECs, there was noticeably more Q-tracker labelled iECs detected. This suggests that incorporated iECs underwent rapid proliferation, possibly as part of their network formation efforts. Absence of CD34+ve cells may be attributed to two reasons. In the first instance, the dense clustering of cells in a 3D embryoid body creates multiple planes of focus, thus clear visualization of these cells may be beyond the resolution limits of the microscope used. Secondly, the rapid assembly of rudimentary vasculature within the EB by exogenously incorporated iECs, negates the urgency to establish endogenous vasculature.

Conclusion

Collectively, these observations have several implications: (1) iSMC and/or their secretome is more pertinent if the purpose is to trigger endogenous neoangiogenesis. Hence, while iSMCs alone do not form networks as readily as ECs, targeted enhancement of their supportive role in angiogenesis is likely to translate to increase vascular density. (2) The use of iSMC-iEC secretome in its entirety or selected secretome components (i.e. exosomes) as modalities for cell-free therapy. Optimization of culture conditions (i.e. oxygen concentration, application of sheer stress etc.) may yet increase the potency of iSMC's secretome. (3) The relative immaturity of iECs suggests that they have yet to assume specific arterial or venous identities. Incorporation of these primordial iECs into EBs facilitates their adoption of organ-specific identity and function as differentiation proceeds. In turn, this increases organoid complexity and functional maturation while reducing the reliance on the paucity of spontaneously formed endogenous EC network.

Current approaches to increasing organoid vasculature involve implantation into animals, seeding ECs on the surface of organoids or the use of pro-angiogenic factors. The first approach which results in explanted organoid containing a mixture of human and animal cell types renders it challenging to accurately extrapolate results from disease-modeling and drug-screening studies. While the second approach avoids the confounding factor of animal cells, reliance on EC ingression and subsequent even distribution throughout the organoid is challenging since seeding of ECs may only be performed on localized surface of the organoid. Finally, the use of proangiogenic factors assumes that these do not exert any "off-target" effects on the differentiation cocktail used to generate organ-specific identity. The use of pre-vascularized EBs which circumvents all these challenges could be employed as a starting point for the generation of a range of organ-specific organoids, including cardiac organoids. These pre-vascularized organoids, which likely possess greater maturation and complexity, afford an excellent platform for high-throughput drug screening and disease-modelling efforts.

Example 9

FTM HUCPVC Extracellular Vesicles (EV): Isolation/Characterization, And Functional Data It has been found that extracellular vesicles (EV) can be enriched from media conditioned by HUCPVC using multiple methods. A Qiagen Kit may be employed for specific isolation of EV, and other proteins secreted in media can also accomplish an enriching effect. Certain angiogenic factors are enriched in EV when compared to conditioned media (CM).

Extracellular vesicles (EV) derived from first trimester versus full term umbilical cord perivascular cells were compared to consider and compare isolation methods and culture conditions. EVs derived from mesenchymal stem cells (MSCs) have been widely studied in pre-clinical and clinical trials. Potential influences on EV diversity include cell type, cell line, culture conditions, and the method of EV isolation. Using first trimester human umbilical cord perivascular cells (FTM HUCPVCs), a superior capacity for regeneration has been found when compared to bone marrow MSCs or term HUCPVCs. Variations in EV marker protein expression between different isolation methods is also found. Optimized methods for efficient production and purification of HUCPVC-EVs are described, and the effects of culture conditions on HUCPVC-EV yield, morphology, contents and biological effects are described, in terms of the culture system and glucose concentration.

Conditioned media (CM) is prepared from FTM/Term HUCPVCs expanded to 70-80% confluence in regular growth media (aMEM+5% HPL/10% FBS) in a multilayer flask or 10 cm Petri dish. Media was replaced with serum-free media containing either normal glucose (NG, 5.56 mM) or low glucose concentration (LG, 2.78 mM) for 48 hrs. EV isolation was conducted using ultracentrifugation (UC), Qiagen™ ExoEasy Maxi kits, and Qiagen™ qEV column. Visualization and characterization of EVs was done by transmission electron microscopy (TEM) and nanoparticle tracking analysis (NTA). Analyzing EV contents was done by Qubit RNA/protein assays, SBI Exo-Check Exosome Antibody Arrays, and mass spectrometry (MS). Assessing cell viability was done by lactate dehydrogenase (LDH) cytotoxicity assays on CM. Buffer exchange was done with VivaSpin-500™ with 100 kDa cutoff; PBS (protein array, cancer cell growth assay); and ammonium bicarbonate (MS). Impact of EVs on cancer cell count: was evaluated with Melanoma cells (A375) and a CKK-8 assay to measure viable cell number.

Figure 31:
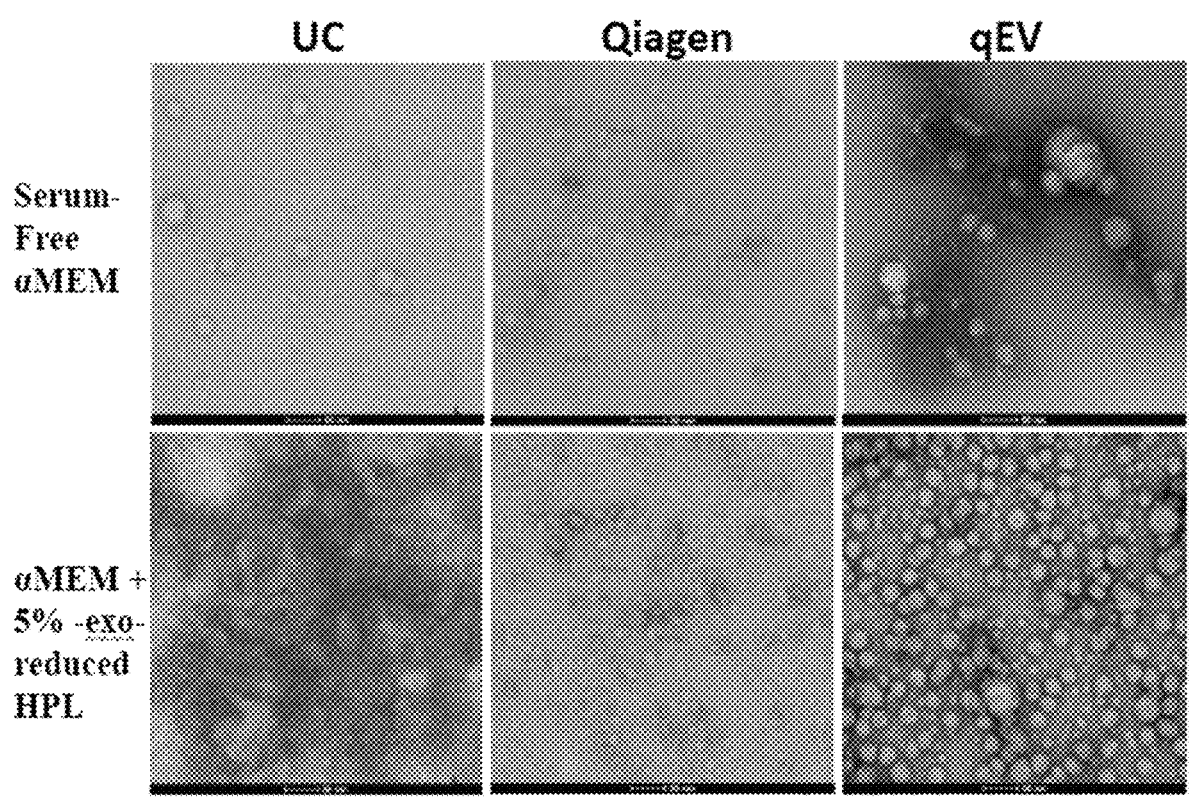
FIG. 31 shows TEM images confirming the presence and morphology of FTM EVs according to Example 9.

FIG. 31 shows confirmation of the presence and morphology of FTM EVs from the described methods. A TEM of FTM HUCPVC-derived EVs post qEV, UC, Qiagen ExoEasy, and qEV isolation is depicted for serum-free α-MEM and for α-MEM+5% exo-reduced HPL. Pictures are at 73,000× magnification from a Thermo Fisher Scientific Talos L120C.

Figure 32:
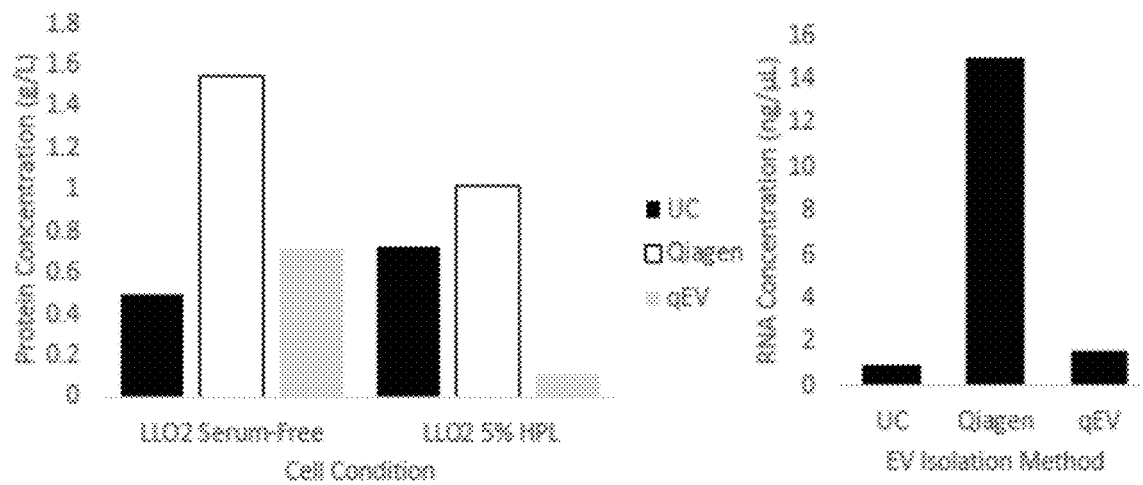
FIG. 32 shows protein and RNA quantities for Qiagen-isolated FTM EVs as compared with EVs isolated by centrifugation.

FIG. 32 shows that Qiagen-isolated FTM EVs have greater protein and RNA quantities than EVs isolated by centrifugation. Protein and RNA quantification of FTM HUCPVC-derived EVs or αMEM after qEV, UC, or Qiagen ExoEasy isolation was conducted and quantification was performed using Qubit arrays. RNA quantification was performed on LLO2 αMEM 5% exo-reduced HPL.

Further, the Qiagen isolation method generates relatively uncontaminated EV isolates compared to ultracentrifugation (serum-free CM). Exosome antibody arrays of FTM HUCPVC-derived EVs (LLO2 αMEM, serum-free) from UC or Qiagen ExoEasy isolation were evaluated. SBI Exo- Check Exosome Antibody Arrays were used, and cis-Golgi matrix protein (GM130) was used as a negative control for cellular contaminants, to arrive at these findings.

VivaSpin buffer exchange resulted in loss of EV yield post-exoEasy Kit isolation, but did not alter mean particle size. This was confirmed by NTA particle quantification and mean particle size of Qiagen-isolated HUCPVC-derived EVs before and after VivaSpin 100 kDa.

Regarding morphology and yield, FTM HUCPVCs cultured in 10 cm Petri dishes produce smaller EVs and a greater quantity compared to those cultured in multilayer flasks. Mean Particle Size (nm) of 149±2 and 248.8±10.5 were observed for the Petri dish versus the flask, and normalized Particle Concentration (#/mL)/cell was: $4.88 \times 10^5$ versus $3.62 \times 10^4$, respectively.

Regarding protein/RNA content, FTM HUCPVCs cultured in 10 cm Petri dishes produce EVs with comparable protein and RNA concentrations when compared to those cultured in multilayer flasks. Protein concentrations (pg/μL) of 0.295 and 0.333; and RNA concentrations (ng/μL) of 18.6 and 20.9 were observed for the Petri dish and the multilayer flask, respectively.

Figure 33:
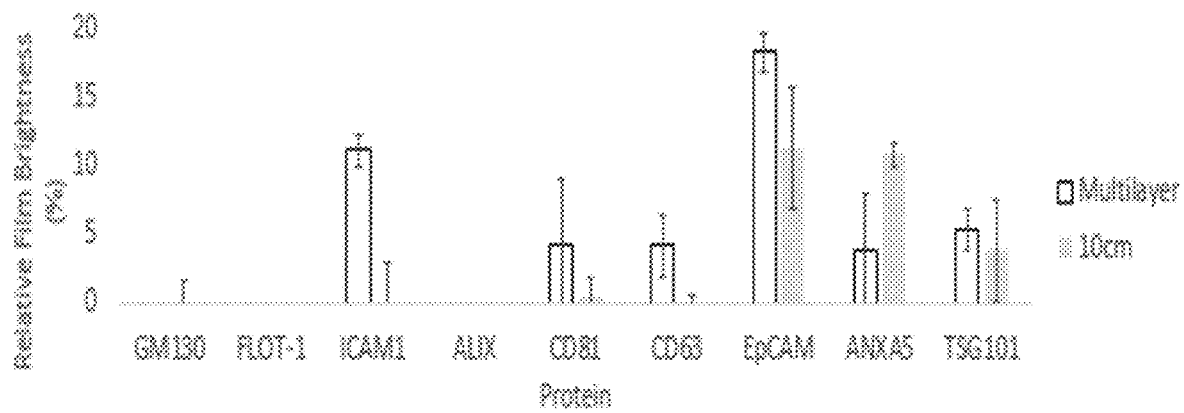
FIG. 33 shows relative film brightness for FTM HUCPVC-EVs isolated from multilayer flasks and 10 cm Petri dishes, exhibiting differences in EV markers in Example 9.

FIG. 33 shows that FTM HUCPVC-EVs isolated from multilayer flasks and 10 cm Petri dishes exhibited differences in EV markers. Exosome antibody arrays of FTM HUCPVC-derived EVs (Qiagen-isolated) cultured in a multilayer flask or 10 cm Petri dish are shown, based on SBI Exo-Check Exosome Antibody Arrays. Error bars show standard deviation. P=0.0442 for ICAM1.

It was found that glucose concentration during cell culturing has a relatively small impact on protein expression. Further, the glucose concentration during cell culturing did not impact the effect of HUCPVCs on melanoma cell growth in melanoma cells (A375) incubated with the Qiagen-isolated EVs from either FTM or term HUCPVCs.

Figure 34:
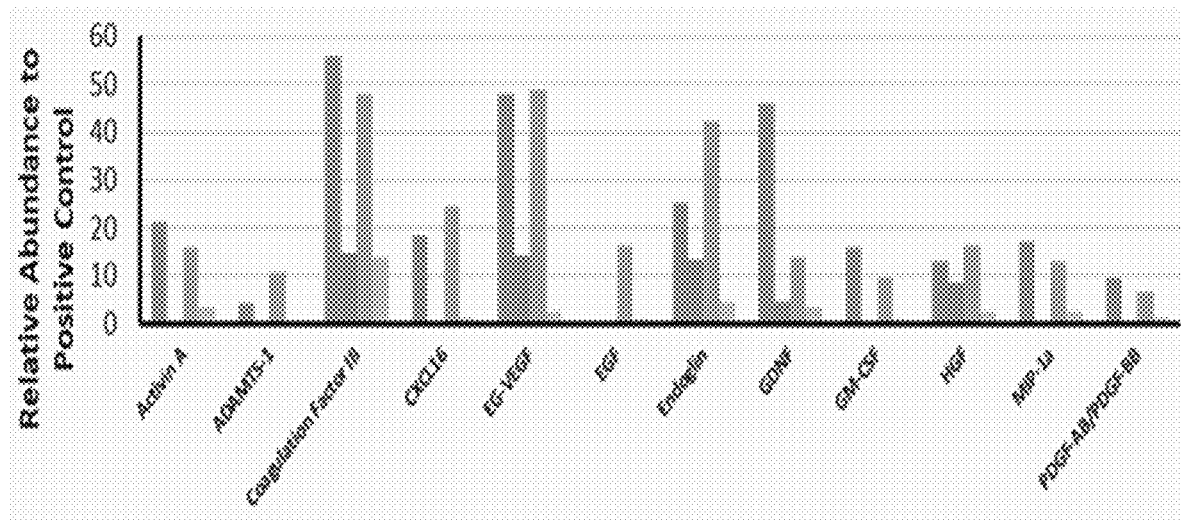
FIG. 34 shows angiogenic factors enriched in extracellular vesicle (EV) preparation when compared to conditioned media (CM).

FIG. 34 shows angiogenic factors that were enriched in extracellular vesicle (EV) preparation when compared to conditioned media (CM). The order of the 4 grey treatment bars shown) from left to right for each protein is: CM+Lysis; CM−Lysis; EV+Lysis; and EV−Lysis. Angiogenic proteins in EV and CM preparations derived from FTM HUCPVC via protein array are shown. Proteins that are at least 2-fold greater in EV preparations with lysis buffer, and present in no less than 50% of the CM fraction with lysis buffer are depicted. Values are normalized to volume (n=1). The methods involved in identification of angiogenic proteins involved identification in FTM HUCPVC-derived EV preparations and CM, detected using Angiogenesis Proteome Array, and samples were treated with Nonidet P-40 (Sigma) to disrupt EV.

Example 10

FTM HUCPVC Extracellular Vesicles (EV): Immunomodulatory Effects on T Lymphocyte Differentiation Summary It has been found that extracellular vesicles (EV) can be enriched from media conditioned by HUCPVC using multiple methods. FTM HUCPVC-EV show immunomodulatory effects on T cells and monocytes. Data is included herein regarding immunomodulatory properties of MSCs. HUCPVC elicited an immunomodulatory effect by increasing the T regulatory cells/T effector cell (Treg/Teff) ratio in a paracrine manner, which can be partially impaired by the endosomal pathway inhibitor, GW4869. Within CD4+ T cells, HUCPVC-EV promoted both the proliferation of Treg and Teff. Notably, the ratio of proliferating Treg/proliferating Teff was increased by HUCPVC-EV treatment when compared to no cell EV-depleted CM control isolations, which eventually resulted in an increased Treg/Teff ratio. FTM HUC-PVC-EV showed increased effects on proliferating Treg/proliferating Teff ratio when compared to term HUCPVC-EV. In the CD8+ population, administration of HUCPVC-EV significantly shifted the CD8+ population toward a $CD8^{low}$ population. No significant difference was found in the effect of EV derived from inflammatory primed and unprimed HUCPVCs.

Background Human umbilical cord perivascular cells (HUCPVC) are a promising source of mesenchymal stromal cells for regenerative therapy applications. Here, is investigated the paracrine immunomodulatory properties of HUCPVC and HUCPVC-derived extracellular vesicles (EV) by studying their effects on T lymphocyte differentiation in vitro.

Methods: Conditioned medium (CM) was obtained from sub-confluent FTM and term HUCPVC cultured for 48 hrs in serum-free RPMI medium with or without pro-inflammatory cytokines (10 ng/mL of IFN-γ and 15 ng/mL of TNF-α). HUCPVC-derived EV were enriched from CM using the Qiagen exoEasy Maxi kit, followed by a Vivaspin 100 k MWCO buffer exchange. Human unfractionated peripheral blood mononuclear cells (PBMC) were isolated by Ficoll gradient from healthy donors. PBMC stimulated with anti-CD3/CD28 beads were co-cultured with HUCPVC or EV for five days. T lymphocyte subpopulations were analyzed by flow cytometry.

Results: HUCPVC elicited an immunomodulatory effect by increasing the T regulatory cells/T effector cell (Treg/Teff) ratio in a paracrine manner, which could be partially impaired by the endosomal pathway inhibitor, GW4869. Within CD4+ T cells, HUCPVC-EV promoted both the proliferation of Treg and Teff. Notably, the ratio of proliferating Treg/proliferating Teff was increased by HUCPVC-EV treatment when compared to no cell EV-depleted CM control isolations, which eventually resulted in an increased Treg/Teff ratio. FTM HUCPVC-EV showed increased effects on proliferating Treg/proliferating Teff ratio when compared to term HUCPVC-EV. In the CD8+ population, administration of HUCPVC-EV significantly shifted the CD8+ population toward a $CD8^{low}$ population. No significant difference was observed in the effect of EV derived from inflammatory primed and unprimed HUCPVCs.

Figure 35:
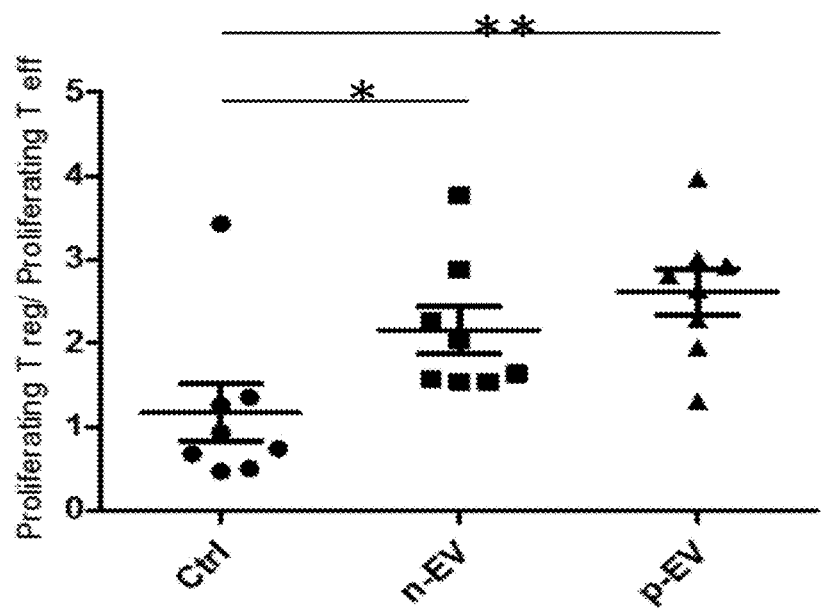
FIG. 35 shows the effect of FTM HUCPV-EVs on proliferation of T cell subtypes in Example 10.

FIG. 35 shows the effect of FTM HUCPV-EVs on proliferation of T cell subtypes. The ratio of proliferating $T_{reg}/T_{eff}$ cells is shown for unprimed (n-EV) and primed (p-EV) extracellular vesicles. Bars represent the mean±SD, *p<0.05 and **p<0.01 by one-way ANOVA with Bonferroni's multiple comparison test.

Figure 36:
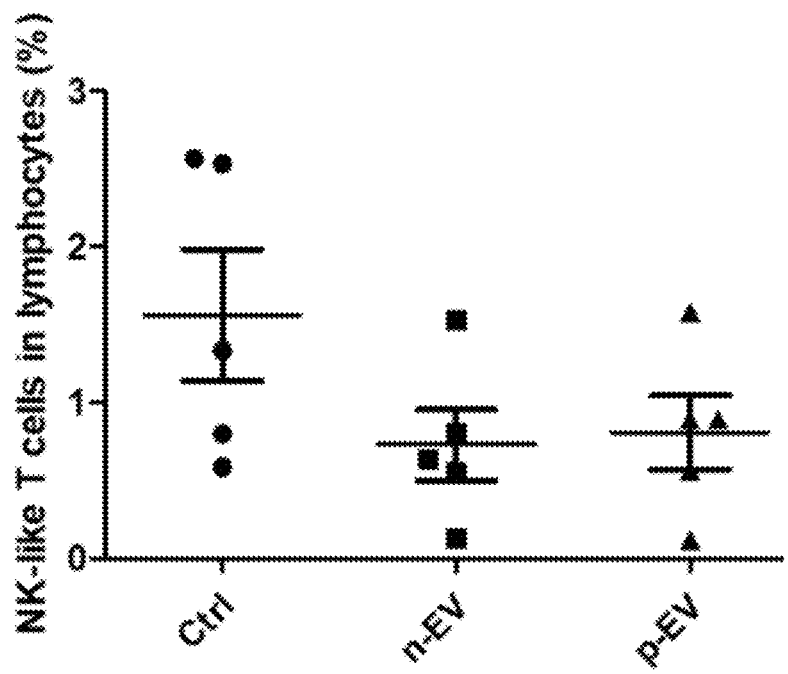
FIG. 36 shows the effect of HUCPVC-EVs on proportion of NK-like T cells in total lymphocyte population.

FIG. 36 shows the effect of HUCPVC-EVs on proportion of NK-like T cells in total lymphocyte population, for unprimed (n-EV) and primed (p-EV) extracellular vesicles. Bars represent the mean±SD.

Conclusion: FTM HUCPVC-EV demonstrated immunomodulatory effects by increasing the Treg/Teff ratio in CD4 T helper cells and shifting the cytotoxic T cell phenotype toward CD8low. HUCPVC-EV represent a promising cell-free immunomodulatory therapy for regenerative applications.

Example 11

Non-Reprogrammed HUCPVC Clearance in the Lung (Immune-Mediated) is Associated with Improved Resolution of Lung Injury in a Model of ICI-Induced Myocarditis and Lung Injury.

Methods. A mouse model was established to look at the immune related adverse events associated with cancer immunotherapy. The animals receiving immunotherapy received a combination of anti-PD-1 and anti-CTLA-4. Four groups were established, a control group with media injections, a group receiving only FTM HUCPVC, a group receiving only immunotherapy, and a group receiving a combination of both treatments. FTM HUCPVC were injected with 1 million cells in 25 µL. For Ashcroft scoring, three doses of immunotherapy and two doses of cell therapy were given. For the 24 hour animals, only one does of each was given. The lung tissue was stained with Masson's trichrome and 4 independent observers scored the tissue using the Ashcroft scoring system. Each tissue was assessed at 6 different locations, and the overall section was given a score based on the average of all sections.

Figure 37:
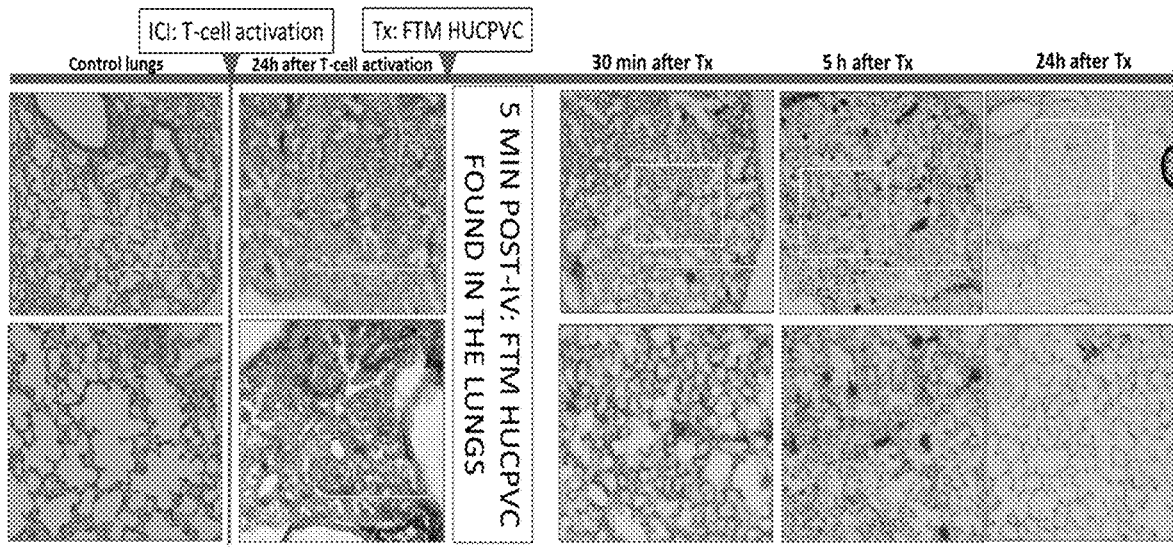
FIG. 37 shows lung resolution through 24 hr time points, with ICI: T=cell activation and Tx: FTM HUCPVC time points.

FIG. 37 shows lung resolution through 24 hr time points, with ICI: T=cell activation and Tx: FTM HUCPVC time points. Notably, 5 min post-IV: FTM HUCPVC found in the lungs. Lung tissue at 30 min, 5 hours and 24 hours post Tx are shown.

Figure 38:
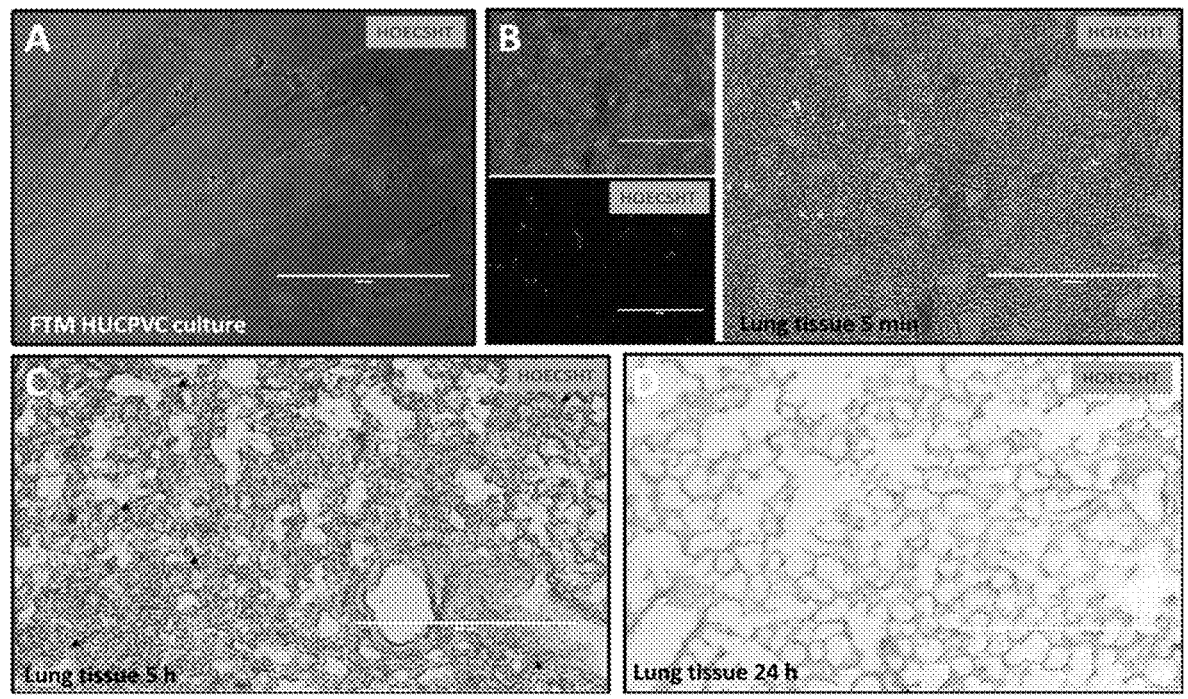
FIG. 38 shows an apparent resolution of the lung tissue through 24 hours in Example 11.

FIG. 38 shows an apparent resolution of the lung tissue through 24 hours. Panel A shows FTM HUCPVC culture (Hoecsht-labeled) at Tx; Panel B shows lung tissue at 5 minutes post-IV; Panel C shows lung tissue at 5 hours post Tx; and Panel D shows lung tissue at 24 hours post Tx.

Figure 39:
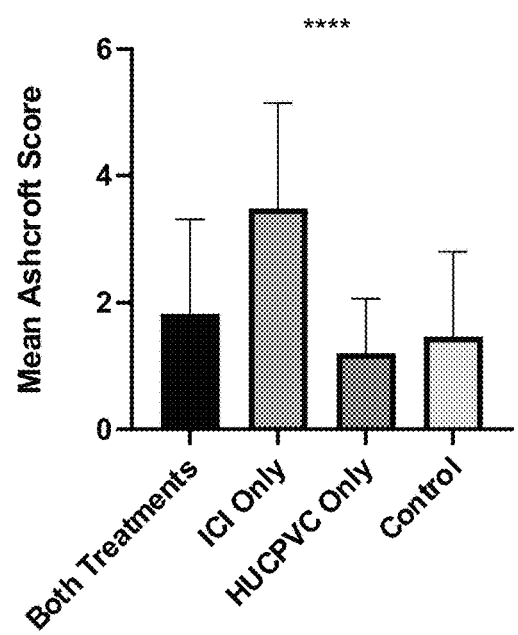
FIG. 39 shows mean Ashcroft scoring for lung tissue evaluated in Example 11.

FIG. 39 shows mean Ashcroft scoring for lung tissue (a) for "both Treatments" (ICI & HUCPVC); (b) ICI only; (c) HUCPVC only, and (d) control. The mean Ashcroft score was based on scores from 4 independent observers. Each observer achieved significance in their own scoring showing a reduction in fibrotic tissue in the groups receiving FTM HUCPVC along with ICI injections when compared to ICI group (P<0.0001), with statistics performed as a one-way ANOVA test.

In the preceding description, for purposes of explanation, numerous details are set forth in order to provide a thorough understanding of the embodiments. However, it will be apparent to one skilled in the art that these specific details are not required in order to practice the technology.

The above-described embodiments are intended to be examples only. Alterations, modifications and variations can be effected to the particular embodiments by those of skill in the art without departing from the scope, which is defined solely by the claims appended hereto. All documents referred to herein are incorporated by reference.

The invention claimed is:

1. A method of isolating pluripotent human umbilical cord perivascular cells for treating cardiovascular injury or heart disease, wherein the isolated perivascular cells are reprogrammed as pluripotent cells for differentiation into cardiomyocytes expressing cTnl,
   wherein the pluripotent human umbilical cord perivascular cells are obtained by:
   collecting an umbilical cord from fetal tissue obtained at less than 13 weeks of gestation, by collecting fetal placenta tissue by surgical aspiration; and separating the umbilical cord from the fetal placenta tissue;
   treating the umbilical cord to obtain isolated perivascular cells, by:
   washing the umbilical cord with PBS,
   cutting the umbilical cord, comprising an artery and two vessels, into smaller cut pieces,
   treating the cut pieces with collagenase to obtain isolated perivascular cells, and
   washing the isolated perivascular cells with PBS; and
   incubating the isolated perivascular cells, by suspending the isolated perivascular cells in a maintenance medium comprising α-MEM, penicillin-streptomycin, and amphotericin; and
   maintaining the isolated perivascular cells by:
   washing the isolated perivascular cells with PBS;
   adding trypsin-EDTA;
   harvesting the isolated perivascular cells into a tube containing maintenance medium;
   separating the isolated perivascular cells from the maintenance medium;
   mixing the isolated perivascular cells with new maintenance medium;
   diluting the new maintenance medium containing the isolated perivascular cells with additional maintenance medium to obtain a diluted maintenance medium containing the isolated perivascular cells;
   maintaining the diluted maintenance medium containing the isolated perivascular cells under appropriate growth conditions of 37° C., 5% $CO_2$ in a maintenance medium, and changing the maintenance medium every 3-7 days;
   suspending the maintained cells; and
   reprogramming the isolated perivascular cells by adding thereto at least one gene reprogramming factor selected from the group consisting of OCT-4, KLF-4, SOX-2, GLIS1, and c-MYC;
   wherein prior to cutting the umbilical cord into smaller cut pieces, the umbilical cord is from 0.5-2.0 cm in length and comprises an artery;
   wherein the isolated perivascular cells express one or more transcription factor associated with undifferentiated stem cells; and the transcription factor is OCT-4, SOX-2, or Nanog.

2. The method according to claim 1, wherein
maintaining the isolated perivascular cells additionally comprises:
freezing the isolated perivascular cells; and
thawing and restoring the isolated perivascular cells to viability.

3. The method according to claim 1, wherein the collagenase is Type I at 1 mg/mL.

4. The method according to claim 2, wherein freezing the isolated perivascular cells comprises:
washing the isolated perivascular cells with PBS;
adding trypsin-EDTA;
harvesting the isolated perivascular cells into a tube containing maintenance medium;
separating the isolated perivascular cells from the maintenance medium; cooling the isolated perivascular cells to 4° C.;
mixing the isolated perivascular cells with a freezing medium at 4° C., said freezing medium comprising DMSO;
transferring the freezing medium containing the isolated perivascular cells to vials pre-chilled to −70° C.;
storing the vials at −70° C. for 24 h; and
storing the vials in liquid nitrogen.

5. The method according to claim 2, wherein thawing and restoring the isolated perivascular cells comprises:

warming the vials to 37° C.;

separating the isolated perivascular cells from the freezing medium;

mixing the isolated perivascular cells with maintenance medium;

maintaining the maintenance medium containing the isolated perivascular cells under appropriate growth conditions of 37° C., 5% $CO_2$, for 24 hours;

replacing the maintenance medium with new maintenance medium; and maintaining the new maintenance medium containing the material under appropriate growth conditions, said conditions being 37° C., 5% $CO_2$ and changing the new maintenance medium every 3-7 days.

6. The method according to claim 1, wherein maintaining the isolated perivascular cells further comprises: (i) aspirating the medium from the cells when the density of cells exceeds about 70% of the surface of a culture dish or flask in which the cells are maintained; (ii) washing the cells with PBS; (iii) adding trypsin-EDTA to cover the cells until the cells lift off of the dish or flask; and (iv) resuspending the cells in maintenance medium.

7. A method of isolating pluripotent human umbilical cord perivascular cells for screening of a drug candidate to treat cardiovascular injury or heart disease, wherein the isolated perivascular cells differentiate into cardiomyocytes expressing cTnI, wherein the pluripotent human umbilical cord perivascular cells are obtained by:

collecting an umbilical cord from fetal tissue obtained at less than 13 weeks of gestation, by collecting fetal placenta tissue by surgical aspiration; and separating the umbilical cord from the fetal placenta tissue;

treating the umbilical cord to obtain isolated perivascular cells, by:
   washing the umbilical cord with PBS,
   cutting the umbilical cord, comprising an artery and two vessels, into smaller cut pieces,
   treating the cut pieces with collagenase to obtain isolated perivascular cells, and
   washing the isolated perivascular cells with PBS; and
incubating the isolated perivascular cells, by suspending the isolated perivascular cells in a maintenance medium comprising α-MEM, penicillin-streptomycin, and amphotericin; and maintaining the isolated perivascular cells by:
   washing the isolated perivascular cells with PBS;
   adding trypsin-EDTA;
   harvesting the isolated perivascular cells into a tube containing maintenance medium;
   separating the isolated perivascular cells from the maintenance medium;
   mixing the isolated perivascular cells with new maintenance medium;
   diluting the new maintenance medium containing the isolated perivascular cells with additional maintenance medium to obtain a diluted maintenance medium containing the isolated perivascular cells;
   maintaining the diluted maintenance medium containing the isolated perivascular cells under appropriate growth conditions of 37° C., 5% $CO_2$ in a maintenance medium, and changing the maintenance medium every 3-7 days; and
   suspending the maintained cells;
wherein prior to cutting the umbilical cord into smaller cut pieces, the umbilical cord is from 0.5-2.0 cm in length and comprises an artery;

wherein the isolated perivascular cells express one or more transcription factor associated with undifferentiated stem cells; and the transcription factor is OCT-4, SOX-2, or Nanog; and wherein efficacy of the drug candidate is evaluated upon exposure of the isolated perivascular cells thereto.

8. The method of claim 7, wherein after the step of maintaining the isolated perivascular cells, said cells are reprogrammed by adding thereto at least one gene reprogramming factor selected from the group consisting of OCT-4, KLF-4, SOX-2, GLIS1, and c-MYC.

9. The method according to claim 7, wherein
maintaining the isolated perivascular cells additionally comprises:
freezing the isolated perivascular cells; and
thawing and restoring the isolated perivascular cells to viability.

10. The method according to claim 7, wherein the collagenase is Type I at 1 mg/mL.

11. The method according to claim 9, wherein freezing the isolated perivascular cells comprises:
washing the isolated perivascular cells with PBS;
adding trypsin-EDTA;
harvesting the isolated perivascular cells into a tube containing maintenance medium;
separating the isolated perivascular cells from the maintenance medium; cooling the isolated perivascular cells to 4° C.;
mixing the isolated perivascular cells with a freezing medium at 4° C., said freezing medium comprising DMSO;
transferring the freezing medium containing the isolated perivascular cells to vials pre-chilled to −70° C.;
storing the vials at −70° C. for 24 h; and
storing the vials in liquid nitrogen.

12. The method according to claim 9, wherein thawing and restoring the isolated perivascular cells comprises:
warming the vials to 37° C.;
separating the isolated perivascular cells from the freezing medium;
mixing the isolated perivascular cells with maintenance medium;
maintaining the maintenance medium containing the isolated perivascular cells under appropriate growth conditions of 37° C., 5% $CO_2$, for 24 hours;
replacing the maintenance medium with new maintenance medium; and
maintaining the new maintenance medium containing the material under appropriate growth conditions, said conditions being 37° C., 5% $CO_2$ and changing the new maintenance medium every 3-7 days.

13. The method according to claim 7, wherein maintaining the isolated perivascular cells further comprises: (i) aspirating the medium from the cells when the density of cells exceeds about 70% of the surface of a culture dish or flask in which the cells are maintained; (ii) 30 washing the cells with PBS; (iii) adding trypsin-EDTA to cover the cells until the cells lift off of the dish or flask; and (iv) resuspending the cells in maintenance medium.

14. A method of isolating pluripotent human umbilical cord perivascular cells for preparing a cell-free composition for treating an inflammatory condition, wherein the isolated perivascular cells are differentiated into, or reprogrammed as pluripotent cells for differentiation into, a homogeneous perivascular cell population with generational stability,
wherein the pluripotent human umbilical cord perivascular cells are obtained by:

collecting an umbilical cord from fetal tissue obtained at less than 13 weeks of gestation, by collecting fetal placenta tissue by surgical aspiration; and separating the umbilical cord from the fetal placenta tissue;

treating the umbilical cord to obtain isolated perivascular cells, by:
washing the umbilical cord with PBS,
cutting the umbilical cord, comprising an artery and two vessels, into smaller cut pieces,
treating the cut pieces with collagenase to obtain isolated perivascular cells, and
washing the isolated perivascular cells with PBS; and incubating the isolated perivascular cells, by suspending the isolated perivascular cells in a maintenance medium comprising α-MEM, penicillin-streptomycin, and amphotericin; and maintaining the isolated perivascular cells by:
washing the isolated perivascular cells with PBS;
adding trypsin-EDTA;
harvesting the isolated perivascular cells into a tube containing maintenance medium;
separating the isolated perivascular cells from the maintenance medium;
mixing the isolated perivascular cells with new maintenance medium;
diluting the new maintenance medium containing the isolated perivascular cells with additional maintenance medium to obtain a diluted maintenance medium containing the isolated perivascular cells;
maintaining the diluted maintenance medium containing the isolated perivascular cells under appropriate growth conditions of 37° C., 5% $CO_2$ in a maintenance medium, and changing the maintenance medium every 3-7 days;
suspending the maintained cells;
optionally reprogramming the isolated perivascular cells by adding thereto at least one gene reprogramming factor selected from the group consisting of OCT-4, KLF-4, SOX-2, GLIS1, and c-MYC; and
preparing the cell-free composition from the maintenance medium comprising secretions of the isolated perivascular cells;

wherein prior to cutting the umbilical cord into smaller cut pieces, the umbilical cord is from 0.5-2.0 cm in length and comprises an artery;

wherein the isolated perivascular cells express one or more transcription factor associated with undifferentiated stem cells; and the transcription factor is OCT-4, SOX-2, or Nanog.

15. The method according to claim 14, wherein maintaining the isolated perivascular cells additionally comprises:
freezing the isolated perivascular cells; and
thawing and restoring the isolated perivascular cells to viability.

16. The method according to claim 14, wherein the collagenase is Type I at 1 mg/mL.

17. The method according to claim 15, wherein freezing the isolated perivascular cells comprises:
washing the isolated perivascular cells with PBS;
adding trypsin-EDTA;
harvesting the isolated perivascular cells into a tube containing maintenance medium;
separating the isolated perivascular cells from the maintenance medium;
cooling the isolated perivascular cells to 4° C.;
mixing the isolated perivascular cells with a freezing medium at 4° C., said freezing medium comprising DMSO;
transferring the freezing medium containing the isolated perivascular cells to vials pre-chilled to −70° C.;
storing the vials at −70° C. for 24 h; and
storing the vials in liquid nitrogen.

18. The method according to claim 15, wherein thawing and restoring the isolated perivascular cells comprises:
warming the vials to 37° C.;
separating the isolated perivascular cells from the freezing medium;
mixing the isolated perivascular cells with maintenance medium;
maintaining the maintenance medium containing the isolated perivascular cells under appropriate growth conditions of 37° C., 5% $CO_2$, for 24 hours;
replacing the maintenance medium with new maintenance medium; and
maintaining the new maintenance medium containing the material under appropriate growth conditions, said conditions being 37° C., 5% $CO_2$ and changing the new maintenance medium every 3-7 days.

19. The method according to claim 14, wherein maintaining the isolated perivascular cells further comprises: (i) aspirating the medium from the cells when the density of cells exceeds about 70% of the surface of a culture dish or flask in which the cells are maintained; (ii) washing the cells with PBS; (iii) adding trypsin-EDTA to cover the cells until the cells lift off of the dish or flask; and (iv) resuspending the cells in maintenance medium.

20. The method according to claim 14, wherein the optional step of reprogramming the isolated perivascular cells is conducted after the step of suspending.

* * * * *